(12) United States Patent
Wong et al.

(10) Patent No.: US 10,085,839 B2
(45) Date of Patent: Oct. 2, 2018

(54) PATIENT-SPECIFIC AND PATIENT-ENGINEERED ORTHOPEDIC IMPLANTS

(75) Inventors: Terrance Wong, Needham, MA (US); John Slamin, Wrentham, MA (US); Philipp Lang, Lexington, MA (US)

(73) Assignee: ConforMIS, Inc., Billerica, MA (US)

( * ) Notice: Subject to any disclaimer, the term of this patent is extended or adjusted under 35 U.S.C. 154(b) by 0 days.

(21) Appl. No.: 12/965,493

(22) Filed: Dec. 10, 2010

(65) Prior Publication Data
US 2011/0144760 A1 Jun. 16, 2011

Related U.S. Application Data

(60) Provisional application No. 61/284,022, filed on Dec. 11, 2009.

(51) Int. Cl.
*A61F 2/38* (2006.01)
*A61F 2/50* (2006.01)
(Continued)

(52) U.S. Cl.
CPC ............ *A61F 2/30942* (2013.01); *A61F 2/38* (2013.01); *A61F 2/4657* (2013.01); *A61F 2/30756* (2013.01); *A61F 2/30767* (2013.01); *A61F 2/3872* (2013.01); *A61F 2/3877* (2013.01); *A61F 2002/30011* (2013.01); *A61F 2002/30062* (2013.01); *A61F 2002/30092* (2013.01); *A61F 2002/30163* (2013.01); *A61F 2002/30604* (2013.01); *A61F 2002/30616* (2013.01); *A61F 2002/30892* (2013.01); *A61F 2002/30894* (2013.01); *A61F 2002/30929* (2013.01);
(Continued)

(58) Field of Classification Search
CPC ........ A61F 2/30942; A61F 2002/30604; A61F 2002/607; A61F 2002/704; A61F 2002/30616; A61F 2002/30617; A61F 2240/001; A61F 2/30; A61F 2/38; A61F 2/3859; A61F 2/3868; A61F 2/389; A61F 2/64; A61F 2002/2825; A61F 2002/2835
USPC ...................... 623/13.12–13.16, 20.14–20.36
See application file for complete search history.

(56) References Cited

U.S. PATENT DOCUMENTS

| 3,314,420 A | 4/1967 | Smith et al. ...................... 128/92 |
| 3,605,123 A | 9/1971 | Hahn .................................... 3/1 |

(Continued)

FOREIGN PATENT DOCUMENTS

| CN | 86209787 | 11/1987 | ............... A61F 2/38 |
| CN | 2305966 | 2/1999 | ............... A61F 2/28 |

(Continued)

OTHER PUBLICATIONS

Adam et al., "NMR tomography of the cartilage structures of the knee joint with 3-D volume image combined with a rapid optical-imaging computer," ROFO Fortschr. Geb. Rontgenstr. Nuklearmed., 150(1): 44-48 (1989) Abstract Only.
(Continued)

*Primary Examiner* — Ann Schillinger
(74) *Attorney, Agent, or Firm* — Sunstein Kann Murphy & Timbers LLP

(57) ABSTRACT

Disclosed herein are methods and devices for repairing a knee joint, including customizable and/or highly selectable implants and/or implant components for each patient to provide optimal fit and function.

14 Claims, 40 Drawing Sheets

(51) Int. Cl.
*A61F 2/30* (2006.01)
*A61F 2/46* (2006.01)

(52) U.S. Cl.
CPC ............... *A61F 2002/30948* (2013.01); *A61F 2002/3895* (2013.01); *A61F 2210/0004* (2013.01); *A61F 2210/0014* (2013.01); *A61F 2230/0028* (2013.01); *A61F 2250/0023* (2013.01); *A61F 2310/00017* (2013.01); *A61F 2310/00023* (2013.01); *A61F 2310/00029* (2013.01); *A61F 2310/00047* (2013.01); *A61F 2310/00065* (2013.01); *A61F 2310/00071* (2013.01); *A61F 2310/00077* (2013.01); *A61F 2310/00083* (2013.01); *A61F 2310/00107* (2013.01); *A61F 2310/00113* (2013.01); *A61F 2310/00119* (2013.01); *A61F 2310/00131* (2013.01); *A61F 2310/00149* (2013.01); *A61F 2310/00155* (2013.01); *A61F 2310/00395* (2013.01); *A61F 2310/00592* (2013.01)

(56) References Cited

U.S. PATENT DOCUMENTS

| | | | | |
|---|---|---|---|---|
| 3,694,820 | A | 10/1972 | Scales et al. | 3/1 |
| 3,798,679 | A | 3/1974 | Ewald | 3/1 |
| 3,808,606 | A | 5/1974 | Tronzo | 3/1 |
| 3,816,855 | A | 6/1974 | Saleh | 3/1 |
| 3,843,975 | A | 10/1974 | Tronzo | 3/1 |
| 3,852,830 | A | 12/1974 | Marmor | 3/1 |
| 3,855,638 | A | 12/1974 | Pillar | 3/1 |
| 3,938,198 | A | 2/1976 | Kahn et al. | 3/1.912 |
| 3,987,499 | A | 10/1976 | Scharbach et al. | 3/1.91 |
| 3,991,425 | A | 11/1976 | Martin et al. | 3/1.91 |
| 4,052,753 | A | 10/1977 | Dedo | 3/1 |
| 4,055,862 | A | 11/1977 | Farling | 3/1.91 |
| 4,085,466 | A | 4/1978 | Goodfellow et al. | 3/1.91 |
| 4,098,626 | A | 7/1978 | Graham et al. | 149/19.4 |
| 4,164,793 | A | 8/1979 | Swanson | 3/1.91 |
| 4,178,641 | A | 12/1979 | Grundei et al. | 3/1.911 |
| 4,203,444 | A | 5/1980 | Bonnell et al. | 128/276 |
| 4,207,627 | A | 6/1980 | Cloutier | 3/1.911 |
| 4,211,228 | A | 7/1980 | Cloutier | 128/303 |
| 4,213,816 | A | 7/1980 | Morris | 156/245 |
| 4,219,893 | A | 9/1980 | Noiles | 3/1.911 |
| 4,280,231 | A | 7/1981 | Swanson | 3/1.91 |
| 4,309,778 | A | 1/1982 | Buechel et al. | 3/1.911 |
| 4,340,978 | A | 7/1982 | Buechel et al. | 3/1.911 |
| 4,344,193 | A | 8/1982 | Kenny | 3/1.911 |
| 4,368,040 | A | 1/1983 | Weissman | 433/36 |
| 4,436,684 | A | 3/1984 | White | 264/138 |
| 4,459,985 | A | 7/1984 | McKay et al. | 128/303 R |
| 4,502,161 | A | 3/1985 | Wall | 3/1.91 |
| 4,575,805 | A | 3/1986 | Moermann et al. | 364/474 |
| 4,586,496 | A | 5/1986 | Keller | 128/92 E |
| 4,594,380 | A | 6/1986 | Chapin et al. | 524/140 |
| 4,601,290 | A | 7/1986 | Effron et al. | 128/305 |
| 4,609,551 | A | 9/1986 | Caplan et al. | 424/95 |
| 4,627,853 | A | 12/1986 | Campbell et al. | 623/16 |
| 4,637,382 | A | 1/1987 | Walker | |
| 4,655,227 | A | 4/1987 | Gracovetsky | 128/781 |
| 4,662,889 | A | 5/1987 | Zichner et al. | 623/20 |
| 4,699,156 | A | 10/1987 | Gracovetsky | 128/781 |
| 4,714,472 | A | 12/1987 | Averill et al. | 623/20 |
| 4,714,474 | A | 12/1987 | Brooks, Jr. et al. | 623/20 |
| 4,769,040 | A | 9/1988 | Wevers | 623/20 |
| 4,813,436 | A | 3/1989 | Au | 128/779 |
| 4,822,365 | A * | 4/1989 | Walker et al. | 128/898 |
| 4,823,807 | A | 4/1989 | Russell et al. | 128/773 |
| 4,841,975 | A | 6/1989 | Woolson | 128/653 |
| 4,846,835 | A | 7/1989 | Grande | 623/11 |
| 4,865,607 | A | 9/1989 | Witzel et al. | 623/20 |
| 4,872,452 | A | 10/1989 | Alexson | 128/92 VJ |
| 4,880,429 | A | 11/1989 | Stone | 623/18 |
| 4,883,488 | A | 11/1989 | Bloebaum et al. | 3/20 |
| 4,888,021 | A | 12/1989 | Forte et al. | 623/20 |
| 4,936,853 | A | 6/1990 | Fabian et al. | 623/20 |
| 4,936,862 | A | 6/1990 | Walker et al. | 623/23 |
| 4,944,757 | A | 7/1990 | Martinez et al. | 623/20 |
| 4,979,949 | A | 12/1990 | Matsen, III et al. | 606/53 |
| 5,007,936 | A | 4/1991 | Woolson | 623/23 |
| 5,019,103 | A | 5/1991 | Van Zile et al. | 623/20 |
| 5,021,061 | A | 6/1991 | Wevers et al. | 623/20 |
| 5,041,138 | A | 8/1991 | Vacanti et al. | 623/16 |
| 5,047,057 | A | 9/1991 | Lawes | 623/20 |
| 5,059,216 | A | 10/1991 | Winters | 623/20 |
| 5,067,964 | A | 11/1991 | Richmond et al. | 623/18 |
| 5,099,859 | A | 3/1992 | Bell | 128/781 |
| 5,108,452 | A | 4/1992 | Fallin | 623/23 |
| 5,123,927 | A | 6/1992 | Duncan et al. | 623/20 |
| 5,129,908 | A | 7/1992 | Peterson | 606/88 |
| 5,133,759 | A | 7/1992 | Turner | 623/20 |
| 5,147,405 | A | 9/1992 | Van et al. | |
| 5,150,304 | A | 9/1992 | Berchem et al. | 364/474.24 |
| 5,152,797 | A | 10/1992 | Luckman et al. | 623/20 |
| 5,154,178 | A | 10/1992 | Shah | 128/653.2 |
| 5,162,430 | A | 11/1992 | Rhee et al. | 525/54.1 |
| 5,171,244 | A | 12/1992 | Caspari et al. | 606/88 |
| 5,171,322 | A | 12/1992 | Kenny | 623/18 |
| 5,197,985 | A | 3/1993 | Caplan et al. | 623/16 |
| 5,206,023 | A | 4/1993 | Hunziker | 424/423 |
| 5,226,914 | A | 7/1993 | Caplan et al. | 623/16 |
| 5,234,433 | A | 8/1993 | Bert et al. | 606/88 |
| 5,245,282 | A | 9/1993 | Mugler, III et al. | 324/309 |
| 5,246,013 | A | 9/1993 | Frank et al. | 128/774 |
| 5,246,530 | A | 9/1993 | Bugle et al. | 156/643 |
| 5,270,300 | A | 12/1993 | Hunziker | 514/12 |
| 5,274,565 | A | 12/1993 | Reuben | 364/474.24 |
| 5,282,868 | A | 2/1994 | Bahler | 623/20 |
| 5,288,797 | A | 2/1994 | Khalil et al. | 524/872 |
| 5,303,148 | A | 4/1994 | Mattson et al. | 364/413.01 |
| 5,306,307 | A | 4/1994 | Senter et al. | 623/17 |
| 5,306,311 | A | 4/1994 | Stone et al. | 623/18 |
| 5,314,478 | A | 5/1994 | Oka et al. | 623/18 |
| 5,314,482 | A | 5/1994 | Goodfellow et al. | 623/20 |
| 5,320,102 | A | 6/1994 | Paul et al. | 128/653.2 |
| 5,326,363 | A | 7/1994 | Aikins | 623/20 |
| 5,326,365 | A | 7/1994 | Alvine | 623/21 |
| 5,336,266 | A | 8/1994 | Caspari et al. | 623/20 |
| 5,344,459 | A | 9/1994 | Swartz | 623/18 |
| 5,360,446 | A | 11/1994 | Kennedy | 623/16 |
| 5,365,996 | A | 11/1994 | Crook | 164/45 |
| 5,368,858 | A | 11/1994 | Hunziker | 424/423 |
| 5,403,319 | A | 4/1995 | Matsen, III et al. | 606/88 |
| 5,405,395 | A | 4/1995 | Coates | 623/20 |
| 5,413,116 | A | 5/1995 | Radke et al. | 128/777 |
| 5,423,828 | A | 6/1995 | Benson | 606/102 |
| 5,433,215 | A | 7/1995 | Athanasiou et al. | 128/774 |
| 5,445,152 | A | 8/1995 | Bell et al. | 128/653.5 |
| 5,448,489 | A | 9/1995 | Reuben | 364/474.05 |
| 5,468,787 | A | 11/1995 | Braden et al. | 523/113 |
| 5,478,739 | A | 12/1995 | Slivka et al. | 435/240.23 |
| 5,489,309 | A | 2/1996 | Lackey et al. | 623/19 |
| 5,501,687 | A | 3/1996 | Willert et al. | 606/94 |
| 5,503,162 | A | 4/1996 | Athanasiou et al. | 128/774 |
| 5,507,820 | A | 4/1996 | Pappas | 623/20 |
| 5,510,121 | A | 4/1996 | Rhee et al. | 424/520 |
| 5,522,900 | A | 6/1996 | Hollister | 623/18 |
| 5,523,843 | A | 6/1996 | Yamane et al. | 356/363 |
| 5,541,515 | A | 7/1996 | Tsujita | 324/318 |
| 5,549,690 | A | 8/1996 | Hollister et al. | 623/21 |
| 5,554,190 | A | 9/1996 | Draenert | 623/16 |
| 5,556,432 | A | 9/1996 | Kubein-Meesenburg et al. | 623/20 |
| 5,560,096 | A | 10/1996 | Stephens | 29/558 |
| 5,564,437 | A | 10/1996 | Bainville et al. | 128/774 |
| 5,571,191 | A | 11/1996 | Fitz | 623/17 |
| 5,571,205 | A | 11/1996 | James | 623/24 |
| 5,609,640 | A | 3/1997 | Johnson | 623/20 |
| 5,611,802 | A | 3/1997 | Samuelson et al. | 606/86 |
| 5,616,146 | A | 4/1997 | Murray | 606/80 |
| 5,632,745 | A | 5/1997 | Schwartz | 606/75 |
| 5,671,741 | A | 9/1997 | Lang et al. | 128/653.2 |
| 5,681,354 | A | 10/1997 | Eckhoff | 623/20 |

(56) References Cited

U.S. PATENT DOCUMENTS

| | | | |
|---|---|---|---|
| 5,682,886 A | 11/1997 | Delp et al. | 128/653.1 |
| 5,683,466 A | 11/1997 | Vitale | 623/18 |
| 5,683,468 A | 11/1997 | Pappas | 623/20 |
| 5,684,562 A | 11/1997 | Fujieda | 351/212 |
| 5,687,210 A | 11/1997 | Maitrejean et al. | 378/57 |
| 5,690,635 A | 11/1997 | Matsen, III et al. | 606/88 |
| 5,702,463 A | 12/1997 | Pothier et al. | 623/20 |
| 5,723,331 A | 3/1998 | Tubo et al. | 435/366 |
| 5,728,162 A | 3/1998 | Eckhoff | 623/20 |
| 5,735,277 A | 4/1998 | Schuster | 128/653.1 |
| 5,741,215 A | 4/1998 | D'Urso | 600/407 |
| 5,749,362 A | 5/1998 | Funda et al. | 128/653.1 |
| 5,749,874 A | 5/1998 | Schwartz | 606/75 |
| 5,749,876 A | 5/1998 | Duvillier et al. | 606/86 |
| 5,759,205 A | 6/1998 | Valentini | 623/16 |
| 5,768,134 A | 6/1998 | Swaelens et al. | 364/468.28 |
| 5,769,899 A | 6/1998 | Schwartz et al. | 623/18 |
| 5,772,595 A | 6/1998 | Votruba et al. | 600/415 |
| 5,779,651 A | 7/1998 | Buschmann et al. | 600/587 |
| 5,786,217 A | 7/1998 | Tubo et al. | 435/402 |
| 5,810,006 A | 9/1998 | Votruba et al. | 128/653.2 |
| 5,824,085 A | 10/1998 | Sahay et al. | 623/16 |
| 5,824,102 A | 10/1998 | Buscayret | 623/20 |
| 5,827,289 A | 10/1998 | Reiley et al. | 606/86 |
| 5,832,422 A | 11/1998 | Wiedenhoefer | 702/154 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,871,018 A | 2/1999 | Delp et al. | 128/898 |
| 5,871,540 A | 2/1999 | Weissman et al. | 623/20 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia, III et al. | 364/578 |
| 5,885,296 A | 3/1999 | Masini | 606/86 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,643 A | 5/1999 | Walker | 623/20 |
| 5,906,934 A | 5/1999 | Grande et al. | 435/325 |
| 5,913,821 A | 6/1999 | Farese et al. | 600/425 |
| 5,916,220 A | 6/1999 | Masini | 606/88 |
| 5,928,945 A | 7/1999 | Seliktar et al. | 435/395 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,968,099 A | 10/1999 | Badorf et al. | 623/20 |
| 5,972,385 A | 10/1999 | Liu et al. | 424/486 |
| 5,995,738 A | 11/1999 | DiGioia, III et al. | 395/500.32 |
| 6,002,859 A | 12/1999 | DiGioia, III et al. | 395/500.32 |
| 6,013,103 A | 1/2000 | Kaufman et al. | 623/20 |
| 6,039,764 A | 3/2000 | Pottenger et al. | |
| 6,046,379 A | 4/2000 | Stone et al. | 623/11 |
| 6,057,927 A | 5/2000 | Lévesque et al. | 356/432 T |
| 6,078,680 A | 6/2000 | Yoshida et al. | 382/128 |
| 6,081,577 A | 6/2000 | Webber | 378/23 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,102,916 A | 8/2000 | Masini | 606/88 |
| 6,102,955 A | 8/2000 | Mendes et al. | 623/20 |
| 6,110,209 A | 8/2000 | Stone | 623/16.11 |
| 6,112,109 A | 8/2000 | D'Urso | 600/407 |
| 6,120,541 A | 9/2000 | Johnson | 623/14.12 |
| 6,120,543 A | 9/2000 | Kubein-Meesenburg et al. | 623/20 |
| 6,126,690 A | 10/2000 | Ateshian et al. | 623/18 |
| 6,139,578 A | 10/2000 | Lee et al. | 623/16.11 |
| 6,146,422 A | 11/2000 | Lawson | 623/17.16 |
| 6,151,521 A | 11/2000 | Guo et al. | 600/407 |
| 6,152,960 A | 11/2000 | Pappas | 623/20.31 |
| 6,156,069 A | 12/2000 | Amstutz | 623/22.11 |
| 6,161,080 A | 12/2000 | Aouni-Ateshian et al. | 703/11 |
| 6,162,208 A | 12/2000 | Hipps | 606/1 |
| 6,165,221 A | 12/2000 | Schmotzer | 623/20.11 |
| 6,171,340 B1 | 1/2001 | McDowell | 623/18.11 |
| 6,175,655 B1 | 1/2001 | George, III et al. | 382/257 |
| 6,178,225 B1 | 1/2001 | Zur et al. | 378/98.2 |
| 6,187,010 B1 | 2/2001 | Masini | 606/86 |
| 6,190,415 B1 | 2/2001 | Cooke et al. | |
| 6,197,064 B1 | 3/2001 | Haines et al. | 623/20.31 |
| 6,197,325 B1 | 3/2001 | MacPhee et al. | 424/426 |
| 6,200,606 B1 | 3/2001 | Peterson et al. | 424/574 |
| 6,203,576 B1 | 3/2001 | Afriat et al. | 623/20.27 |
| 6,205,411 B1 | 3/2001 | DiGioia, III et al. | 703/11 |
| 6,206,927 B1 | 3/2001 | Fell et al. | 623/20.29 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,224,632 B1 | 5/2001 | Pappas et al. | 623/20.34 |
| 6,235,060 B1 | 5/2001 | Kubein-Meesenburg et al. | 623/20.31 |
| 6,249,692 B1 | 6/2001 | Cowin | 600/407 |
| 6,251,143 B1 | 6/2001 | Schwartz et al. | 623/23.72 |
| 6,254,639 B1 | 7/2001 | Peckitt | 623/11.11 |
| 6,261,296 B1 | 7/2001 | Aebi et al. | 606/90 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,289,115 B1 | 9/2001 | Takeo | 382/130 |
| 6,289,753 B1 | 9/2001 | Basser et al. | 73/866 |
| 6,299,645 B1 | 10/2001 | Ogden | 623/20.21 |
| 6,299,905 B1 | 10/2001 | Peterson et al. | 424/486 |
| 6,302,582 B1 | 10/2001 | Nord et al. | 378/207 |
| 6,310,477 B1 | 10/2001 | Schneider | 324/307 |
| 6,310,619 B1 | 10/2001 | Rice | 345/420 |
| 6,316,153 B1 | 11/2001 | Goodman et al. | 430/8 |
| 6,319,712 B1 | 11/2001 | Meenen et al. | 435/395 |
| 6,322,588 B1 | 11/2001 | Ogle et al. | 623/1.46 |
| 6,325,828 B1 | 12/2001 | Dennis et al. | 623/20.14 |
| 6,328,765 B1 | 12/2001 | Hardwick et al. | 623/23.72 |
| 6,334,006 B1 | 12/2001 | Tanabe | 385/12 |
| 6,334,066 B1 | 12/2001 | Rupprecht et al. | 600/411 |
| 6,342,075 B1 | 1/2002 | MacArthur | 623/20.14 |
| 6,344,043 B1 | 2/2002 | Pappas | 606/96 |
| 6,344,059 B1 | 2/2002 | Krakovits et al. | 623/20.31 |
| 6,352,558 B1 | 3/2002 | Spector | 623/18.11 |
| 6,358,253 B1 | 3/2002 | Torrie et al. | 606/96 |
| 6,365,405 B1 | 4/2002 | Salzmann et al. | 435/366 |
| 6,371,958 B1 | 4/2002 | Overaker | 606/72 |
| 6,373,250 B1 | 4/2002 | Tsoref et al. | 324/309 |
| 6,375,658 B1 | 4/2002 | Hangody et al. | 606/80 |
| 6,379,367 B1 | 4/2002 | Vibe-Hansen et al. | 606/151 |
| 6,379,388 B1 | 4/2002 | Ensign et al. | 623/20.34 |
| 6,382,028 B1 | 5/2002 | Wooh et al. | 73/602 |
| 6,383,228 B1 | 5/2002 | Schmotzer | 623/23.35 |
| 6,387,131 B1 | 5/2002 | Miehlke et al. | 623/20.15 |
| 6,402,786 B1 | 6/2002 | Insall et al. | 623/20.35 |
| 6,429,013 B1 | 8/2002 | Halvorsen et al. | 435/377 |
| 6,443,988 B2 | 9/2002 | Felt et al. | 623/17.12 |
| 6,443,991 B1 | 9/2002 | Running | 623/20.27 |
| 6,444,222 B1 | 9/2002 | Asculai et al. | 424/484 |
| 6,450,978 B1 | 9/2002 | Brosseau et al. | 600/595 |
| 6,459,948 B1 | 10/2002 | Ateshian et al. | 700/117 |
| 6,468,314 B2 | 10/2002 | Schwartz et al. | 623/23.72 |
| 6,479,996 B1 | 11/2002 | Hoogeveen et al. | 324/309 |
| 6,482,209 B1 | 11/2002 | Engh et al. | 606/79 |
| 6,510,334 B1 | 1/2003 | Schuster et al. | 600/407 |
| 6,514,514 B1 | 2/2003 | Atkinson et al. | 424/423 |
| 6,520,964 B2 | 2/2003 | Tallarida et al. | 396/567 |
| 6,533,737 B1 | 3/2003 | Brosseau et al. | 600/595 |
| 6,556,855 B2 | 4/2003 | Thesen | 600/419 |
| 6,558,421 B1 | 5/2003 | Fell et al. | 623/14.12 |
| 6,560,476 B1 | 5/2003 | Pelletier et al. | 600/410 |
| 6,575,980 B1 | 6/2003 | Robie et al. | 606/88 |
| 6,591,581 B2 | 7/2003 | Schmieding | 53/396 |
| 6,592,624 B1 | 7/2003 | Fraser et al. | 623/17.16 |
| 6,623,526 B1 | 9/2003 | Lloyd | 623/20.28 |
| 6,626,945 B2 | 9/2003 | Simon et al. | 623/17.19 |
| 6,632,235 B2 | 10/2003 | Weikel et al. | 606/192 |
| 6,652,587 B2 | 11/2003 | Felt et al. | 623/20.16 |

(56) References Cited

U.S. PATENT DOCUMENTS

| | | | |
|---|---|---|---|
| 6,679,917 B2 | 1/2004 | Ek | 623/20.14 |
| 6,690,816 B2 | 2/2004 | Aylward et al. | 382/128 |
| 6,692,448 B2 | 2/2004 | Tanaka et al. | 600/587 |
| 6,702,821 B2 | 3/2004 | Bonutti | 606/88 |
| 6,712,856 B1 | 3/2004 | Carignan et al. | 623/20.35 |
| 6,719,794 B2 | 4/2004 | Gerber et al. | 623/17.11 |
| 6,770,078 B2 | 8/2004 | Bonutti | 606/88 |
| 6,772,026 B2 | 8/2004 | Bradbury et al. | 700/98 |
| 6,799,066 B2 | 9/2004 | Steines et al. | 600/407 |
| 6,816,607 B2 | 11/2004 | O'Donnell et al. | 382/131 |
| 6,835,377 B2 | 12/2004 | Goldberg et al. | 424/93.7 |
| 6,855,165 B2 | 2/2005 | Fell et al. | 623/14.12 |
| 6,873,741 B2 | 3/2005 | Li | 382/266 |
| 6,893,463 B2 | 5/2005 | Fell et al. | 623/14.12 |
| 6,893,467 B1 | 5/2005 | Bercovy | 623/20.14 |
| 6,902,582 B2 | 6/2005 | Kubein-Meesenburg et al. | 623/20.31 |
| 6,905,514 B2 | 6/2005 | Carignan et al. | 623/20.35 |
| 6,911,044 B2 | 6/2005 | Fell et al. | 623/14.12 |
| 6,916,341 B2 | 7/2005 | Rolston | 623/20.3 |
| 6,923,817 B2 | 8/2005 | Carson et al. | 606/130 |
| 6,923,831 B2 | 8/2005 | Fell et al. | 623/14.12 |
| 6,932,842 B1 | 8/2005 | Litschko et al. | 623/16.11 |
| 6,964,687 B1 | 11/2005 | Bernard et al. | 623/17.16 |
| 6,966,928 B2 | 11/2005 | Fell et al. | 623/14.12 |
| 6,978,188 B1 | 12/2005 | Christensen | 700/118 |
| 6,984,981 B2 | 1/2006 | Tamez-Peña et al. | 324/309 |
| 6,998,841 B1 | 2/2006 | Tamez-Peña et al. | 324/302 |
| 7,020,314 B1 | 3/2006 | Suri et al. | 382/130 |
| 7,050,534 B2 | 5/2006 | Lang | 378/54 |
| 7,058,159 B2 | 6/2006 | Lang et al. | 378/54 |
| 7,058,209 B2 | 6/2006 | Chen et al. | 382/117 |
| 7,060,101 B2 | 6/2006 | O'Connor et al. | 623/20.32 |
| 7,105,026 B2 | 9/2006 | Johnson et al. | 623/20.14 |
| 7,115,131 B2 | 10/2006 | Engh et al. | 606/79 |
| 7,172,596 B2 | 2/2007 | Coon et al. | 606/87 |
| 7,174,282 B2 | 2/2007 | Hollister et al. | 703/2 |
| 7,184,814 B2 | 2/2007 | Lang et al. | 600/416 |
| 7,204,807 B2 | 4/2007 | Tsoref | 600/438 |
| 7,238,203 B2 | 7/2007 | Bagga et al. | 623/17.11 |
| 7,239,908 B1 | 7/2007 | Alexander et al. | 600/427 |
| 7,244,273 B2 | 7/2007 | Pedersen et al. | 623/14.12 |
| 7,245,697 B2 | 7/2007 | Lang | 378/54 |
| 7,264,635 B2 | 9/2007 | Suguro et al. | 623/20.14 |
| 7,292,674 B2 | 11/2007 | Lang | 378/54 |
| 7,326,252 B2 | 2/2008 | Otto et al. | 623/20.15 |
| 7,379,529 B2 | 5/2008 | Lang | 378/54 |
| 7,438,685 B2 | 10/2008 | Burdette et al. | 600/439 |
| 7,467,892 B2 | 12/2008 | Lang et al. | 378/207 |
| 7,468,075 B2 | 12/2008 | Lang et al. | 623/16.11 |
| 7,517,358 B2 | 4/2009 | Petersen | 606/247 |
| 7,520,901 B2 | 4/2009 | Engh et al. | 623/20.21 |
| 7,534,263 B2 | 5/2009 | Burdulis, Jr. et al. | 623/14.12 |
| 7,572,293 B2 | 8/2009 | Rhodes et al. | 623/20.32 |
| 7,603,192 B2 | 10/2009 | Martin et al. | 700/98 |
| 7,611,519 B2 | 11/2009 | Lefevre et al. | 606/102 |
| 7,611,653 B1 | 11/2009 | Elsner et al. | 264/255 |
| 7,615,054 B1 | 11/2009 | Bonutti | 606/88 |
| 7,618,451 B2 | 11/2009 | Berez et al. | 623/14.12 |
| 7,634,119 B2 | 12/2009 | Tsougarakis et al. | 382/128 |
| 7,678,152 B2 | 3/2010 | Suguro et al. | 623/20.27 |
| 7,718,109 B2 | 5/2010 | Robb et al. | 264/308 |
| 7,796,791 B2 | 9/2010 | Tsougarakis et al. | 382/128 |
| 7,799,077 B2 | 9/2010 | Lang et al. | 623/14.12 |
| 7,806,896 B1 | 10/2010 | Bonutti | 606/86 |
| 7,842,092 B2 | 11/2010 | Otto et al. | 623/18.11 |
| 7,881,768 B2 | 2/2011 | Lang et al. | 600/407 |
| 7,914,582 B2 | 3/2011 | Felt et al. | 623/20.16 |
| 7,935,151 B2 | 5/2011 | Haines | 623/20.35 |
| 7,981,158 B2 | 7/2011 | Fitz et al. | 623/17.16 |
| 7,983,777 B2 | 7/2011 | Melton et al. | 700/98 |
| 8,036,729 B2 | 10/2011 | Lang et al. | 600/407 |
| 8,062,302 B2 | 11/2011 | Lang et al. | 606/87 |
| 8,066,708 B2 | 11/2011 | Lang et al. | 606/88 |
| 8,070,821 B2 | 12/2011 | Roger | 623/20.17 |
| 8,077,950 B2 | 12/2011 | Tsougarakis et al. | 382/128 |
| 8,083,745 B2 | 12/2011 | Lang et al. | 606/87 |
| 8,086,336 B2 | 12/2011 | Christensen | 700/98 |
| 8,094,900 B2 | 1/2012 | Steines et al. | 382/128 |
| 8,105,330 B2 | 1/2012 | Fitz et al. | 606/88 |
| 8,112,142 B2 | 2/2012 | Alexander et al. | 600/407 |
| RE43,282 E | 3/2012 | Alexander et al. | 600/427 |
| 8,192,498 B2 | 6/2012 | Wagner et al. | 623/20.21 |
| 8,211,181 B2 | 7/2012 | Walker | 623/20.21 |
| 8,221,430 B2 | 7/2012 | Park et al. | 606/88 |
| 8,234,097 B2 | 7/2012 | Steines et al. | 703/1 |
| 8,236,061 B2 | 8/2012 | Heldreth et al. | 623/20.31 |
| 8,265,730 B2 | 9/2012 | Alexander et al. | 600/410 |
| 8,306,601 B2 | 11/2012 | Lang et al. | 600/407 |
| 8,311,306 B2 | 11/2012 | Pavlovskaia et al. | 382/131 |
| 8,337,501 B2 | 12/2012 | Fitz et al. | 606/86 |
| 8,337,507 B2 | 12/2012 | Lang et al. | 606/102 |
| 8,343,218 B2 | 1/2013 | Lang et al. | 623/16.11 |
| 8,352,056 B2 | 1/2013 | Lee et al. | 700/97 |
| 8,361,076 B2 | 1/2013 | Roose et al. | 606/88 |
| 8,366,771 B2 | 2/2013 | Burdulis, Jr. et al. | 623/14.12 |
| 8,369,926 B2 | 2/2013 | Lang et al. | 600/407 |
| 8,377,073 B2 | 2/2013 | Wasielewski | 606/102 |
| 8,377,129 B2 | 2/2013 | Fitz et al. | 623/14.12 |
| 8,380,471 B2 | 2/2013 | Iannotti et al. | 703/6 |
| 8,407,067 B2 | 3/2013 | Uthgenannt et al. | 705/2 |
| 8,439,926 B2 | 5/2013 | Bojarski et al. | 606/88 |
| 8,457,930 B2 | 6/2013 | Schroeder | 703/1 |
| 8,460,304 B2 | 6/2013 | Fitz et al. | 606/88 |
| 8,473,305 B2 | 6/2013 | Belcher et al. | 705/2 |
| 8,480,754 B2 | 7/2013 | Bojarski et al. | 623/20.35 |
| 8,486,150 B2 | 7/2013 | White et al. | 623/20.21 |
| 8,500,740 B2 | 8/2013 | Bojarski et al. | 606/86 R |
| 8,521,492 B2 | 8/2013 | Otto et al. | 703/6 |
| 8,529,568 B2 | 9/2013 | Bouadi | 606/84 |
| 8,529,630 B2 | 9/2013 | Bojarski et al. | 623/20.14 |
| 8,532,807 B2 | 9/2013 | Metzger | 700/98 |
| 8,545,569 B2 | 10/2013 | Fitz et al. | 623/20.14 |
| 8,551,099 B2 | 10/2013 | Lang et al. | 606/86 R |
| 8,551,102 B2 | 10/2013 | Fitz et al. | 606/88 |
| 8,551,103 B2 | 10/2013 | Fitz et al. | 606/88 |
| 8,551,169 B2 | 10/2013 | Fitz et al. | 623/14.12 |
| 8,556,906 B2 | 10/2013 | Fitz et al. | 606/87 |
| 8,556,907 B2 | 10/2013 | Fitz et al. | 606/87 |
| 8,556,971 B2 | 10/2013 | Lang | 623/14.12 |
| 8,556,983 B2 | 10/2013 | Bojarski et al. | 623/20.35 |
| 8,561,278 B2 | 10/2013 | Fitz et al. | 29/407.09 |
| 8,562,611 B2 | 10/2013 | Fitz et al. | 606/80 |
| 8,562,618 B2 | 10/2013 | Fitz et al. | 606/88 |
| 8,568,479 B2 | 10/2013 | Fitz et al. | 623/14.12 |
| 8,568,480 B2 | 10/2013 | Fitz et al. | 623/14.12 |
| 8,617,172 B2 | 12/2013 | Fitz et al. | 606/88 |
| 8,617,242 B2 | 12/2013 | Philipp | 623/16.11 |
| 8,623,023 B2 | 1/2014 | Wong et al. | 606/96 |
| 8,634,617 B2 | 1/2014 | Tsougarakis et al. | 382/128 |
| 8,638,998 B2 | 1/2014 | Steines et al. | 382/128 |
| 8,641,716 B2 | 2/2014 | Fitz et al. | 606/80 |
| 8,657,827 B2 | 2/2014 | Fitz et al. | 606/87 |
| 8,682,052 B2 | 3/2014 | Fitz et al. | 382/131 |
| 8,690,945 B2 | 4/2014 | Fitz et al. | 623/16.11 |
| 8,709,089 B2 | 4/2014 | Lang et al. | 623/18.11 |
| 8,735,773 B2 | 5/2014 | Lang | 219/121.72 |
| 8,768,028 B2 | 7/2014 | Lang et al. | 382/131 |
| 8,771,365 B2 | 7/2014 | Bojarski et al. | 623/20.32 |
| 8,882,847 B2 | 11/2014 | Burdulis, Jr. et al. | 623/20.32 |
| 8,906,107 B2 | 12/2014 | Bojarski et al. | 623/20.35 |
| 8,926,706 B2 | 1/2015 | Bojarski et al. | 623/20.14 |
| 8,932,363 B2 | 1/2015 | Tsougarakis et al. | 623/20.14 |
| 8,945,230 B2 | 2/2015 | Lang et al. | 623/20.31 |
| 8,974,539 B2 | 3/2015 | Bojarski et al. | 623/20.14 |
| 9,020,788 B2 | 4/2015 | Lang et al. | 703/6 |
| 9,180,015 B2 | 11/2015 | Fitz et al. | 382/128 |
| 9,186,254 B2 | 11/2015 | Fitz et al. | |
| 9,308,091 B2 | 4/2016 | Lang | |
| 9,320,620 B2 | 4/2016 | Bojarski et al. | 606/79 |
| 9,333,085 B2 | 5/2016 | Fitz et al. | 623/16.11 |
| 9,387,079 B2 | 7/2016 | Bojarski et al. | 623/20.14 |
| 9,387,083 B2 | 7/2016 | Al et al. | |
| 9,495,483 B2 | 11/2016 | Steines et al. | |

(56) References Cited

U.S. PATENT DOCUMENTS

| | | |
|---|---|---|
| 9,603,711 B2 | 3/2017 | Bojarski et al. |
| 9,700,420 B2 | 7/2017 | Fitz et al. |
| 9,737,367 B2 | 8/2017 | Steines et al. |
| 2001/0001120 A1 | 5/2001 | Masini ............... 606/86 |
| 2001/0010023 A1 | 7/2001 | Schwartz et al. ......... 623/23.72 |
| 2001/0039455 A1 | 11/2001 | Simon et al. .............. 623/23.51 |
| 2002/0013626 A1 | 1/2002 | Geistlich et al. ......... 623/23.57 |
| 2002/0016543 A1 | 2/2002 | Tyler ............... 600/410 |
| 2002/0022884 A1 | 2/2002 | Mansmann ............... 623/14.12 |
| 2002/0045940 A1 | 4/2002 | Giannetti et al. ......... 623/11.11 |
| 2002/0052606 A1 | 5/2002 | Bonutti ............... 606/88 |
| 2002/0059049 A1* | 5/2002 | Bradbury et al. .............. 703/11 |
| 2002/0067798 A1 | 6/2002 | Lang ............... 378/54 |
| 2002/0068979 A1 | 6/2002 | Brown et al. ............... 623/20.3 |
| 2002/0072821 A1 | 6/2002 | Baker ............... 700/98 |
| 2002/0082703 A1 | 6/2002 | Repicci ............... 623/20.29 |
| 2002/0087274 A1 | 7/2002 | Alexander et al. ............ 702/19 |
| 2002/0106625 A1 | 8/2002 | Hung et al. ............... 435/1.1 |
| 2002/0111694 A1 | 8/2002 | Ellingsen et al. ......... 623/23.57 |
| 2002/0115647 A1 | 8/2002 | Halvorsen et al. ......... 514/171 |
| 2002/0120274 A1 | 8/2002 | Overaker et al. ............... 606/72 |
| 2002/0120281 A1 | 8/2002 | Overaker ............... 606/151 |
| 2002/0127264 A1 | 9/2002 | Felt et al. ............... 424/423 |
| 2002/0133230 A1 | 9/2002 | Repicci ............... 623/14.12 |
| 2002/0147392 A1 | 10/2002 | Steines et al. ............... 600/407 |
| 2002/0151986 A1 | 10/2002 | Asculai et al. ............... 424/484 |
| 2002/0156150 A1 | 10/2002 | Williams et al. ............... 523/113 |
| 2002/0173852 A1 | 11/2002 | Felt et al. ............... 623/20.32 |
| 2002/0177770 A1 | 11/2002 | Lang et al. ............... 600/410 |
| 2002/0183850 A1 | 12/2002 | Felt et al. ............... 623/20.16 |
| 2003/0015208 A1 | 1/2003 | Lang et al. ............... 128/922 |
| 2003/0031292 A1 | 2/2003 | Lang ............... 378/54 |
| 2003/0035773 A1 | 2/2003 | Totterman et al. ............. 424/9.1 |
| 2003/0045935 A1 | 3/2003 | Angelucci et al. ........ 623/17.11 |
| 2003/0055500 A1 | 3/2003 | Fell et al. ............... 623/14.12 |
| 2003/0055501 A1 | 3/2003 | Fell et al. ............... 623/14.12 |
| 2003/0055502 A1 | 3/2003 | Lang et al. ............... 623/16.11 |
| 2003/0060882 A1 | 3/2003 | Fell et al. ............... 623/14.12 |
| 2003/0060883 A1 | 3/2003 | Fell et al. ............... 623/14.12 |
| 2003/0060884 A1 | 3/2003 | Fell et al. ............... 623/14.12 |
| 2003/0060885 A1 | 3/2003 | Fell et al. ............... 623/14.12 |
| 2003/0063704 A1 | 4/2003 | Lang ............... 378/54 |
| 2003/0069591 A1 | 4/2003 | Carson et al. ............... 606/130 |
| 2003/0100953 A1 | 5/2003 | Rosa et al. ............... 623/20.3 |
| 2003/0158606 A1 | 8/2003 | Coon et al. ............... 623/20.15 |
| 2003/0216669 A1 | 11/2003 | Lang et al. ............... 600/587 |
| 2003/0225457 A1 | 12/2003 | Justin et al. ............... 623/20.14 |
| 2003/0236473 A1 | 12/2003 | Dore et al. ............... 600/587 |
| 2004/0006393 A1 | 1/2004 | Burkinshaw ............ 623/20.3 |
| 2004/0006394 A1 | 1/2004 | Lipman et al. |
| 2004/0062358 A1 | 4/2004 | Lang et al. ............... 378/207 |
| 2004/0081287 A1 | 4/2004 | Lang et al. ............... 378/210 |
| 2004/0098132 A1 | 5/2004 | Andriacchi et al. ....... 623/20.35 |
| 2004/0098133 A1 | 5/2004 | Carignan et al. ......... 623/20.35 |
| 2004/0102851 A1 | 5/2004 | Saladino ............... 623/20.15 |
| 2004/0102852 A1 | 5/2004 | Johnson et al. ............ 623/20.15 |
| 2004/0102866 A1 | 5/2004 | Harris et al. ............ G06F 19/00 |
| 2004/0117015 A1 | 6/2004 | Biscup ............... 623/16.11 |
| 2004/0117023 A1 | 6/2004 | Gerbec et al. ............ 623/18.11 |
| 2004/0122521 A1 | 6/2004 | Lee et al. ............... 623/20.15 |
| 2004/0133276 A1 | 7/2004 | Lang et al. ............... 623/14.12 |
| 2004/0136583 A1 | 7/2004 | Harada et al. ............... 382/131 |
| 2004/0138754 A1 | 7/2004 | Lang et al. ............... 623/20.14 |
| 2004/0138755 A1 | 7/2004 | O'Connor et al. ......... 623/20.32 |
| 2004/0147927 A1 | 7/2004 | Tsougarakis et al. ........ 606/53 |
| 2004/0153079 A1 | 8/2004 | Tsougarakis et al. ........ 606/77 |
| 2004/0153162 A1 | 8/2004 | Sanford et al. ............... 623/20.3 |
| 2004/0153164 A1 | 8/2004 | Sanford et al. ............ 623/20.29 |
| 2004/0167390 A1 | 8/2004 | Alexander et al. ........... 600/410 |
| 2004/0167630 A1 | 8/2004 | Rolston ............... 623/20.14 |
| 2004/0193280 A1 | 9/2004 | Webster et al. ............ 623/20.33 |
| 2004/0204644 A1 | 10/2004 | Tsougarakis et al. ........ 600/410 |
| 2004/0204760 A1 | 10/2004 | Fitz et al. ............... 623/14.12 |
| 2004/0204766 A1 | 10/2004 | Siebel ............... 623/20.31 |
| 2004/0236424 A1 | 11/2004 | Berez et al. ............... 623/14.12 |
| 2005/0010106 A1 | 1/2005 | Lang et al. ............... 600/425 |
| 2005/0015153 A1 | 1/2005 | Goble et al. ............... 623/23.46 |
| 2005/0021042 A1 | 1/2005 | Marnay et al. ............... 606/99 |
| 2005/0033424 A1 | 2/2005 | Fell ............... 623/14.12 |
| 2005/0043807 A1 | 2/2005 | Wood ............... 623/20.14 |
| 2005/0055028 A1 | 3/2005 | Haines ............... 606/79 |
| 2005/0078802 A1 | 4/2005 | Lang et al. ............... 387/207 |
| 2005/0107883 A1 | 5/2005 | Goodfried et al. ........ 623/20.15 |
| 2005/0107884 A1 | 5/2005 | Johnson et al. ............ 623/20.15 |
| 2005/0119664 A1 | 6/2005 | Carignan et al. ............... 606/96 |
| 2005/0125029 A1 | 6/2005 | Bernard et al. ............... 606/205 |
| 2005/0148843 A1 | 7/2005 | Roose ............... A61F 2/46 |
| 2005/0154471 A1 | 7/2005 | Aram et al. ............... 623/20.15 |
| 2005/0171612 A1 | 8/2005 | Rolston ............... 623/20.19 |
| 2005/0197710 A1 | 9/2005 | Naegerl |
| 2005/0197814 A1 | 9/2005 | Aram et al. ............... 703/11 |
| 2005/0203384 A1 | 9/2005 | Sati et al. ............... 600/426 |
| 2005/0216305 A1 | 9/2005 | Funderud ............... 705/2 |
| 2005/0226374 A1 | 10/2005 | Lang et al. ............... 378/54 |
| 2005/0234461 A1 | 10/2005 | Burdulis, Jr. et al. ......... 606/79 |
| 2005/0267584 A1 | 12/2005 | Burdulis et al. ............ 623/20.19 |
| 2005/0278034 A1 | 12/2005 | Johnson et al. ............ 623/20.15 |
| 2006/0009853 A1 | 1/2006 | Justin et al. ............... A61F 2/38 |
| 2006/0015120 A1 | 1/2006 | Richard et al. ............... 606/102 |
| 2006/0058884 A1 | 3/2006 | Aram et al. ............... 623/20.15 |
| 2006/0069318 A1 | 3/2006 | Keaveny et al. ............... 600/300 |
| 2006/0094951 A1 | 5/2006 | Dean et al. ............... 600/407 |
| 2006/0111722 A1 | 5/2006 | Bouadi ............... 606/79 |
| 2006/0111726 A1 | 5/2006 | Felt et al. ............... 606/86 |
| 2006/0129246 A1 | 6/2006 | Steffensmeier ............ A61F 2/38 |
| 2006/0136058 A1 | 6/2006 | Pietrzak ............... 623/13.14 |
| 2006/0149283 A1 | 7/2006 | May et al. ............... 606/96 |
| 2006/0149374 A1 | 7/2006 | Winslow et al. ............ 623/17.11 |
| 2006/0190086 A1 | 8/2006 | Clemow et al. ............ 623/20.15 |
| 2006/0210017 A1 | 9/2006 | Lang ............... 378/54 |
| 2006/0210018 A1 | 9/2006 | Lang ............... 378/54 |
| 2006/0235537 A1 | 10/2006 | Kuczynski et al. |
| 2006/0265078 A1 | 11/2006 | McMinn ............... 623/20.14 |
| 2007/0015995 A1 | 1/2007 | Lang ............... 600/407 |
| 2007/0038223 A1 | 2/2007 | Marquart et al. ............ 606/86 |
| 2007/0047794 A1 | 3/2007 | Lang et al. ............... 378/132 |
| 2007/0067032 A1 | 3/2007 | Felt et al. ............... 623/14.12 |
| 2007/0083266 A1 | 4/2007 | Lang ............... 623/17.11 |
| 2007/0100462 A1 | 5/2007 | Lang et al. ............... 623/20.29 |
| 2007/0118055 A1 | 5/2007 | McCombs ............... 600/587 |
| 2007/0118222 A1 | 5/2007 | Lang ............... 623/17.12 |
| 2007/0118243 A1 | 5/2007 | Schroeder et al. ............ 700/118 |
| 2007/0156171 A1 | 7/2007 | Lang et al. ............... 606/205 |
| 2007/0190108 A1 | 8/2007 | Datta et al. ............... 424/423 |
| 2007/0198022 A1 | 8/2007 | Lang et al. ............... 606/88 |
| 2007/0203430 A1 | 8/2007 | Lang et al. ............... 600/587 |
| 2007/0226986 A1 | 10/2007 | Park et al. ............... 29/592 |
| 2007/0233156 A1 | 10/2007 | Metzger ............... 606/130 |
| 2007/0233269 A1 | 10/2007 | Steines et al. ............... 623/20.21 |
| 2007/0239165 A1 | 10/2007 | Amirouche ............... 606/86 |
| 2007/0250169 A1 | 10/2007 | Lang ............... 623/17.12 |
| 2007/0255288 A1 | 11/2007 | Mahfouz et al. ............ 606/102 |
| 2007/0274444 A1 | 11/2007 | Lang ............... 378/54 |
| 2007/0276224 A1 | 11/2007 | Lang et al. ............... 600/410 |
| 2007/0276501 A1 | 11/2007 | Betz et al. ............... 623/17.16 |
| 2007/0282451 A1 | 12/2007 | Metzger et al. ............ 623/20.28 |
| 2008/0009950 A1 | 1/2008 | Richardson ............... 623/20.29 |
| 2008/0015433 A1 | 1/2008 | Alexander et al. ............ 600/427 |
| 2008/0025463 A1 | 1/2008 | Lang ............... 378/54 |
| 2008/0147072 A1 | 1/2008 | Park et al. ............... 606/87 |
| 2008/0031412 A1 | 2/2008 | Lang et al. ............... 378/54 |
| 2008/0058613 A1 | 3/2008 | Lang et al. ............... 600/300 |
| 2008/0058945 A1 | 3/2008 | Hajaj et al. ............... 623/20.14 |
| 2008/0119938 A1 | 5/2008 | Oh ............... 623/20.14 |
| 2008/0119940 A1 | 5/2008 | Otto et al. ............... 623/20.31 |
| 2008/0133020 A1 | 6/2008 | Blackwell et al. |
| 2008/0140212 A1 | 6/2008 | Metzger et al. ............ 623/20.31 |
| 2008/0170659 A1 | 7/2008 | Lang et al. ............... 378/56 |
| 2008/0172125 A1 | 7/2008 | Ek ............... 623/14.12 |
| 2008/0195108 A1 | 8/2008 | Bhatnagar et al. ............ 606/87 |
| 2008/0195216 A1 | 8/2008 | Philipp ............... 623/18.11 |
| 2008/0208348 A1 | 8/2008 | Fitz ............... 623/19.14 |
| 2008/0215059 A1 | 9/2008 | Carignan et al. ............... 606/96 |
| 2008/0219412 A1 | 9/2008 | Lang ............... 378/207 |

(56) References Cited

U.S. PATENT DOCUMENTS

| | | | |
|---|---|---|---|
| 2008/0243127 A1 | 10/2008 | Lang et al. ............... 606/87 |
| 2008/0255445 A1 | 10/2008 | Neubauer et al. ........... 600/416 |
| 2008/0257363 A1 | 10/2008 | Schoenefeld et al. ........ 128/898 |
| 2008/0262624 A1 | 10/2008 | White et al. ............... 623/20.32 |
| 2008/0269596 A1 | 10/2008 | Revie et al. |
| 2008/0275452 A1 | 11/2008 | Lang et al. ............... 606/88 |
| 2008/0281328 A1 | 11/2008 | Lang et al. ............... 606/87 |
| 2008/0281329 A1 | 11/2008 | Fitz et al. ............... 623/17.16 |
| 2008/0281426 A1 | 11/2008 | Fitz et al. ............... 623/17.16 |
| 2008/0319948 A1 | 12/2008 | Berg et al. ............... 606/102 |
| 2009/0062925 A1 | 3/2009 | Samuelson ............... 623/23.12 |
| 2009/0076371 A1 | 3/2009 | Lang et al. ............... 600/407 |
| 2009/0076508 A1 | 3/2009 | Weinans et al. ............ 606/62 |
| 2009/0118830 A1 | 5/2009 | Fell ............... 623/14.12 |
| 2009/0131941 A1 | 5/2009 | Park et al. ............... 606/87 |
| 2009/0149977 A1 | 6/2009 | Schendel ............... 700/98 |
| 2009/0151736 A1 | 6/2009 | Belcher et al. ............ 128/898 |
| 2009/0222103 A1 | 9/2009 | Fitz et al. ............... 623/18.11 |
| 2009/0226068 A1 | 9/2009 | Fitz et al. ............... 382/131 |
| 2009/0228111 A1 | 9/2009 | Otto ............... 623/20.19 |
| 2009/0228113 A1 | 9/2009 | Lang et al. ............... 623/20.32 |
| 2009/0270868 A1 | 10/2009 | Park et al. ............... 606/87 |
| 2009/0276045 A1 | 11/2009 | Lang ............... 623/14.12 |
| 2009/0306676 A1 | 12/2009 | Lang et al. ............... 606/102 |
| 2009/0306785 A1 | 12/2009 | Farrar et al. |
| 2009/0312805 A1 | 12/2009 | Lang et al. ............... 606/86 R |
| 2009/0326665 A1 | 12/2009 | Wyss et al. |
| 2009/0326666 A1 | 12/2009 | Wyss et al. ............... 623/20.29 |
| 2010/0042105 A1 | 2/2010 | Park et al. ............... 606/87 |
| 2010/0054572 A1 | 3/2010 | Tsougarakis et al. ........ 382/131 |
| 2010/0217270 A1 | 8/2010 | Polinski et al. ............ 606/87 |
| 2010/0274534 A1 | 10/2010 | Steines et al. ............ 703/1 |
| 2010/0292963 A1 | 11/2010 | Schroeder ............... 703/1 |
| 2010/0303313 A1 | 12/2010 | Lang et al. ............... 382/128 |
| 2010/0303317 A1 | 12/2010 | Tsougarakis et al. ........ 382/128 |
| 2010/0303324 A1 | 12/2010 | Lang et al. ............... 382/128 |
| 2010/0305575 A1 | 12/2010 | Wilkinson et al. ............ 606/88 |
| 2010/0305708 A1 | 12/2010 | Lang et al. ............... 623/20.18 |
| 2010/0305907 A1 | 12/2010 | Fitz et al. ............... 703/1 |
| 2010/0329530 A1 | 12/2010 | Lang et al. ............... 382/131 |
| 2010/0331991 A1 | 12/2010 | Wilkinson et al. ........... 623/20.32 |
| 2010/0332194 A1 | 12/2010 | McGuan et al. ............... 703/1 |
| 2011/0022179 A1 | 1/2011 | Andriacchi et al. ........ 623/20.18 |
| 2011/0029091 A1 | 2/2011 | Bojarski et al. ............ 623/20.32 |
| 2011/0029093 A1 | 2/2011 | Bojarski et al. ............ 623/20.35 |
| 2011/0046735 A1 | 2/2011 | Metzger et al. ............ 623/14.12 |
| 2011/0066245 A1 | 3/2011 | Lang et al. ............... 623/18.11 |
| 2011/0071645 A1 | 3/2011 | Bojarski et al. ............ 623/20.35 |
| 2011/0071802 A1 | 3/2011 | Bojarski et al. ............... 703/1 |
| 2011/0087332 A1 | 4/2011 | Bojarski et al. ............ 623/20.32 |
| 2011/0087465 A1 | 4/2011 | Mahfouz ............... 703/1 |
| 2011/0092804 A1 | 4/2011 | Schoenefeld et al. ........ 600/416 |
| 2011/0093108 A1 | 4/2011 | Ashby et al. ............... 700/103 |
| 2011/0125009 A1 | 5/2011 | Lang et al. ............... 600/425 |
| 2011/0144760 A1 | 6/2011 | Wong et al. ............... 623/20.14 |
| 2011/0184526 A1 | 7/2011 | White et al. ............... 623/20.32 |
| 2011/0218635 A1 | 9/2011 | Amis et al. ............... A61F 2/38 |
| 2011/0264097 A1 | 10/2011 | Hodorek et al. ............... 606/88 |
| 2011/0266265 A1 | 11/2011 | Lang ............... 219/121.72 |
| 2011/0288669 A1 | 11/2011 | Sanford et al. ............... 700/103 |
| 2011/0295378 A1 | 12/2011 | Bojarski et al. ............ 623/20.35 |
| 2011/0305379 A1 | 12/2011 | Mahfouz ............... 382/131 |
| 2012/0022659 A1 | 1/2012 | Wentorf ............... 623/20.32 |
| 2012/0093377 A1 | 4/2012 | Tsougarakis et al. ........ 382/128 |
| 2012/0116203 A1 | 5/2012 | Vancraen et al. ............ 600/407 |
| 2012/0191205 A1 | 7/2012 | Bojarski et al. ............ 623/20.32 |
| 2012/0191420 A1 | 7/2012 | Bojarski et al. ............... 703/1 |
| 2012/0197408 A1 | 8/2012 | Lang et al. ............... 623/18.11 |
| 2012/0201440 A1 | 8/2012 | Steines et al. ............ 382/131 |
| 2012/0209394 A1 | 8/2012 | Bojarski et al. ............ 623/20.32 |
| 2012/0232669 A1 | 9/2012 | Bojarski et al. ............ 623/20.3 |
| 2012/0232670 A1 | 9/2012 | Bojarski et al. ............ 623/20.35 |
| 2012/0232671 A1 | 9/2012 | Bojarski et al. ............ 623/20.35 |
| 2012/0265496 A1 | 10/2012 | Mahfouz ............... G06F 17/50 |
| 2012/0310362 A1 | 12/2012 | Li et al. |
| 2013/0006598 A1 | 1/2013 | Alexander et al. ............ 703/11 |
| 2013/0035766 A1 | 2/2013 | Meridew ............... 623/22.21 |
| 2013/0071828 A1 | 3/2013 | Lang et al. ............. G09B 23/30 |
| 2013/0079781 A1 | 3/2013 | Fitz et al. ............ A61B 17/1675 |
| 2013/0079876 A1 | 3/2013 | Fitz et al. ............ A61F 2/30756 |
| 2013/0081247 A1 | 4/2013 | Fitz et al. ............... B23Q 17/00 |
| 2013/0103363 A1 | 4/2013 | Lang et al. ............... 703/1 |
| 2013/0110471 A1 | 5/2013 | Lang et al. ............... 703/1 |
| 2013/0144570 A1 | 6/2013 | Axelson, Jr. et al. ............ 703/1 |
| 2013/0158671 A1 | 6/2013 | Uthgenannt et al. ....... 623/20.35 |
| 2013/0165939 A1 | 6/2013 | Ries et al. ............... 606/88 |
| 2013/0197870 A1 | 8/2013 | Steines et al. ........... G06F 17/50 |
| 2013/0199259 A1 | 8/2013 | Smith ............... 72/362 |
| 2013/0203031 A1 | 8/2013 | Mckinnon et al. ............ 434/262 |
| 2013/0211531 A1 | 8/2013 | Steines et al. ............ A61F 2/38 |
| 2013/0245803 A1 | 9/2013 | Lang ............... G06F 17/50 |
| 2013/0297031 A1 | 11/2013 | Hafez ............... 623/20.14 |
| 2014/0005792 A1 | 1/2014 | Lang et al. ............... 623/20.32 |
| 2014/0029814 A1 | 1/2014 | Fitz et al. ............... 382/128 |
| 2014/0039631 A1 | 2/2014 | Bojarski et al. ............ 623/18.11 |
| 2014/0086780 A1 | 3/2014 | Miller et al. ............... 419/1 |
| 2014/0109384 A1 | 4/2014 | Lang ............... 29/557 |
| 2014/0115872 A1 | 5/2014 | Steines et al. ............... 29/592 |
| 2014/0136154 A1 | 5/2014 | Bojarski et al. ............... 703/1 |
| 2014/0153798 A1 | 6/2014 | Tsougarakis et al. ........ 382/128 |
| 2014/0172111 A1 | 6/2014 | Lang et al. ............... 623/20.32 |
| 2014/0194996 A1 | 7/2014 | Bojarski et al. ............ 623/20.35 |
| 2014/0207243 A1 | 7/2014 | Fitz et al. ............... 623/20.16 |
| 2014/0208578 A1 | 7/2014 | Linderman et al. ............ 29/592 |
| 2014/0222157 A1 | 8/2014 | Al et al. |
| 2014/0222390 A1 | 8/2014 | Asseln et al. |
| 2014/0228860 A1 | 8/2014 | Steines et al. |
| 2014/0257508 A1 | 9/2014 | Bojarski et al. |
| 2015/0081029 A1 | 3/2015 | Bojarski et al. |
| 2015/0157461 A1 | 6/2015 | Burdulis, Jr. et al. |
| 2015/0216615 A1 | 8/2015 | Tsougarakis et al. |
| 2016/0038293 A1 | 2/2016 | Slamin et al. |
| 2016/0045317 A1 | 2/2016 | Lang et al. |
| 2016/0143744 A1 | 5/2016 | Bojarski et al. |
| 2016/0317312 A1 | 11/2016 | Bojarski et al. |
| 2016/0331467 A1 | 11/2016 | Slamin et al. |
| 2017/0056183 A1 | 3/2017 | Steines et al. |

FOREIGN PATENT DOCUMENTS

| | | | |
|---|---|---|---|
| CN | 1480111 A | 3/2004 | ............... A61F 2/30 |
| CN | 101288597 | 10/2008 | ............... A61B 17/56 |
| DE | 2306552 | 8/1974 | ............... A61F 1/00 |
| DE | 3516743 | 11/1986 | ............... A61F 2/36 |
| DE | 8909091 | 9/1987 | ............... A61F 2/35 |
| DE | 44 34 539 | 4/1996 | ............... A61F 2/38 |
| DE | 19803673 | 8/1999 | ............... A61F 27/54 |
| DE | 19926083 | 12/2000 | ............... A61L 27/54 |
| DE | 10135771 | 2/2003 | ............... A61B 17/70 |
| EP | 0528080 | 2/1993 | ............... A61F 2/30 |
| EP | 0600806 | 6/1994 | ............... A61L 25/00 |
| EP | 0672397 | 9/1995 | ............... A61F 2/38 |
| EP | 0681817 A1 | 11/1995 | ............... A61F 2/38 |
| EP | 0 704 193 | 4/1996 | ............... A61F 2/30 |
| EP | 0626156 | 7/1997 | ............... A61F 2/38 |
| EP | 0613380 | 12/1999 | ............... A61L 27/00 |
| EP | 1074229 | 2/2001 | ............... A61F 2/38 |
| EP | 1077253 | 2/2001 | ............... C12N 5/00 |
| EP | 1120087 | 8/2001 | ............... A61B 17/06 |
| EP | 1129675 | 9/2001 | ............... A61F 2/38 |
| EP | 0732091 | 12/2001 | ............... A61F 2/38 |
| EP | 0896825 | 7/2002 | ............... A61L 27/00 |
| EP | 0814731 | 8/2002 | ............... A61F 2/30 |
| EP | 1234552 | 8/2002 | ............... A61F 2/30 |
| EP | 1234555 | 8/2002 | ............... A61F 2/30 |
| EP | 0809987 | 10/2002 | ............... A61F 2/38 |
| EP | 0833620 | 10/2002 | ............... A61K 9/22 |
| EP | 1327423 | 7/2003 | ............... A61F 2/38 |
| EP | 1329205 | 7/2003 | ............... A61F 2/38 |
| EP | 0530804 | 6/2004 | ............... A61L 25/00 |
| EP | 1437101 | 7/2004 | ............... A61F 2/08 |
| EP | 1070487 | 9/2005 | ............... A61F 2/08 |
| EP | 1886640 | 2/2008 | ............... A61B 19/00 |
| EP | 2324799 | 5/2011 | ............... A61F 2/38 |

(56) References Cited

FOREIGN PATENT DOCUMENTS

| | | | |
|---|---|---|---|
| EP | 2173260 | 1/2012 | A61B 17/15 |
| FR | 2589720 | 11/1985 | A61F 2/38 |
| FR | 2740326 | 4/1997 | A61F 2/38 |
| GB | 1451283 | 9/1976 | A61F 1/24 |
| GB | 2291355 | 1/1996 | A61F 2/38 |
| GB | 2304051 | 3/1997 | A61F 2/38 |
| GB | 2348373 | 10/2000 | A61F 2/38 |
| JP | 56-083343 | 7/1981 | A61F 1/03 |
| JP | 61-247448 | 11/1986 | A61F 2/30 |
| JP | 1-249049 | 10/1989 | A61F 2/38 |
| JP | 5-503644 A | 6/1993 | |
| JP | 05-184612 | 7/1993 | A61F 2/30 |
| JP | 7-236648 | 9/1995 | A61F 2/28 |
| JP | 8-173465 | 7/1996 | A61F 2/38 |
| JP | 8-506042 A | 7/1996 | A61F 2/38 |
| JP | 9-206322 | 8/1997 | A61F 2/36 |
| JP | 11-19104 | 1/1999 | A61F 2/28 |
| JP | 11-276510 | 10/1999 | A61F 2/28 |
| JP | 2001-502565 A | 2/2001 | A61F 2/32 |
| JP | 2002-85435 A | 3/2002 | A61F 2/28 |
| JP | 2007-521881 | 8/2007 | A61F 2/44 |
| WO | WO 87/02882 | 5/1987 | A61F 2/38 |
| WO | WO 90/009769 | 9/1990 | A61F 2/28 |
| WO | WO 92/03108 | 3/1992 | A61F 2/38 |
| WO | WO 93/004710 | 3/1993 | A61L 25/00 |
| WO | WO 93/009819 | 5/1993 | A61L 27/00 |
| WO | WO 93/025157 | 12/1993 | A61B 17/56 |
| WO | WO 95/027450 | 10/1995 | A61F 2/38 |
| WO | WO 95/028688 | 10/1995 | G06T 15/00 |
| WO | WO 95/030390 | 11/1995 | A61F 2/38 |
| WO | WO 95/032623 | 12/1995 | A01N 1/02 |
| WO | WO 96/024302 | 8/1996 | A61B 17/90 |
| WO | WO 97/025942 | 7/1997 | A61F 2/32 |
| WO | WO 97/027885 | 8/1997 | A61L 27/00 |
| WO | WO 97/029703 | 8/1997 | A61B 17/56 |
| WO | WO 97/038676 | 10/1997 | A61K 9/10 |
| WO | WO 97/046665 | 12/1997 | C12N 5/06 |
| WO | WO 98/008469 | 3/1998 | A61F 2/30 |
| WO | WO 98/012994 | 4/1998 | A61F 2/28 |
| WO | WO 98/14128 A1 | 4/1998 | A61B 17/56 |
| WO | WO 98/20816 | 5/1998 | A61F 2/38 |
| WO | WO 98/030617 | 7/1998 | C08G 63/12 |
| WO | WO 98/052498 | 11/1998 | A61F 2/28 |
| WO | WO 99/002654 | 1/1999 | C12N 5/00 |
| WO | WO 99/008598 | 2/1999 | A61B 8/00 |
| WO | WO 99/008728 | 2/1999 | A61L 27/00 |
| WO | WO 99/042061 | 8/1999 | A61F 2/38 |
| WO | WO 99/047186 | 9/1999 | A61L 27/00 |
| WO | WO 99/051719 | 10/1999 | C12M 3/00 |
| WO | WO 00/009179 | 2/2000 | A61L 25/00 |
| WO | WO 00/015153 | 3/2000 | A61F 2/38 |
| WO | WO 00/19911 | 4/2000 | A61B 17/02 |
| WO | WO 00/035346 | 6/2000 | A61B 5/11 |
| WO | WO 00/048550 | 8/2000 | |
| WO | WO 00/059411 | 10/2000 | A61F 2/38 |
| WO | WO 00/068749 | 11/2000 | G05B 19/4099 |
| WO | WO 00/074554 | 12/2000 | |
| WO | WO 00/074741 | 12/2000 | A61L 27/00 |
| WO | WO 00/76428 | 12/2000 | A61F 2/38 |
| WO | WO 01/010356 | 2/2001 | A61F 2/46 |
| WO | WO 01/017463 | 3/2001 | A61F 2/30 |
| WO | WO 01/019254 | 3/2001 | A61B 17/00 |
| WO | WO 01/035968 | 5/2001 | A61K 35/00 |
| WO | WO 01/045764 | 6/2001 | A61L 27/36 |
| WO | WO 01/66021 A1 | 9/2001 | A61B 17/14 |
| WO | WO 01/068800 | 9/2001 | C12M 3/00 |
| WO | WO 01/070142 | 9/2001 | A61F 2/38 |
| WO | WO 01/077988 | 10/2001 | G06F 19/00 |
| WO | WO 01/082677 | 11/2001 | |
| WO | WO 01/091672 | 12/2001 | A61F 2/36 |
| WO | WO 02/02021 | 1/2002 | A61B 17/56 |
| WO | WO 02/09623 | 2/2002 | A61F 2/38 |
| WO | WO 02/022013 | 3/2002 | A61B 5/55 |
| WO | WO 02/022014 | 3/2002 | A61B 5/55 |
| WO | WO 02/023483 | 3/2002 | A61B 5/55 |
| WO | WO 02/034310 | 5/2002 | A61L 31/04 |
| WO | WO 02/036147 | 5/2002 | A61K 31/04 |
| WO | WO 02/37423 | 5/2002 | G06T 17/00 |
| WO | WO 02/061688 | 8/2002 | G06T 17/00 |
| WO | WO 02/096268 | 12/2002 | |
| WO | WO 03/007788 | 1/2003 | |
| WO | WO 03/013373 | 2/2003 | A61B 17/17 |
| WO | WO 03/037192 | 5/2003 | A61B 17/15 |
| WO | WO 03/047470 | 6/2003 | A61F 2/34 |
| WO | WO 03/051210 | 6/2003 | A61B 17/58 |
| WO | WO 03/061522 | 7/2003 | |
| WO | WO 03/099106 | 12/2003 | |
| WO | WO 04/006811 | 1/2004 | A61F 2/46 |
| WO | WO 04/032806 | 4/2004 | A61F 2/30 |
| WO | WO 04/043305 | 5/2004 | A61F 2/30 |
| WO | WO 04/049981 | 6/2004 | A61F 2/46 |
| WO | WO 04/051301 | 6/2004 | G01R 33/56 |
| WO | WO 04/073550 | 9/2004 | |
| WO | WO 05/002473 | 1/2005 | A61F 2/38 |
| WO | WO 05/016175 | 2/2005 | |
| WO | WO 05/020850 | 3/2005 | |
| WO | WO 05/051239 | 6/2005 | A61F 2/08 |
| WO | WO 05/051240 | 6/2005 | A61F 2/08 |
| WO | WO 05/067521 | 7/2005 | |
| WO | WO 05/076974 | 8/2005 | |
| WO | WO 06/012370 | 2/2006 | B65D 45/04 |
| WO | WO 06/058057 | 6/2006 | A61F 2/38 |
| WO | WO 06/060795 | 6/2006 | A61B 17/17 |
| WO | WO 06/065774 | 6/2006 | A61F 2/44 |
| WO | WO 06/092600 | 9/2006 | A61B 19/00 |
| WO | WO 07/041375 | 4/2007 | A61F 2/38 |
| WO | WO 07/062079 | 5/2007 | A61F 2/30 |
| WO | WO 07/092841 | 8/2007 | A61B 17/15 |
| WO | WO 07/106172 | 9/2007 | A61F 2/38 |
| WO | WO 07/109641 | 9/2007 | A61F 2/30 |
| WO | WO 08/021494 | 2/2008 | G06F 19/00 |
| WO | WO 08/055161 | 5/2008 | A61F 2/44 |
| WO | WO 08/101090 | 8/2008 | A61F 2/38 |
| WO | WO 08/117028 | 10/2008 | A61B 17/15 |
| WO | WO 08/157412 | 12/2008 | A61B 17/17 |
| WO | WO 09/068892 | 6/2009 | A61C 9/00 |
| WO | WO 09/105495 A1 | 8/2009 | A61F 2/38 |
| WO | WO 09/140294 | 11/2009 | A61F 2/30 |
| WO | WO 10/099231 | 9/2010 | A61B 2/38 |
| WO | WO 10/099353 | 9/2010 | A61F 2/30 |
| WO | WO 10/099359 | 9/2010 | A61F 2/00 |
| WO | WO 10/140036 | 12/2010 | A61F 2/38 |
| WO | WO 10/151564 | 12/2010 | A61F 2/38 |
| WO | WO 11/028624 | 3/2011 | A61F 2/38 |
| WO | WO 11/056995 | 5/2011 | A61F 2/38 |
| WO | WO 11/072235 | 6/2011 | A61F 2/38 |
| WO | WO 11/075697 | 6/2011 | A61F 2/38 |
| WO | WO 11/094540 A2 | 8/2011 | A61F 2/38 |
| WO | WO 11/101474 | 8/2011 | G06F 19/00 |
| WO | WO 12/021894 A2 | 2/2012 | A61F 2/46 |
| WO | WO 12/027150 | 3/2012 | G06F 19/00 |
| WO | WO 12/027185 | 3/2012 | G06T 17/00 |
| WO | WO 12/112694 | 8/2012 | A61B 6/00 |
| WO | WO 12/112698 | 8/2012 | A61F 2/30 |
| WO | WO 12/112701 | 8/2012 | A61F 2/30 |
| WO | WO 12/112702 | 8/2012 | A61F 2/30 |
| WO | WO 13/020026 | 2/2013 | A61F 2/30 |
| WO | WO 13/025814 | 2/2013 | A61F 2/38 |
| WO | WO 13/056036 | 4/2013 | A61F 2/38 |
| WO | WO 13/131066 | 9/2013 | A61F 2/38 |
| WO | WO 13/152341 | 10/2013 | A61F 2/38 |
| WO | WO 14/035991 | 3/2014 | A61B 17/56 |
| WO | WO-2014145267 A1 | 9/2014 | |
| WO | WO-2014152533 A1 | 9/2014 | |

OTHER PUBLICATIONS

Adam et al., "MR Imaging of the Knee: Three-Dimensional Volume Imaging Combined with Fast Processing," J. Compt. Asst. Tomogr., 13(6): 984-988 (1989).

Adams et al., "Quantitative Imaging of Osteoarthritis," Semin Arthritis Rheum, 20(6) Suppl. 2: 26-39 (Jun. 1991).

(56) References Cited

OTHER PUBLICATIONS

Ahmad et al., "Biomechanical and Topographic Considerations for Autologous Osteochondral Grafting in the Knee," Am J Sports Med, 29(2): 201-206 (Mar.-Apr. 2001).
Alexander, "Estimating the motion of bones from markers on the skin," University of Illinois at Chicago (Doctoral Dissertation) (1998).
Alexander et al., "Correcting for deformation in skin-based marker systems," Proceedings of the 3rd Annual Gait and Clinical Movement Analysis Meeting, San Diego, CA (1998).
Alexander et al., "Internal to external correspondence in the analysis of lower limb bone motion," Proceedings of the 1999 ASME Summer Bioengineering Conference, Big Sky, Montana (1999).
Alexander et al., "State estimation theory in human movement analysis," Proceedings of the ASME International Mechanical Engineering Congress (1998).
Alexander et al. "Optimization techniques for skin deformation correction," International Symposium on 3-D Human Movement Conference, Chattanooga, TN, (1998).
Alexander et al., "Dynamic Functional Imaging of the Musculoskeletal System," ASME Winter International Congress and Exposition, Nashville, TN (1999).
Allen et al., "Late degenerative changes after meniscectomy 5 factors affecting the knee after operations," J Bone Joint Surg 66B: 666-671 (1984).
Alley et al., "Ultrafast contrast-enhanced three dimensional MR Aagiography: State of the art," Radiographics 18: 273-285 (1998).
Andersson et al., "MacIntosh Arthroplasty in Rheumatoid Arthritis," Acta. Orthrop. Scand. 45(2):245-259 (1974).
Andriacchi, "Dynamics of knee Malalignment," Orthop Clin North Am 25: 395-403 (1994).
Andriacchi, et al., "A point cluster method for in vivo motion analysis: Applied to a study of knee kinematics," J. Biomech Eng 120(12): 743-749 (1998).
Andriacchi, et al., "Methods for evaluating the progression of Osterarthiritis," Journal of Rehabilitation Research and Development 37(2): 163-170 (2000).
Andriacchi et al., "Gait analysis as a tool to assess joint kinetics biomechanics of normal and pathological human articulating joints," Nijhoff, Series E 93: 83-102 (1985).
Andriacchi et al., "In vivo measurement of six-degrees-of-freedom knee movement during functional testing," Transactions of the Orthopedic Research Society 698 (1995).
Argenson et al., "Is There a Place for Patellofemoral Arthroplasty?," Clinical Orthopaedics and Related Research No. 321, pp. 162-167 (1995).
Aro et al., "Clinical Use of Bone Allografts," Ann Med 25:403-412 (1993).
Bashir, "Validation of Gadolinium-Enhanced MRI of FAF Measurement in Human Cartilage," Intl. Soc. Mag. Resonance Med. (1998).
Beaulieu et al., "Glenohumeral relationships during physiological shoulder motion and stress testing: Initial experience with open MRI and active Scan-25 plane registration," Radiology (1999).
Beaulieu et al., "Dynamic imaging of glenohumeral instability with open MRI," Int. Society for Magnetic Resonance in Medicine Sydney, Australia (1998).
Beckmann et al., "Noninvasive 3D MR Microscopy as Tool in Pharmacological Research: Application to a Model of Rheumatoid Arthritis," Magn Reson Imaging 13(7): 1013-1017 (1995).
Billet, Philippe, French Version—"Gliding Knee Prostheses—Analysis of Mechanical Failures", Thesis, Medical School of Marseilles, 1982, 64 pages.
Billet, Philippe, Translated Version—"Gliding Knee Prostheses—Analysis of Mechanical Failures", Thesis, Medical School of Marseilles, 1982, 93 pages.
Blazina et al., "Patellofemoral replacement: Utilizing a customized femoral groove replacement," 5(1)53-55 (1990).
Blum et al., "Knee Arthroplasty in Patients with Rheumatoid Arthritis," Ann. Rheum. Dis. 33 (1): 1-11 (1974).
Bobic, "Arthroscopic osteochondral autogaft transplantation in anterior cruciate ligament reconstruction: a preliminary clinical study," Knee Surg Sports Traumatol Arthrosc 3(4): 262-264 (1996).
Boe et al., "Arthroscopic partial meniscectomy in patients aged over 50," J. Bone Joint Surg 68B: 707 (1986).
Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).
Borthakur et al., "In Vivo Triple Quantum Filtered Sodium MRI of Human Articular Cartilage," Proc. Intl. Soc. Mag. Resonance Med., 7:549 (1999).
Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).
Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).
Bregler et al., "Recovering non-rigid 3D shape from image streams," Proc. IEEE Conference on Computer Vision and Pattern Recognition (Jun. 2000).
Brett et al., "Quantitative Analysis of Biomedical Images," Univ. of Manchester, Zeneca Pharmaceuticals, IBM UK, http://www.wiau.man.ac.uk/~ads/imv (1998).
Brittberg et al., "A critical analysis of cartilage repair," Acta Orthop Scand 68(2): 186-191 (1997).
Brittberg et al., "Treatment of deep cartilage defects in the knee with autologous chondrocyte transplantation," N Engl J Med 331(14): 889-895 (1994).
Broderick et al., "Severity of articular cartilage abnormality in patients with osteoarthritis: evaluation with fast spin-echo MR vs. arthroscopy," ARJ 162: 99-103 (1994).
Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).
Burgkart et al., "Magnetic Resonance Imaging-Based Assessment of Cartilage Loss in Severe Osteoarthritis," Arth Rheum; 44(9): 2072-2077 (Sep. 2001).
Butterworth et al. "A T1O2 Dielectric-Filled Toroidal Resonator," Depts of Biomedical Engineering, Medicine, Neurology, & Center for Nuclear Imaging Research, U. of Alabama at Birmingham, USA, 1 Page (1999).
Butts et al., "Real-Time MR imaging of joint motion on an open MR imaging scanner," Radiological Society of North America, 83rd Scientific Assembly and Annual Meeting, Chicago, IL (1997).
Cameron, et al., "Review of a Failed Knee Replacement and Some Observations on the Design of a Knee Resurfacing Prosthesis," Arch. Orthop Trauma Surg. 97(2):87-89 (1980).
CAOS, "MIS meets CAOS Spring 2005 Symposium Schedule", *CAOS Spring 2005 Symposium*, pp. 1-9, May 19, 2005.
Carano et al. "Estimation of Erosive Changes in Rheumatoid Arthritis by Temporal Multispectral Analysis," Proc. Intl. Soc. Mag. Resonance Med., 7:408 (1999).
Carr et al., "Surface Interpolation with Radial Basis Functions for Medical Imaging," IEEE Transactions on Medical Imaging, IEEE, Inc. New York, vol. 16, pp. 96-107 (Feb. 1997).
Castriota-Scanderbeg et al., "Precision of Sonographic Measurement of Articular Cartilage: Inter- and Intraobserver Analysis," Skeletal Radiol 25: 545-549 (1996).
Chan et al., "Osteoarthritis of the Knee: Comparison of Radiography, CT and MR Imaging to Asses Extent and Severity," AJR Am J Roentgenol 157(4): 799-806 (1991).
Chelule et al., "Patient-Specific Template to Preserve Bone Stock in Total Knee Replacement: Preliminary Results", *15th Annual ISTA Symposium*, Sep. 2002, 1 page.
Clarke et al., "Human Hip Joint Geometry and Hemiarthroplasty Selection," The Hip. C.V. Mosby, St. Louis 63-89 (1975).
Clary et al., "Experience with the MacIntosh Knee Prosthesis," South Med. J. 65(3):265-272 (1972).

(56) References Cited

OTHER PUBLICATIONS

Cohen et al., "Knee cartilage topography, thickness, and contact areas from MRI: in-vitro calibration and in-vivo measurements," Osteoarthritis and Cartilage 7: 95-109 (1999).
Conaty, et al., "Surgery of the Hip and Knee in Patients with Rheumatoid Arthritis," J. Bone Joint Surg. Am. 55(2):301-314 (1973).
Creamer et al., "Quantitative Magnetic Resonance Imaging of the Knee: A Method of Measuring Response to Intra-Articular Treatments," Ann Rheum Dis. 378-381 (1997).
Daniel et al., "Breast cancer-gadolinium-enhanced MR imaging with a 0.5T open imager and three-point Dixon technique," Radiology 207(1): 183-190 (1998).
Dardzinski et al., "Entropy Mapping of Articular Cartilage", ISMRM Seventh Scientific Meeting, Philadelphia, PA (1999) T. 41, V. II.
Dardzinski et al. "T1-T2 Comparison in Adult Articular Cartilage," ISMRM Seventh Scientific Meeting, Philadelphia, PA (May 22-28, 1999).
De Winter et al., "The Richards Type II Patellofemoral Arthroplasty", Acta Orthop Scand 2001; 72 (5): 487-490.
Disler, "Fat-suppressed three-dimensional spoiled gradient-recalled MR imaging: assessment of articular and physeal hyaline cartilage," AJR 169: 1117-1123 (1997).
Disler et al., "Fat-suppressed three-dimensional spoiled gradient-echo MR imaging of hyaline cartilage defects in the knee: comparison with standard MR imaging and arthroscopy," AJR 167: 127-132 (1996).
Disler et al., "Detection of knee hyaline cartilage defects using fat-suppressed three-dimensional spoiled gradient-echo MR imaging: comparison with standard MR imaging and correlation with arthroscopy," AJR 165: 377-382 (1995).
Doherty et al., Osteoarthritis, Oxford Textbook of Theumatology, Oxford University Press 959-983 (1993).
Dougados et al., "Longitudinal radiologic evaluation of osteoarthritis of the knee," J Theumatol 19: 378-384 (1992).
Du et al., "Vessel enhancement filtering in three-dimensional MR angiography," J. Magn Res Imaging 5: 151-157 (1995).
Du et al., "Reduction of partial-volume artifacts with zero filled interpolation in three-dimensional MR Angiography," J Magn Res Imaging 4: 733-741 (1994).
Dufour et al., "A Technique for the Dynamical Evaluation of the Acromiohumeral Distance of the Shoulder in the Seated Position under Open-field MRI," Proc. Intl. Soc. Mag. Resonance Med., 7:406 (1999).
Dumoulin et al., "Real-time position monitoring of invasive devises using magnetic resonance," Magn Reson Med 29: 411-5 (1993).
Dupuy et al., "Quantification of Articular Cartilage in the Knee with Three-Dimensional MR Imaging," Acad Radiol 3: 919-924 (1996).
Eckstein et al., "Determination of Knee Joint Cartilage Thickness Using Three-Dimensional Magnetic Resonance Chondro-Crassometry (3D MR-CCM)," Magn. Reson. Med. 36(2):256-265, (1996).
Eckstein et al., "Effect of Gradient and Section Orientation on Quantitative Analyses of Knee Joint Cartilage," Journal of Magnetic Resonance Imaging 11: 161-167 (2000).
Eckstein et al., "Effect of Physical Exercise on Cartilage Volume and Thickness In Vivo: An MR Imaging Study," Radiology 207: 243-248 (1998).
Eckstein et al., "Functional Analysis of Articular Cartilage Deformation, Recovery, and Fluid Flow Following Dynamic Exercise In Vivo," Anatomy and Embryology 200: 419-424 (1999).
Eckstein et al., "In Vivo Reproducibility of Three-Dimensional Cartilage Volume and Thickness Measurements With MR Imaging", AJR 170(3): 593-597 (1998).
Eckstein et al., "New Quantitative Approaches With 3-D MRI: Cartilage Morphology, Function and Degeneration", Medical Imaging International, Nov.-Dec. 1998.

Eckstein et al., "Side Differences of Knee Joint Cartilage Volume, Thickness, and Surface Area, and Correlation With Lower Limb Dominance—An MRI-Based Study," Osteoarthritis and Cartilage 10: 914-921 (2002).
Eckstein et al., Accuracy of Cartilage Volume and Thickness Measurements with Magnetic Resonance Imaging, Clin. Orthop. 1998; 352: 137-148 T. 60 V. II.
Eckstein et al., "Magnetic Resonance Chondro-Crassometry (MR CCM): A Method for Accurate Determination of Articular Cartilage Thickness?" Magn. Reson. Med. 35: 89-96 (1996).
Eckstein et al., "The Influence of Geometry on the Stress Distribution in Joints—a Finite Element Analysis," Anat Embryol, 189: 545-552 (1994).
Eckstein et al., "The Morphology of Articular Cartilage Assessed by Magnetic Resonance Imaging: Reproducibility and Anatomical Correlation," Sur. Radiol Anat 16: 429-438 (1994).
Elting et al., "Unilateral frame distraction: proximal tibial valgus osteotomy for medial gonarthritis," Contemp Orthrop 27(6): 522-524 (1993).
Faber et al., "Gender Differences in Knee Joint Cartilage Thickness, Volume and Articular Surface Areas: Assessment With Quantitative Three-Dimensional MR Imaging," Skeletal Radiology 30 (3): 144-150 (2001).
Faber et al., "Quantitative Changes of Articular Cartilage Microstructure During Compression of an Intact Joint," Proc. Intl. Soc. Mag. Resonance Med., 7:547 (1999).
Falcao et al., "User-steered image segmentation paradigms: Live wire and live lane," Graphical Models and Image Processing 60: 233-260 (1998).
Felson et al., "Weight Loss Reduces the risk for symptomatic knee osteoarthritis in women: the Framingham study," Ann Intern Med 116: 535-539 (1992).
Gandy et al., "One-Year Longitudinal Study of Femoral Cartilage Lesions in Knee Arthritis," Proc. Intl. Soc. Mag. Resonance Med., 7:1032 (1999).
Garrett, "Osteochondral allografts for reconstruction of articular defects of the knee," Instr Course Lect 47: 517-522 (1998).
Gerscovich, "A Radiologist's Guide to the Imaging in the Diagnosis and Treatment of Developmental Dysplasia of the Hip," Skeletal Radiol 26: 447-456 (1997).
Ghelman et al., "Kinematics of the Knee After Prosthetic Replacements", Clin. Orthop. May 1975: (108): 149-157.
Ghosh et al., "Watershed Segmentation of High Resolution Articular Cartilage Images for Assessment of Osteoarthritis," International Society for Magnetic Resonance in Medicine, Philadelphia, (1999).
Glaser et al., "Optimization and Validation of a Rapid Highresolution T1-W 3-D Flash Waterexcitation MR Sequence for the Quantitative Assessment of Articular Cartilage Volume and Thickness," Magnetic Resonance Imaging 19: 177-185 (2001).
Goodwin et al., "MR Imaging of Articular Cartilage: Striations in the Radial Layer Reflect the Fibrous Structure of Cartilage," Proc. Intl. Soc. Mag. Resonance Med., 7:546 (1999).
Gouraud, "Continuous shading of curved surfaces," IEEE Trans on Computers C-20(6) (1971).
Graichen et al., "Three-Dimensional Analysis of the Width of the Subacromial Space in Healthy Subjects and Patients With Impingement Syndrome," American Journal of Roentgenology 172: 1081-1086 (1999).
Hafez et al., "Computer Assisted Total Knee Replacement: Could a Two-Piece Custom Template Replace the Complex Conventional Instrumentations?" Session 6: Novel Instruments; Computer Aided Surgery, Session 6, vol. 9, No. 3, pp. 93-94 (Jun. 2004).
Hafez et al., "Computer-assisted Total Knee Arthroplasty Using Patient-specific Templating," *Clinical Orthopaedics and Related Research*, No. 444, pp. 184-192 (Mar. 2006).
Hall et al., "Quantitative MRI for Clinical Drug Trials of Joint Diseases; Virtual Biopsy of Articular Cartilage" NIH-FDA Conf. on Biomarkers and Surrogate Endpoints: Advancing Clinical Research and Applications (1998).
Hardy et al., "Measuring the Thickness of Articular Cartilage From MR Images," J. Magnetic Resonance Imaging 13: 120-126 (2001).

(56) References Cited

OTHER PUBLICATIONS

Hardy et al., "The Influence of the Resolution and Contrast on Measuring the Articular Cartilage Volume in Magnetic Resonance Images" Magn Reson Imaging. 18(8): 965-972 (Oct. 2000).
Hargreaves et al., "MR Imaging of Articular Cartilage Using Driven Equilibrium," Magnetic Resonance in Medicine 42(4): 695-703 (Oct. 1999).
Hargreaves et al., "Technical considerations for DEFT imaging," International Society for Magnetic Resonance in Medicine, Sydney, Australia (Apr. 17-24, 1998).
Hargreaves et al., "Imaging of articular cartilage using driven equilibrium," International Society for Magnetic Resonance in Medicine, Sydney, Australia (Apr. 17-24, 1998).
Hastings et al., "Double Hemiarthroplasty of the Knee in Rheumatoid Arthritis," a Survey of Fifty Consecutive Cases, J. Bone Joint Surg. Br. 55(1):112-118 (1973).
Haubner M, et al., "A Non-Invasive Technique for 3-Dimensional Assessment of Articular Cartilage Thickness Based on MRI Part @: Validation Using CT Arthrography," Magn Reson Imaging; 15(7): 805-813 (1997).
Haut et al., "A High Accuracy Three-Dimensional Coordinate Digitizing System for Reconstructing the Geometry of Diarthrodial Joints," J. Biomechanics 31: 571-577 (1998).
Hayes et al., "Evaluation of Articular Cartilage: Radiographic and Cross-Sectional Imaging Techniques," Radiographics 12: 409-428 (1992).
Henderson et al., "Experience with the Use of the Macintosh Prosthesis in Knees of Patients with Pheumatoid Arthritis," South. Med. J. 62(11):1311-1315 (1969).
Henkelman, "Anisotropy of NMR Properties of Tissues", Magn Res Med. 32: 592-601 (1994).
Herberhold et al., "An MR-Based Technique for Quantifying the Deformation of Articular Cartilage During Mechanical Loading in an Intact Cadaver Joint," Magnetic Resonance in Medicine 39(5): 843-850 (1998).
Herberhold, "In Situ Measurement of Articular Cartilage Deformation in Intact Femorapatellar Joints Under Static Loading", Journal of biomechanics 32: 1287-1295 (1999).
Herrmann et al., "High Resolution Imaging of Normal and Osteoarthritic Cartilage with Optical Coherence Tomogrqaphy," J. Rheumatoil 26: 627-635 (1999).
High et al., "Early Macromolecular Collagen Changes in Articular Cartilage of Osteoarthritis (OA): An In Vivo MT-MRI and Histopathologic Study," Proc. Intl. Soc. Mag. Resonance Med., 7:550 (1999).
Hohe, "Surface Size, Curvature Analysis, and Assessment of Knee Joint Incongruity With MR Imaging In Vivo", Magnetic Resonance in Medicine, 47: 554-561 (2002).
Holdsworth et al., "Benefits of Articular Cartilage Imaging at 4 Tesla: An In Vivo Study of Normal Volunteers," Proc. Intl. Soc. Mag. Resonance Med., 7:1028 (1999).
Hughes et al., "Technical Note: A Technique for Measuring the Surface Area of Articular Cartilage in Acetabular Fractures," Br. J. Radiol; 67: 584-588 (1994).
Husmann et al., "Three-Dimensional Morphology of the Proximal Femur," J. Arthroplasty; 12(4): 444-450 (Jun. 1997).
Hyhlik-Durr et al., "Precision of Tibial Cartilage Morphometry with a coronal water-excitation MR sequence," European Radiology 10(2): 297-303 (2000).
Ihara H., "Double-Contrast CT Arthrography of the Cartilage of the Patellofemoral Joint," Clin. Orthop.; 198: 50-55 (Sep. 1985).
Iida et al., "Socket Location in Total Hip Replacement: Preoperative Computed Tomography and Computer Simulation" Acta Orthop Scand; 59(1): 1-5 (1998).
Irarrazabal et al., "Fast three-dimensional magnetic resonance imaging," Mag Res. Med. 33: 656-662 (1995).
Jessop et al., "Follow-up of the MacIntosh Arthroplasty of the Knee Joint," Rheumatol Phys. Med. 11(5):217-224 (1972).

Johnson et al., "The distribution of load across the knee. A comparison of static and dynamic measurements," J. Bone Joint Surg 62B: 346-349 (1980).
Johnson, "In vivo contact kinematics of the knee joint: Advancing the point cluster technique," Ph.D. Thesis, University of Minnesota (1999).
Johnson et al., "Development of a knee wear method based on prosthetic in vivo slip velocity," Transaction of the Orthopedic Research Society, 46th Annual Meeting (Mar. 2000).
Jonsson et al., "Precision of Hyaline Cartilage Thickness Measurements," Acta Radiol 1992; 33(3): 234-239 (1992).
Kaneuji et al., "Three Dimensional Morphological Analysis of the Proximal Femoral Canal, Using Computer-Aided Design System, in Japanese Patients with Osteoarthrosis of the Hip," J. Orthop Sci; 5(4): 361-368 (2000).
Karvonen et al., "Articular Cartilage Defects of the Knee: Correlation Between Magnetic Resonance Imaging and Gross Pathology," Ann Rheum Dis. 49: 672-675 (1990).
Kass et al., "Snakes: Active contour models.," Int J Comput Vision 1: 321-331 (1988).
Kates, et al., "Experiences of Arthroplasty of the Rheumatoid Knee Using MacIntosh Prostheses," Ann. Rheum. Dis. 28(3):328 (1969).
Kaufman et al., "Articular Cartilage Sodium content as a function of compression" Seventh Scientific Meeting of ISMRM, p. 1022, 1999 T. 105, V. III.
Kay et al., The MacIntosh Tibial Plateau Hemiprosthesis for the Rheumatoid Knee, J. Bone Joint Surg. Br. 54(2):256-262 (1972).
Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).
Klosterman et al., "T2 Measurements in Adult Patellar Cartilage at 1.5 and 3.0 Tesla," ISMRM Seventh Scientific Meeting, Philadelphia, PA, (May 22-28, 1999).
Knauss et al., "Self-Diffusion of Water in Cartilage and Cartilage Components as Studied by Pulsed Field Gradient NMR," Magnetic Resonance in Medicine 41:285-292 (1999).
Koh et al., "Visualization by Magnetic Resonance Imaging of Focal Cartilage Lesions in the Excised Mini-Pig Knee," J. Orthop. Res; 14(4): 554-561 (Jul. 1996).
Korhonen et al., "Importance of the Superficial Tissue Layer for the Indentation Stiffness of Articular Cartilage," Med. Eng. Phys; 24(2): 99-108 (Mar. 2002).
Korkala et al., "Autogenous Osteoperiosteal Grafts in the Reconstruction of Full-Thickness Joint Surface Defects," Int. Orthop.; 15(3): 233-237 (1991).
Kshirsagar et al., "Measurement of Localized Cartilage Volume and Thickness of Human Knee Joints by Computer Analysis of Three-Dimensional Magnetic Resonance Images," Invest Radiol. 33(5): 289-299 (May 1998).
Kwak et al., "Anatomy of Human Patellofemoral Joint Articular Cartilage: Surface Curvature Analysis," J. Orthop. Res.; 15: 468-472 (1997).
LaFortune et al., "Three dimensional kinematics of the human knee during walking," J. Biomechanics 25: 347-357 (1992).
Lam et al., "X-Ray Diagnosis: A Physician's Approach", Editor Lam, 1998, Springer-Verlag publishers, Title page and Index Only (ISBN 9813083247).
Lang et al., "Functional joint imaging: a new technique integrating MRI and biomotion studies," International Society for Magnetic Resonance in Medicine, Denver (Apr. 18-24, 2000).
Lang et al., Risk factors for progression of cartilage loss: a longitudinal MRI study. European Society of Musculoskeletal Radiology, 6th Annual Meeting, Edinburgh, Scotland (1999).
Lang et al., Cartilage imaging: comparison of driven equilibrium with gradient-echo, SPAR, and fast spin-echo sequences. International Society for Magnetic Resonance in Medicine, Sydney, Australia, (Apr. 17-24, 1998).
Ledingham et al., "Factors affecting radiographic progression of knee osteoarthritis," Ann Rheum Dis 54: 53-58 (1995).
Leenslag et al., "A Porous Composite for Reconstruction of Meniscus Lesions," Biological and Biomechanical Perform. of Biomaterials, Elsevier Science Publishers Amsterdam pp. 147-152 (1986).

(56) References Cited

OTHER PUBLICATIONS

Lefebvre et al., "Automatic Three-Dimensional Reconstruction and Characterization of Articular Cartilage from High-Resolution Ultrasound Acquisitions," Ultrasound Med. Biol.; 24(9): 1369-1381 (Nov. 1998).
Li et al., A Boundary Optimization Algorithm for Delineating Brain Objects from CT Scans: Nuclear Science Symposium and Medical Imaging Conference 1993 IEEE Conference Record, San Francisco, CA (1993).
Lin et al., "Three-Dimensional Characteristics of Cartilagenous and Bony Components of Dysplastic Hips in Children: Three-Dimensional Computed Tomography Quantitative Analysis," J. Pediatr. Orthop.; 17: 152-157 (1997).
Lorensen et al., "Marching cubes: a high resolution 3d surface construction algorithm," Comput Graph 21: 163-169 (1987).
Losch et al., "A non-invasive technique for 3-dimensional assessment of articular cartilage thickness based on MRI part 1: development of a computational method," Magn Res Imaging 15(7): 795-804 (1997).
Lu et al., "Bone position estimation from skin marker coordinates using globals optimization with joint constraints," J Biomechanics 32: 129-134 (1999).
Lu et al., "In vitro degradation of porous poly(L-lactic acid) foams", Biomaterials, 21(15):1595-1605, Aug. 2000.
Lucchetti et al., "Skin movement artifact assessment and compensation in the estimation of knee-joint kinematics," J Biomechanics 31: 977-984 (1998).
Lusse et al., "Measurement of Distribution of Water Content of Human Articular Cartilage Based on Transverse Relaxation Times: An In Vitro Study," Seventh Scientific Meeting of ISMRM, p. 1020 (1999).
Lynch et al., "Cartilage segmentation of 3D MRI scans of the osteoarthritic knee combining user knowledge and active contours," Proc. SPIE 3979 Medical Imaging, San Diego pp. 925-935 (Feb. 2000).
MacIntosh, "Arthroplasty of the Knee in Rheumatoid Arthritis," Proceedings and Reports of Councils and Assotions, J. Bone & Joint Surg., vol. 48B No. (1): 179 (Feb. 1996).
MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).
MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).
MacIntosh, "Hemiarthroplasty of the Knee Using a Space Occupying Prosthesis for Painful Varus and Valgus Deformities," J. Bone Joint Surg. Am. Dec. 1958:40-A:1431.
Maki et al., "SNR improvement in NMR microscopy using DEFT," J Mag Res; pp. 482-492 (1988).
Marler et al., "Soft-Tissue Augmentation with Injectable Alginate and Syngeneic Fibroblasts", Plastic & Reconstructive Surgery, 105(6):2049-2058, May 2000.
Marshall et al., "Quantitation of Articular Cartilage Using Magnetic Resonance Imaging and Three-Dimensional Reconstruction," J. Orthop. Res.; 13: 814-823 (1995).
Matsen, III et al., "Robotic Assistance in Orthopaedic Surgery: A Proof of Principle Using Distal Femoral Arthroplasty", Clinical Ortho. and Related Research, 296:178-186 (1993).
Mattila et al., "Massive Osteoarticular Knee Allografts: Structural Changes Evaluated with CT," Radiology; 196: 657-660 (1995).
McCollum et al., "Tibial Plateau Prosthesis in Arthroplasty of the Knee," J. Bone Joint Surg. Am. 1970 52(4):827-8 (Feb. 1996).
McKeever, "The Classic Tibial Plateau Prosthesis," Clin. Orthop. Relat. Res. (192):3-12 (1985).
Merkle et al., "A Transceiver Coil Assembly for Hetero-Nuclear Investigations of Human Breast At 4T," Proc. Intl. Soc. Mag. Resonance Med., 7:170 (1999).
Meyer et al., "Simultaneous spatial and spectral selective excitation," Magn Res Med 15: 287-304 (1990).

Mills et al., "Magnetic Resonance Imaging of the Knee: Evaluation of Meniscal Disease," Curr. Opin. Radiol. 4(6): 77-82 (1992).
Milz et al., "The Thickness of the Subchondral Plate and Its Correlation with the thickness of the Uncalcified Articular Cartilage in the Human Patella," Anat. Embryol.; 192: 437-444 (1995).
Minas, "Chondrocyte Implantation in the Repair of Chondral Lesions of the Knee: Economics and Quality of Life", Am. J. Orthop. Nov. 1998; 27: 739-744.
Modest et al., "Optical Verification of a Technique for In Situ Ultrasonic Measurement of Articular Cartilage Thickness," J. Biomechanics 22(2): 171-176 (1989).
Mollica et al., "Surgical treatment of arthritic varus knee by tibial corticotomy and angular distraction with an external fixator," Ital J Orthrop Traumatol 18(1): 17-23 (1992).
Moussa, "Rotational Malalignment and Femoral Torsion in Osteoarthritic Knees with Patellofemoral Joint Imvolvement: A CT Scan Study," Clin. Orthop.; 304: 176-183 (Jul. 1994).
Mundinger et al., "Magnetic Resonance Tomography in the Diagnosis of Peripheral Joints," Schweiz Med. Wochenschr. 121(15): 517-527 (1991) (Abstract Only).
Myers et al., "Experimental Assessment by High Frequency Ultrasound of Articular Cartilage Thickness and Osteoarthritic Changes," J. Rheumatol; 22: 109-116 (1995).
Nelson et al., "Arthroplasty and Arthrodesis of the Knee Joint," Orthop. Clin. North Am. 2 (1): 245-64 (1971).
Nieminen et al., "T2 Indicates Incompletely the Biomechanical Status of Enzymatically Degraded Articular Cartilage of 9.4T," Proc. Intl. Soc. Mag. Resonance Med., 7:551 (1999).
Nishii et al., "Three Dimensional Evaluation of the Acetabular and Femoral Articular Cartilage in the Osteoarthritis of the Hip Joint," Proc. Intl. Soc. Mag. Resonance Med., 7:1030 (1999).
Nizard, "Role of tibial osteotomy in the treatment of medical femorotibial osteoarthritis," Rev Rhum Engl Ed 65(7-9): 443-446 (1998).
Noll et al., "Homodyne detection in magnetic resonance imaging," IEEE Trans Med Imag 10(2): 154-163 (1991).
Ogilvie-Harris et al., "Arthroscopic management of the degenerative knee," Arthroscopy 7: 151-157 (1991).
Parkkinen et al., "A Mechanical Apparatus With Microprocessor Controlled Stress Profile for Cyclic Compression of Cultured Articular Cartilage Explants," J. Biomech.; 22 (11-12): 1285-1290 (1989).
Pearle et al., "Use of an external MR-tracking coil for active scan plane registration during dynamic Musculoskeletal MR imaging in a vertically open MR unit," American Roentgen Ray Society, San Francisco, CA (1998).
Peterfy et al., "Quantification of the volume of articular cartilage in the carpophalangeal joints of the hand: accuracy and precision of three-dimensional MR imaging," AJR 165: 371-375 (1995).
Peterfy et al., "MR Imaging of the arthritic knee: improved discrimination of cartilage, synovium, and effusion with pulsed saturation transfer and fat-suppressed TI-weighted sequences," Radiology 191(2): 413-419 (1994).
Peterfy et al., "Quantification of articular cartilage in the knee with pulsed saturation transfer subtraction and fat-suppressed MR imaging: optimization and validation," Radiology 192(2): 485-491 (1994).
Peterfy et al., "Emerging Applications of Magnetic Resonance Imaging in the Evaluation of Articular Cartilage," Radiol Clin North Am.; 34(2): 195-213 (Mar. 1996).
Pilch et al., "Assessment of Cartilage Volume in the Femorotibial Joint With Magnetic Resonance Imaging and 3D Computer Reconstruction," J. Rheumatol. 21(12): 2307-2319 (1994).
Piplani et al., "Articular cartilage volume in the knee: semi-automated determination from three-dimensional reformations of MR images," Radiology 198: 855-859 (1996).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "MacIntosh Arthroplasty: A Long-Term Review," J. R. Coll. Surg. Edin. (192):199-201 (1988).
Portheine et al., "CT-Based Planning and Individual Template Navigation in TKA", Navigation and Robotics in Total Joint and Spine Surgery, Springer, 48:336-342 (2004).

(56) References Cited

OTHER PUBLICATIONS

Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Potter et al., "Magnetic resonance imaging of articular cartilage in the knee: an evaluation with use of fast-spin-echo imaging," J Bone Joint Surg 80-A(9): 1276-1284 (1998).
Potter et al., "Sensitivity of Quantitative NMR Imaging to Matrix Composition in Engineered Cartilage Tissue" Proc. Intl. Soc. Mag. Resonance Med., 7:552 (1999).
Probst et al., "Technique for Measuring the Area of Canine Articular Surfaces," Am. J. Vet. Res. 48(4): 608-609 (1987).
Prodromos et al., "A relationship between gait and clinical changes following high tibial osteotomy," J Bone Joint Surg 67A: 1188-1194 (1985).
Radermacher et al., "Computer Assisted Orthopedic Surgery by Means of Individual Templates • Aspects and Analysis of Potential Applications •" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).
Radermacher, English Translation: Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher, "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.
Radin et al., "Mechanical Determination of Osteoarthrosis," Sem Arthr Rheum 21(3): 12-21 (1991).
Radin et al., Characteristics of Joint Loading as it Applies to Osteoarthrosis in: Mow VC, Woo S.Y., Ratcliffe T., eds. Symposium on Biomechanics of Diathrodial Joints, vol. 2, New York, NY: Springer-Verlag, pp. 437-451 (1990).
Ranawat et al., "MacIntosh Hemiarthroplasty in Rheumatoid Knee," Acta Orthop Belg., 39 (1): 1-11 (1973).
Recht et al., "Accuracy of fat-suppressed three-dimensional spoiled gradient-echo Flash MR imaging in the detection of patellofemoral articular cartilage abnormalities," Radiology 198: 209-212 (1996).
Recht et al., "MR imaging of articular cartilage: current status and future directions," AJR 163: 283-290 (1994).
Reiser et al., "Magnetic Resonance in Cartilaginous Lesions of the Knee Joint With Three-Dimensional Gradient-Echo Imaging," Skeletal Radiol. 17(7): 465-471, (1988).
Ritter et al., "Postoperative alignment of total knee replacement," Clin Orthop 299: 153-156 (1994).
Robarts Research Institute, Abstract #1028 (1999).
Robson et al., "A Combined Analysis and Magnetic Resonance Imaging Technique for Computerized Automatic Measurement of Cartilage Thickness in Distal Interphalangeal Joint," Magnetic Resonance Imaging 13(5): 709-718 (1995).
Rushfeldt et al., "Improved Techniques for Measuring In Vitro the Geometry and Pressure Distribution in the Human Acetabulum—1. Ultrasonic Measurement of Acetabular Surfaces, Sphericity and Cartilage Thickness," J. Biomech; 14(4): 253-260 (1981).
Saied, "Assessment of Articular Cartilage and Subchondral Bone: Subtle and Progressive Changes in Experimental Osteoarthritis Using 50 MHz Echography In Vitro", J. Bone Miner Res. 1997; 12(9): 1378-1386.
Saito et al., "New algorithms for Euclidean distance transformation of an—dimensional digitized picture with applications," Pattern Recognition 27(11): 1551-1565 (1994).
Schiffers et al., In German: "Planning and execution of orthopedic surgery using individualized templates," *Der Orthopäde*, Springer-Verlag, vol. 29, No. 7, pp. 636-640, (Jul. 2000).
Schiffers et al., English Translation with Certification: "Planning and execution of orthopedic surgery using individualized templates," *Der Orthopäde*, Springer-Verlag, vol. 29, No. 7, pp. 636-640, (Jul. 2000).
Schipplein et al., "Interaction between active and passive knee stabilizers during level walking," J Orthop Res 9: 113-119 (1991).
Schorn et al., "MacIntosh Arthroplasty in Rheumatoid Arthritis," Rheumatol Rehabil. Aug. 1978:17(3):155-163.
Schouten et al., "A 12 year follow up study in the general population on prognostic factors of cartilage loss in osteoarthritis of the knee," Ann Rheum Dis 51: 932-937 (1992).
Shapiro et al., "In-Vivo Evaluation of Human Cartilage Compression and Recovery using 1H and 23Na MRI," Proc. Intl. Soc. Mag. Resonance Med., 7:548 (1999).
Sharif et al., "Serum hyaluronic acid level as a predictor of disease progression in osteoarthritis of the knee," Arthritis Rheum 38: 760-767 (1995).
Sharma et al., "Knee adduction moment, serum hyaluronic acid level, and disease severity in medial tibiofemoral osteoarthritis," Arthritis and Rheumatism 41(7): 1233-40 (1998).
Shoup et al., "The driven equilibrium Fourier transform NMR technique: an experimental study," J Mag Res p. 298-310 (1972).
Sittek et al., "Assessment of Normal Patellar Cartilage Volume and Thickness Using MRI: an Analysis of Currently Available Pulse Sequences", Skeletal Radiol 1996; 25: 55-61.
Slemenda et al., "Lower extremity lean tissue mass strength predict increases in pain and in functional impairment in knee osteoarthritis," Arthritis Rheum 39(suppl): S212 (1996).
Slemenda et al., "Lower extremity strength, lean tissue mass and bone density in progression of knee osteoarthritis," Arthritis Rheum 39(suppl): S169 (1996).
Slone et al., "Body CT: A Practical Approach", Editor Slone, 1999 McGraw-Hill publishers, Title page and Table of Contents pgs. Only (ISBN 007058219).
Solloway et al., "The use of active shape models for making thickness measurements of articular cartilage from MR images," Mag Res Med 37: 943-952 (1997).
Soslowsky et al., "Articular Geometry of the Glenohumeral Joint," Clin. Orthop.; 285: 181-190 (Dec. 1992).
Spoor et al., "Rigid body motion calculated from spatial coordinates of markers," J. Biomechanics 13: 391-393 (1980).

(56) References Cited

OTHER PUBLICATIONS

Stammberger et al., "A Method for Quantifying Time Dependent Changes in MR Signal Intensity of Articular Cartilage As a Function of Tissue Deformation in Intact Joints" Medical Engineering & Physics 20: 741-749 (1998).
Stammberger et al., "A New Method for 3D Cartilage Thickness Measurement with MRI, Based on Euclidean Distance Transformation, and its Reproducibility in the Living," Proc. Intl. Soc. Mag. Resonance Med., 6:562 (1998).
Stammberger et al., "Elastic Registration of 3D Cartilage Surfaces From MR Image Data for Detecting Local Changes of the Cartilage Thickness," Magnetic Resonance in Medicine 44: 592-601 (2000).
Stammberger et al., "Determination of 3D cartilage thickness data from MR imaging: computational method and reproducibility in the living," Mag Res Med 41: 529-536 (1999).
Stammberger et al., "Interobserver to reproducibility of quantitative cartilage measurements: Comparison of B-spline snakes and manual segmentation," Mag Res Imaging 17: 1033-1042 (1999).
Stauffer et al., "The MacIntosh Prosthesis. Prospective Clinical and Gait Evaluation," Arch. Surg. 110(6):717-720 (1975).
Steines et al., Segmentation of osteoarthritic femoral cartilage using live wire, Proc. Intl. Soc. Mag. Resonance Med., 8:220 (2000).
Steines et al., "Segmentation of osteoarthritis femoral cartilage from MR images," CARS—Computer-Assisted Radiology and Surgery, pp. 578-583, San Francisco (2000).
Steines et al., "Measuring volume of articular cartilage defects in osteoarthritis using MRI," ACR 64th Annual Scientific Meeting, Philadelphia, (Oct. 2000).
Stevenson et al., "The fate of articular cartilage after transplantation of fresh and cryopreserved tissue-antigen-matched and mismatched osteochondral allografts in dogs," J. Bone Joint Surg 71(9): 1297-1307 (1989).
Stout et al., "X-Ray Structure Determination: A Practical Guide", $2^{nd}$ Ed. Editors Stout and Jensen, 1989, John Wiley & Sons, Title page and Table of Contents pgs. Only (ISBN 0471607118).
Taha et al., "Modeling and Design of a Custom Made Cranium Implant for Large Skull Reconstruction Before a Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.
Tebben et al., "Three-Dimensional Computerized Reconstruction. Illustration of Incremental Articular Cartilage Thinning," Invest. Radiol. 32(8): 475-484 (1997).
Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., In German: "Custom-made knee endoprosthetics using subtraction data of three-dimensional CT scans—a new approach," *Der Orthopäde*, Springer-Verlag, vol. 29, No. 7, pp. 641-644, (Jul. 2000).
Thoma et al., English Translation with Certification: "Custom-made knee endoprosthetics using subtraction data of three-dimensional CT scans—a new approach," *Der Orthopäde*, Springer-Verlag, vol. 29, No. 7, pp. 641-644, (Jul. 2000).
Tieschky et al., "Repeatability of patellar cartilage thickness patterns in the living, using a fat-suppressed magnetic resonance imaging sequence with short acquisition time and three-dimensional data processing," J. Orthop Res 15(6): 808-813 (1997).
Tomasi et al., "Shape and motion from image streams under orthography—a factorization method," Proc. Nat. Acad. Sci. 90(21): 9795-9802 (1993).

Tsai et al., "Application of a flexible loop-gap resonator for MR imaging of articular cartilage at 3.TO," International Society for Magnetic Resonance in Medicine, Denver (Apr. 24-28, 2000) 8:2127.
Tyler et al., "Detection and Monitoring of Progressive Degeneration of Osteoarthritic Cartilage by MRI," Acta Orthop Scand 1995; 66 Suppl. 266: 130-138 (1995).
Van Leersum et al., "Thickness of Patellofemoral Articular Cartilage as Measured on MR Imaging: Sequence Comparison of accuracy, reproducibility, and interobserver variation," Skeletal Radiol 1995; 24: 431-435 (1995).
Vandeberg et al., "Assessment of Knee Cartilage in Cadavers with Dual-Detector Sprial CT ARthrography and MR Imaging", Radiology, Feb. 2002: 222(2): 430-435 T. 195, V.V.
Van der Linden et al., "MR Imaging of Hyaline Cartilage at 0.5 T: A Quantitative and Qualitative in vitro Evaluation of Three Types of Sequences" pp. 297-305 (Jun. 1998).
Velyvis et al., "Evaluation of Articular Cartilage with Delayed Gd(DTPA)2-Enhanced MRI: Promise and Pitfalls," Proc. Intl. Soc. Mag. Resonance Med., 7:554 (1999).
Wang et al., "The influence of walking mechanics and time on the results of proximal tibial osteotomy," J. Bone Joint Surg 72A: 905-909 (1990).
Warfield et al., "Automatic Segmentation of MRI of the Knee," ISMRM Sixth Scientific Meeting and Exhibition p. 563, Sydney, Australia (Apr. 17-24, 1998).
Warfield et al., "Adaptive Template Moderated Spatially Varying Statistical Classification," Proc. First International Conference on Medical Image Computing and Computer Assisted, MICCAI, pp. 231-238 (1998).
Warfield et al., "Adaptive, Template Moderated Spatially Varying Statistical Classification," Medical Image Analysis 4(1): 43-55 (2000).
Waterton et al., "Diurnal variation in the femoral articular cartilage of the knee in young adult humans," Mag Res Med 43: 126-132 (2000).
Waterton et al., "Magnetic Resonance Methods for Measurement of Disease Progression in Rheumatoid Arthritis," Mag. Res. Imaging; 11: 1033-1038 (1993).
Watson et al., "MR Protocols for Imaging the Guinea Pig Knee," Mag. Res. Imaging 15(8): 957-970 (1997).
Wayne et al., "Measurement of Articular Cartilage Thickness in the Articulated Knee," Ann Biomed Eng.; 26(1): 96-102 (1998).
Wayne et al., "Finite Element Analyses of Repaired Articular Surfaces," Proc. Instn. Mech. Eng.; 205(3): 155-162 (1991).
Wiese et al., "Biomaterial properties and biocompatibility in cell culture of a novel self-inflating hydrogel tissue expander", J. Biomedical Materials Research Part A, 54(2):179-188, Nov. 2000.
Wolff et al., "Magnetization transfer contrast: MR imaging of the knee," Radiology 179: 623-628 (1991).
Wordsworth et al., "MacIntosh Arthroplasty for the Rheumatoid Knee: A 10-year Follow Up," Ann. Rheum. Dis. 44(11):738-741 (1985).
Worring et al., "Digital curvature estimation. CVGIP," Image Understanding 58(3): 366-382 (1993).
Yan, "Measuring changes in local volumetric bone density," new approaches to quantitative computed tomography, Ph.D. thesis, Dept. of Electrical Engineering, Stanford University (1998).
Yao et al., "Incidental magnetization transfer contrast in fast spin-echo imaging of cartilage," J. Magn Reson Imaging 6(1): 180-184 (1996).
Yao et al., "MR imaging of joints: analytic optimization of GRE techniques at 1.5T," AJR 158(2): 339-345 (1992).
Yasuda et al., "A 10 to 15 year follow up observation of high tibial osteotomy in medial compartment osteoarthritis," Clin Orthop 282: 186-195 (1992).
Yusof et al., "Preparation and characterization of chitin beads as a wound dressing precursor", J. Biomedical Materials Research Part A, 54(1):59-68, Oct. 2000.
Zimmer, Inc., "There's a New Addition to the Flex Family! The Zimmer® Unicompartmental Knee System", pp. 1-8 (2004).

(56) References Cited

OTHER PUBLICATIONS

International Searching Authority, International Search Report—International Application No. PCT/US02/16945, dated Mar. 26, 2003, 6 pages.
European Patent Office, Supplementary European Search Report—Application No. 03713907.8, dated Dec. 6, 2006, 3 pages.
European Patent Office, Supplementary Partial European Search Report—Application No. 02737254.9, dated Mar. 2, 2007, 5 pages.
International Searching Authority, International Search Report—International Application No. PCT/US03/38158, dated Feb. 23, 2005, 7 pages.
European Patent Office, European Search Report—Application No. EP 03790194, dated Jul. 13, 2006, 7 pages.
International Searching Authority, International Search Report—International Application No. PCT/US03/32123, dated Mar. 17, 2004, 7 pages.
International Searching Authority, International Search Report—International Application No. PCT/US03/36079, dated Apr. 15, 2004, 7 pages.
International Searching Authority, International Search Report—International Application No. PCT/US04/39714, dated May 13, 2005, together with the Written Opinion of the International Searching Authority, 8 pages.
International Searching Authority, International Search Report—International Application No. PCT/US2005/042421, dated May 18, 2006, together with the Written Opinion of the International Searching Authority, 7 pages.
European Patent Office, Supplementary European Search Report—Application No. 04812273.3, dated Oct. 8, 2007, 5 pages.
International Searching Authority, Invitation to Pay Additional Fees—International Application No. PCT/US2007/064349 dated Aug. 7, 2007, 8 pages.
International Searching Authority, International Search Report—International Application No. PCT/US2007/064349, dated Oct. 12, 2007, together with the Written Opinion of the International Searching Authority, 20 pages.
European Patent Office, Supplementary European Search Report—Application No. 04812273.3-2310, dated Dec. 10, 2007, 7 pages.
International Searching Authority, International Search Report—International Application No. PCT/US06/45131, dated Jul. 11, 2007, together with the Written Opinion of the International Searching Authority, 6 pages.
International Searching Authority, International Search Report—International Application No. PCT/US06/38212, dated Apr. 22, 2008, together with the Written Opinion of the International Searching Authority, 7 pages.
International Searching Authority, International Preliminary Report on Patentability—International Application No. PCT/US2006/045131, dated Jun. 5, 2008, together with the Written Opinion of the International Searching Authority, 6 pages.
International Searching Authority, International Search Report—International Application No. PCT/US2009/043656, dated Jul. 9, 2009, together with the Written Opinion of the International Searching Authority, 8 pages.
United States Patent and Trademark Office, Office Action dated Jul. 30, 2009, pertaining to U.S. Appl. No. 11/537,318, 56 pages.
Sunstein Kann Murphy & Timbers LLP, Request for Continued Examination and Response dated Aug. 27, 2009 pertaining to U.S. Appl. No. 10/752,438, 22 pages.
United States Patent and Trademark Office, Office Action dated Nov. 10, 2009 pertaining to U.S. Appl. No. 10/752,438, 8 pages.
Sunstein Kann Murphy & Timbers LLP, Request for Continued Examination and Response dated Jul. 27, 2009 pertaining to U.S. Appl. No. 10/997,407, 26 pages.
United States Patent and Trademark Office, Office Action dated Nov. 24, 2009 pertaining to U.S. Appl. No. 10/997,407, 14 pages.
United States Patent and Trademark Office, Office Action dated Jan. 9, 2009, pertaining to U.S. Appl. No. 10/764,010 (US Patent Publication No. US 2004/0167390), 11 pages.
Bromberg & Sunstein LLP, Response to Office Action dated Jan. 9, 2009, pertaining to U.S. Appl. No. 10/764,010 (US Patent Publication No. US 2004/0167390), 25 pages.
United States Patent and Trademark Office, Office Action dated Oct. 23, 2009, pertaining to U.S. Appl. No. 10/764,010 (US Patent Publication No. US 2004/0167390), 13 pages.
United States Patent and Trademark Office, Office Action dated Jul. 9, 2009, pertaining to U.S. Appl. No. 10/160,667, 5 pages.
Sunstein Kann Murphy & Timbers LLP, Amendment dated Jan. 11, 2010, pertaining to U.S. Appl. No. 10/160,667, 12 pages.
United States Patent and Trademark Office, Office Action dated Aug. 6, 2009, pertaining to U.S. Appl. No. 10/681,749, 6 pages.
Sunstein Kann Murphy & Timbers LLP, Response to Office Action dated Aug. 6, 2009, pertaining to U.S. Appl. No. 10/681,749, 18 pages.
United States Patent and Trademark Office, Office Action dated Nov. 25, 2008, pertaining to U.S. Appl. No. 10/681,750, 21 pages.
Sunstein Kann Murphy & Timbers LLP, Response to Office Action dated Nov. 25, 2008, pertaining to U.S. Appl. No. 10/681,750, 17 pages.
United States Patent and Trademark Office, Office Action dated Sep. 22, 2009, pertaining to U.S. Appl. No. 10/681,750, 21 pages.
European Patent Office, European Search Report—International Application No. PCT/US2006/045131 dated Mar. 3, 2010, 6 pages.
United States Patent and Trademark Office, Office Action dated Apr. 24, 2009, pertaining to U.S. Appl. No. 10/704,208, 23 pages.
Sunstein Kann Murphy & Timbers LLP, Request for Continued Examination and Response dated Oct. 26, 2009, pertaining to U.S. Appl. No. 10/704,208, 17 pages.
United States Patent and Trademark Office, Office Action dated Dec. 30, 2009, pertaining to U.S. Appl. No. 10/704,208, 10 pages.
International Searching Authority, International Search Report—International Application No. PCT/US2010/025459, dated Apr. 20, 2010, together with the Written Opinion of the International Searching Authority, 15 pages.
Bromberg & Sunstein LLP, Request for Continued Examination dated May 24, 2007, pertaining to U.S. Appl. No. 10/305,652, 21 pages.
United States Patent and Trademark Office, Office Action dated Aug. 13, 2007, pertaining to U.S. Appl. No. 10/305,652, 6 pages.
Bromberg & Sunstein LLP, Response to Office Action dated Aug. 13, 2007, pertaining to U.S. Appl. No. 10/305,652, 10 pages.
United States Patent and Trademark Office, Office Action dated Dec. 19, 2007, pertaining to U.S. Appl. No. 10/305,652, 6 pages.
Bromberg & Sunstein LLP, Response to Office Action dated Dec. 19, 2007, pertaining to U.S. Appl. No. 10/305,652, 17 pages.
Bromberg & Sunstein LLP, Supplemental Response dated May 2, 2008, pertaining to U.S. Appl. No. 10/305,652, 12 pages.
United States Patent and Trademark Office, Office Action dated Jul. 29, 2008, pertaining to U.S. Appl. No. 10/305,652, 10 pages.
Bromberg & Sunstein LLP, Amendment After Final Rejection dated Aug. 26, 2008, pertaining to U.S. Appl. No. 10/305,652, 17 pages.
United States Patent and Trademark Office, Office Action dated Aug. 4, 2009, pertaining to U.S. Appl. No. 10/704,325, 11 pages.
Sunstein Kann Murphy & Timbers LLP, Response to Office Action dated Aug. 4, 2009, pertaining to U.S. Appl. No. 10/704,325, 15 pages.
United States Patent and Trademark Office, Notice of Allowance dated May 17, 2010, pertaining to U.S. Appl. No. 10/704,325, 20 pages.
United States Patent and Trademark Office, Office Action dated Jul. 23, 2010, pertaining to U.S. Appl. No. 12/317,416, 7 pages.
United States Patent and Trademark Office, Office Action dated Apr. 26, 2010, pertaining to U.S. Appl. No. 10/160,667, 11 pages.
United States Patent and Trademark Office, Office Action dated Aug. 2, 2010, pertaining to U.S. Appl. No. 12/317,472, 7 pages.
United States Patent and Trademark Office, Office Action dated Aug. 5, 2010, pertaining to U.S. Appl. No. 10/997,407, 12 pages.
United States Patent and Trademark Office, Office Action dated May 26, 2010, pertaining to U.S. Appl. No. 11/602,713, 10 pages.
United States Patent and Trademark Office, Office Action dated Jun. 28, 2010, pertaining to U.S. Appl. No. 10/752,438, 9 pages.

(56) References Cited

OTHER PUBLICATIONS

United States Patent and Trademark Office, Office Action dated Mar. 4, 2010, pertaining to U.S. Appl. No. 11/688,340, 15 pages.
Sunstein Kann Murphy & Timbers LLP, Response to Office Action dated Jul. 30, 2009, pertaining to U.S. Appl. No. 11/537,318, 9 pages.
United States Patent and Trademark Office, Office Action dated Jun. 3, 2010, pertaining to U.S. Appl. No. 11/537,318, 10 pages.
International Searching Authority, International Search Report—International Application No. PCT/US2010/039587, dated Aug. 19, 2010, together with the Written Opinion of the International Searching Authority, 15 pages.
European Patent Office, Extended European Search Report—European Application No. 06815884.9-2310, dated Sep. 14, 2010, 7 pages.
United States Patent and Trademark Office, Office Action dated Sep. 15, 2010, pertaining to U.S. Appl. No. 10/704,208, 13 pages.
International Searching Authority, International Search Report—International Application No. PCT/US2010/025274, dated Sep. 20, 2010, together with the Written Opinion of the International Searching Authority, 18 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.
Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.
United States Patent and Trademark Office, Office Action dated May 17, 2010, pertaining to U.S. Appl. No. 10/764,010, 12 pages.
Sunstein Kann Murphy & Timbers LLP, Response to Office Action dated May 17, 2010, pertaining to U.S. Appl. No. 10/764,010, 21 pages.
United States Patent and Trademark Office, Notice of Allowance dated Dec. 16, 2010, pertaining to U.S. Appl. No. 10/764,010, 11 pages.
Sunstein Kann Murphy & Timbers LLP, Response to Office Action dated Aug. 2, 2010, pertaining to U.S. Appl. No. 12/317,472, 15 pages.
United States Patent and Trademark Office, Office Action dated Feb. 10, 2011, pertaining to U.S. Appl. No. 12/317,416, 10 pages.
International Searching Authority, International Search Report—International Application No. PCT/US2010/046868, dated Jan. 7, 2011, together with the Written Opinion of the International Searching Authority, 11 pages.
United States Patent and Trademark Office, Office Action dated Feb. 22, 2011, pertaining to U.S. Appl. No. 11/602,713, 10 pages.
United States Patent and Trademark Office, Office Action dated Feb. 24, 2011, pertaining to U.S. Appl. No. 12/317,472, 12 pages.
United States Patent and Trademark Office, Office Action dated Mar. 2, 2011, pertaining to U.S. Appl. No. 10/752,438, 8 pages.
European Patent Office, Extended European Search Report—European Application No. 10012404.9-2310, dated Apr. 1, 2011, 7 pages.
United States Patent and Trademark Office, Office Action dated Apr. 18, 2011, pertaining to U.S. Appl. No. 12/464,763, 13 pages.
United States Patent and Trademark Office, Notice of Allowance dated Aug. 5, 2011, pertaining to U.S. Appl. No. 10/764,010, 14 pages.
United States Patent and Trademark Office, Office Action dated Sep. 15, 2011, pertaining to U.S. Appl. No. 10/997,407, 13 pages.
United States Patent and Trademark Office, Office Action dated Dec. 6, 2010, pertaining to U.S. Appl. No. 12/853,599, 11 pages.
Sunstein Kann Murphy & Timbers LLP, Response to Office Action dated Dec. 6, 2010, pertaining to U.S. Appl. No. 12/853,599, 16 pages.
United States Patent and Trademark Office, Notice of Allowance dated Sep. 14, 2011, pertaining to U.S. Appl. No. 12/853,599, 9 pages.
International Searching Authority, International Search Report—International Application No. PCT/US2010/055483, dated Jul. 28, 2011, together with the Written Opinion of the International Searching Authority, 9 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Preliminary Amendment dated Aug. 12, 2011, pertaining to U.S. Appl. No. 13/017,886, 13 pages.
United States Patent and Trademark Office, Office Action dated Jun. 23, 2011 pertaining to U.S. Appl. No. 11/410,515, 13 pages.
International Searching Authority, International Search Report—International Application No. PCT/US2010/059910 dated Oct. 25, 2011, together with the Written Opinion of the International Searching Authority, 9 pages.
International Searching Authority, International Search Report—International Application No. PCT/US2012/025269 dated Aug. 31, 2012, together with the Written Opinion of the International Searching Authority, 14 pages.
International Searching Authority, International Search Report—International Application No. PCT/US2012/049472 dated Oct. 16, 2012, together with the Written Opinion of the International Searching Authority, 12 pages.
International Searching Authority, International Search Report—International Application No. PCT/US2012/050964 dated Oct. 22, 2012, together with the Written Opinion of the International Searching Authority, 13 pages.
International Searching Authority, International Search Report—International Application No. PCT/US2009/036165, dated May 7, 2009, together with the Written Opinion of the International Searching Authority, 9 pages.
European Patent Office, European Search Report—Application No. 12170854.9-1526, dated Oct. 9, 2012, 6 pages.
International Searching Authority, International Search Report—International Application No. PCT/US12/59936 dated Jan. 9, 2013, together with the Written Opinion of the International Searching Authority, 11 pages.
European Patent Office, European Search Report—Application No. 10192339.9-1257, dated Jan. 23, 2013, 5 pages.
European Patent Office, Extended European Search Report—Application No. 10792589.3-2310, dated Feb. 7, 2013, 9 pages.
European Patent Office, Extended European Search Report—Application No. 10746859.7-1654 dated Mar. 4, 2013, 7 pages.

(56) References Cited

OTHER PUBLICATIONS

International Searching Authority, International Search Report—International Application No. PCT/US2013/035536 dated Jul. 18, 2013, 3 pages.
International Searching Authority, International Search Report—International Application No. PCT/US2013/028762 dated Jun. 21, 2013, 9 pages.
International Searching Authority, International Search Report—International Application No. PCT/US2013/061042 dated Jan. 10, 2014, together with the Written Opinion of the International Searching Authority, 12 pages.
International Searching Authority, International Search Report—International Application No. PCT/US13/56841 dated Feb. 12, 2014, together with the Written Opinion of the International Searching Authority, 9 pages.
European Searching Authority, Extended European Search Report—Application No. 10836760.8-1654 dated Apr. 11, 2014, 6 pages.
Delp et al., "A Graphics-Based Software System to Develop and Analyze Models of Musculoskeletal Structures," Comput. Biol. Med., vol. 25, No. 1, pp. 21-34, 1995.
Harryson et al., "Custom-Designed Orthopedic Implants Evaluated Using Finite Element Analysis of Patient-Specific Computed Tomoraphy Data: Femoral-Component Case Study", BMC Musculoskeletal Disorders, vol. 8(91), Sep. 2007, 10 pages.
Lombardi, Jr. et al. "Patient-Specific Approach in Total Knee Arthroplasty", Orthopedics, vol. 31, Issue 9, Sep. 2008, 8 pages.
Overhoff et al., "Total Knee Arthroplasty: Coordinate System Definition and Planning Based on 3-D Ultrasound Image Volumes", CARS 2001, pp. 283-288.
Robinson et al., "The Early Innovators of Today's Resurfacing Condylar Knees", The Journal of Arthroplasty, vol. 20, No. 1, Suppl. 1, 2005.
Tsai et al., "Accurate Surface Voxelization for Manipulating Volumetric Surfaces and Solids with Application in Simulating Musculoskeletal Surgery", Inst. of Information and Computer Engineering, pp. 234-243, 2001.
European Patent Office, European Search Report—Application No. 10829105.5-1654 dated Nov. 5, 2013, 3 pages.
European Patent Office, Extended European Search Report—Application No. 10838327.4-1654 dated Nov. 14, 2013, 6 pages.
International Searching Authority, Great Britain Search and Examination Report—Application No. GB1201112.8 dated Feb. 3, 2014, 4 pages.
International Searching Authority, International Search Report—International Application No. PCT/US2012/025274, dated Oct. 25, 2012, together with the Written Opinion of the International Searching Authority, 12 pages.
International Searching Authority, International Search Report—International Application No. PCT/US2012/025277, dated Oct. 25, 2012, together with the Written Opinion of the International Searching Authority, 12 pages.
International Searching Authority, International Search Report—International Application No. PCT/US2010/061141, dated Aug. 31, 2011, together with the Written Opinion of the International Searching Authority, 8 pages.
International Searching Authority, International Search Report—International Application No. PCT/US14/27446 dated Aug. 11, 2014, together with the Written Opinion of the International Searching Authority, 14 pages.
Cohen et al., "Computer-Aided Planning of Patellofemoral Joint OA Surgery: Developing Physical Models from Patient MRI", MICCAI, Oct. 11-13, 1998, 13 pages.
European Patent Office, Extended European Search Report—Application No. 12192903.8-1654 dated Apr. 17, 2013, 8 pages.
International Searching Authority, International Search Report—International Application No. PCT/US2012/025280 dated Oct. 25, 2012, together with the Written Opinion of the International Searching Authority, 11 pages.

"Seedhom et al., "Dimensions of the Knee. Radiographic and Autopsy Study of Sizes Required by a Knee Prosthesis", Ann. Rheum Dis, pp. 54-58, 1972".
"Erkman et al. "A Study of Knee Geometry Applied to the Design of Condylar Prostheses", Biomedical Engineering, pp. 14-17, Jan. 1974".
"Fehring et al. "Differences Between the Sexes in the Anatomy of the Anterior Condyle of the Knee", Journal of Bone & Joint Surgery, pp. 2335-2341, 2009".
"Mensch et al. "Knee Morphology as a Guide to Knee Replacement", Clinical Orthopaedics and Related Research, pp. 231-241, 1975".
Delp et al., "Computer Assisted Knee Replacement," Clinical Orthopaedics, vol. 354, pp. 49-56, Sep. 1998.
European Patent Office, Extended European Search Report—Application No. 12820490.6-1654, dated Jun. 26, 2015, 6 pages.
European Patent Office, European Search Report pertaining to European Application No. 15189568.7-1654 dated Feb. 9, 2016, 7 pages.
International Searching Authority, International Search Report—International Application No. PCT/US2014/030001 dated Aug. 27, 2014, together with the Written Opinion of the International Searching Authority, 10 pages.
Japanese Patent Office, Office Action pertaining to JP Application No. 2012-109834, dated Jun. 24, 2016, 4 pages.
Japanese Patent Office, English Translation of Office Action pertaining to JP Application No. 2012-109834, dated Jun. 24, 2016, 7 pages.
U.S. Appl. No. 10/160,667, filed May 28, 2002.
U.S. Appl. No. 10/305,652, filed Nov. 27, 2002, now U.S. Pat. No. 7,468,074.
U.S. Appl. No. 10/681,749, filed Oct. 7, 2003, now U.S. Pat. No. 7,799,077.
U.S. Appl. No. 10/681,750, filed Oct. 7, 2003.
U.S. Appl. No. 10/704,208, filed Nov. 7, 2003, now U.S. Pat. No. 8,932,363.
U.S. Appl. No. 10/704,325, filed Nov. 7, 2003, now U.S. Pat. No. 7,796,791.
U.S. Appl. No. 10/752,438, filed Jan. 5, 2004, now U.S. Pat. No. 8,545,569.
U.S. Appl. No. 10/997,407, filed Nov. 24, 2004, now U.S. Pat. No. 8,882,847.
U.S. Appl. No. 11/537,318, filed Sep. 29, 2006.
U.S. Appl. No. 12/317,416, filed Dec. 22, 2008, now U.S. Pat. No. 8,343,218.
U.S. Appl. No. 12/317,472, filed Dec. 22, 2008, now U.S. Pat. No. 8,337,507.
U.S. Appl. No. 11/688,340, filed Mar. 20, 2007.
U.S. Appl. No. 11/602,713, filed Nov. 21, 2006.
U.S. Appl. No. 12/031,239, filed Feb. 14, 2008, now U.S. Pat. No. 8,617,242.
U.S. Appl. No. 12/398,598, filed Mar. 5, 2009, now U.S. Pat. No. 8,682,052.
U.S. Appl. No. 12/398,871, filed Mar. 5, 2009.
U.S. Appl. No. 12/398,880, filed Mar. 5, 2009.
U.S. Appl. No. 12/464,763, filed May 12, 2009.
U.S. Appl. No. 12/712,072, filed Feb. 24, 2010, now U.S. Pat. No. 8,234,097.
U.S. Appl. No. 12/772,683, filed May 3, 2010, now U.S. Pat. No. 8,709,089.
U.S. Appl. No. 12/777,859, filed May 11, 2010, now U.S. Pat. No. 8,768,028.
U.S. Appl. No. 12/777,878, filed May 11, 2010, now U.S. Pat. No. 8,690,945.
U.S. Appl. No. 12/778,506, filed May 12, 2010.
U.S. Appl. No. 12/778,518, filed May 12, 2010, now U.S. Pat. No. 8,945,230.
U.S. Appl. No. 12/660,529, filed Feb. 25, 2010, now U.S. Pat. No. 8,480,754.
U.S. Appl. No. 12/799,299, filed Apr. 21, 2010.
U.S. Appl. No. 12/799,355, filed Apr. 22, 2010.
U.S. Appl. No. 12/799,641, filed Apr. 28, 2010.

(56) References Cited

OTHER PUBLICATIONS

U.S. Appl. No. 12/821,301, filed Jun. 23, 2010, now U.S. Pat. No. 8,771,365.
U.S. Appl. No. 12/853,599, filed Aug. 10, 2010, now U.S. Pat. No. 8,077,950.
U.S. Appl. No. 13/044,413, filed Mar. 9, 2011, now U.S. Pat. No. 8,556,983.
U.S. Appl. No. 13/157,857, filed Jun. 10, 2011, now U.S. Pat. No. 8,735,773.
U.S. Appl. No. 13/312,339, filed Dec. 6, 2011, now U.S. Pat. No. 8,634,617.
U.S. Appl. No. 13/294,564, filed Nov. 11, 2011, now U.S. Pat. No. 8,906,107.
U.S. Appl. No. 13/294,573, filed Nov. 11, 2011, now U.S. Pat. No. 8,974,539.
U.S. Appl. No. 13/294,579, filed Nov. 11, 2011, now U.S. Pat. No. 8,926,706.
U.S. Appl. No. 13/294,617, filed Nov. 11, 2011.
U.S. Appl. No. 13/294,623, filed Nov. 11, 2011.
U.S. Appl. No. 13/397,457, filed Feb. 15, 2012, now U.S. Pat. No. 9,020,788.
U.S. Appl. No. 13/399,378, filed Feb. 17, 2012.
U.S. Appl. No. 13/561,696, filed Jul. 30, 2012.
U.S. Appl. No. 13/565,840, filed Aug. 3, 2012.
U.S. Appl. No. 13/718,717, filed Dec. 18, 2012.
U.S. Appl. No. 13/718,735, filed Dec. 18, 2012.
U.S. Appl. No. 13/746,742, filed Jan. 22, 2013.
U.S. Appl. No. 13/761,818, filed Feb. 7, 2013.
U.S. Appl. No. 13/835,863, filed Mar. 15, 2013.
U.S. Appl. No. 13/886,040, filed May 2, 2013.
U.S. Appl. No. 13/887,712, filed May 6, 2013.
U.S. Appl. No. 13/938,081, filed Jul. 9, 2013.
U.S. Appl. No. 14/017,176, filed Sep. 3, 2013.
U.S. Appl. No. 14/040,890, filed Sep. 30, 2013.
U.S. Appl. No. 14/051,003, filed Oct. 10, 2013.
U.S. Appl. No. 14/051,087, filed Oct. 10, 2013.
U.S. Appl. No. 14/134,064, filed Dec. 19, 2013.
U.S. Appl. No. 14/148,511, filed Jan. 6, 2014.
U.S. Appl. No. 14/157,707, filed Jan. 17, 2014, now U.S. Pat. No. 8,965,088.
U.S. Appl. No. 14/236,782, filed Feb. 3, 2014.
U.S. Appl. No. 14/216,473, filed Mar. 17, 2014.
U.S. Appl. No. 14/222,836, filed Mar. 24, 2014, now U.S. Pat. No. 9,180,015.
U.S. Appl. No. 14/222,253, filed Mar. 21, 2014.
U.S. Appl. No. 14/246,335, filed Apr. 7, 2014, now U.S. Pat. No. 9,186,254.
U.S. Appl. No. 14/259,548, filed Apr. 23, 2014.
U.S. Appl. No. 14/285,151, filed May 22, 2014.
U.S. Appl. No. 14/308,070, filed Jun. 18, 2014.
U.S. Appl. No. 14/315,714, filed Jun. 26, 2014.
U.S. Appl. No. 14/537,175, filed Nov. 10, 2014.
U.S. Appl. No. 14/594,492, filed Jan. 12, 2015.
U.S. Appl. No. 14/696,724, filed Apr. 27, 2015.

* cited by examiner

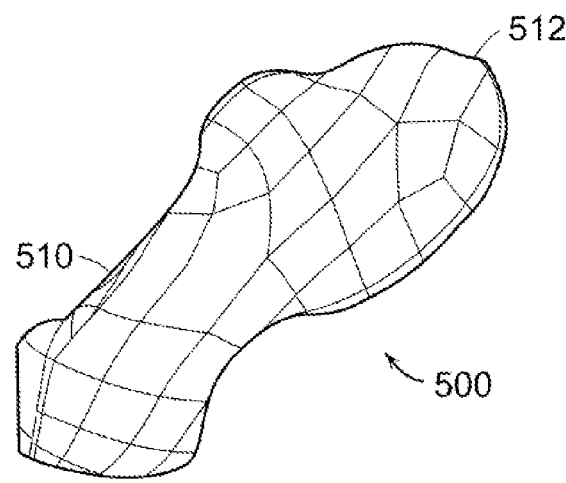
*FIG. 2A*
*FIG. 2B*
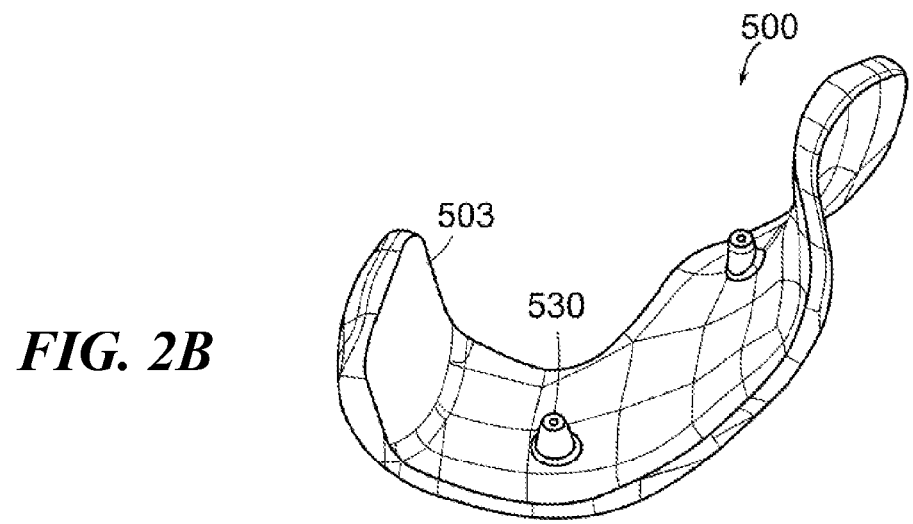
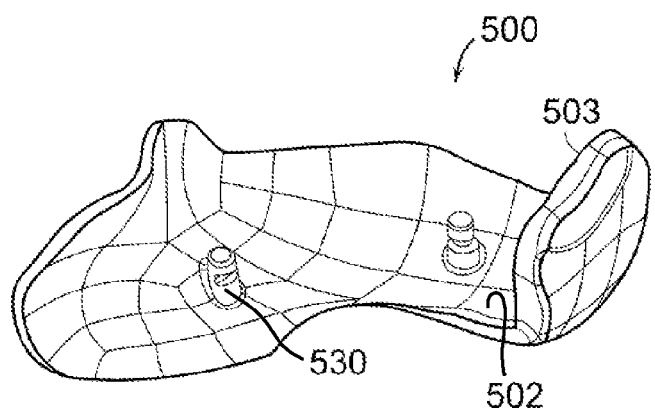
*FIG. 2C*

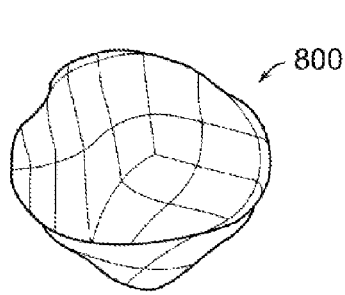
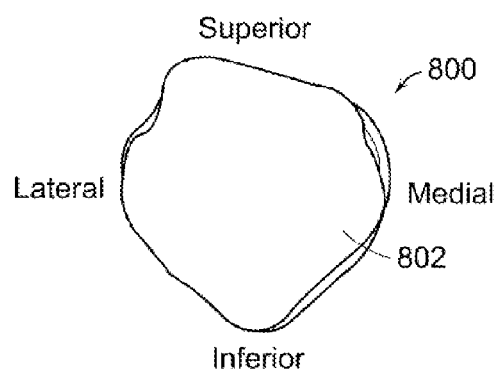
FIG. 12A
FIG. 12B
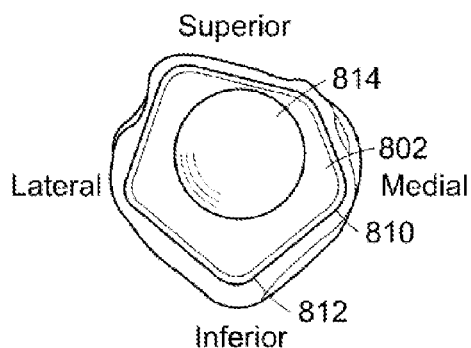
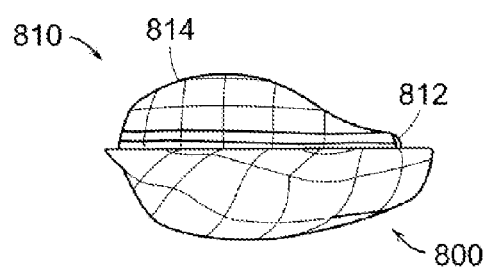
FIG. 12C
FIG. 12D
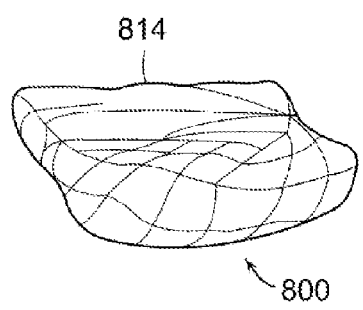
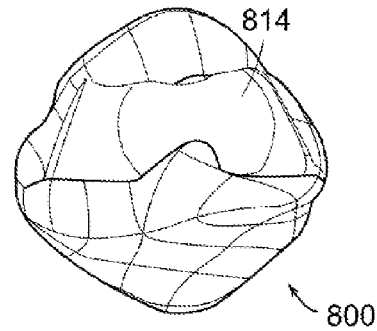
FIG. 12E
FIG. 12F

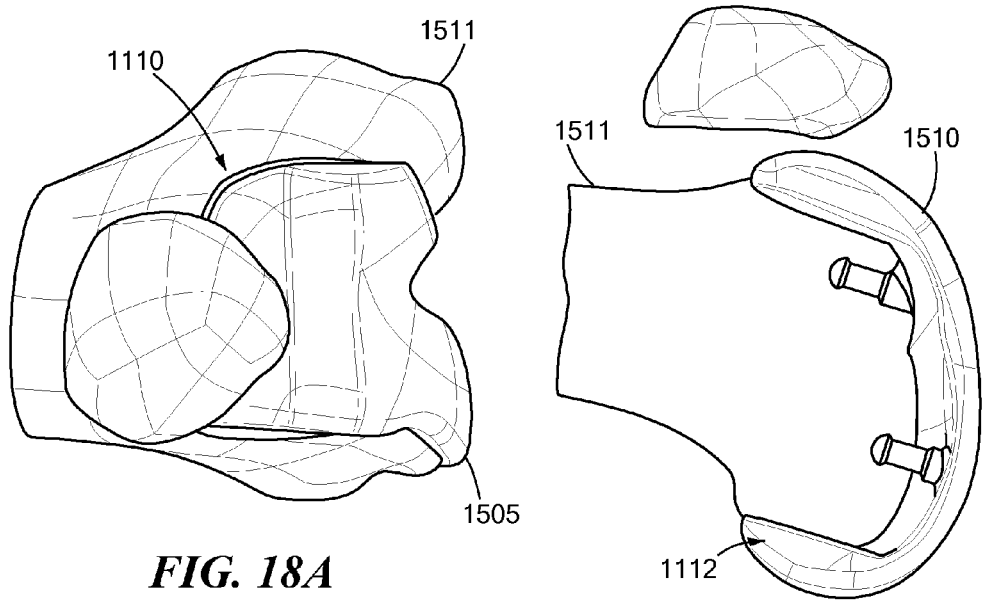
FIG. 18A
FIG. 18B
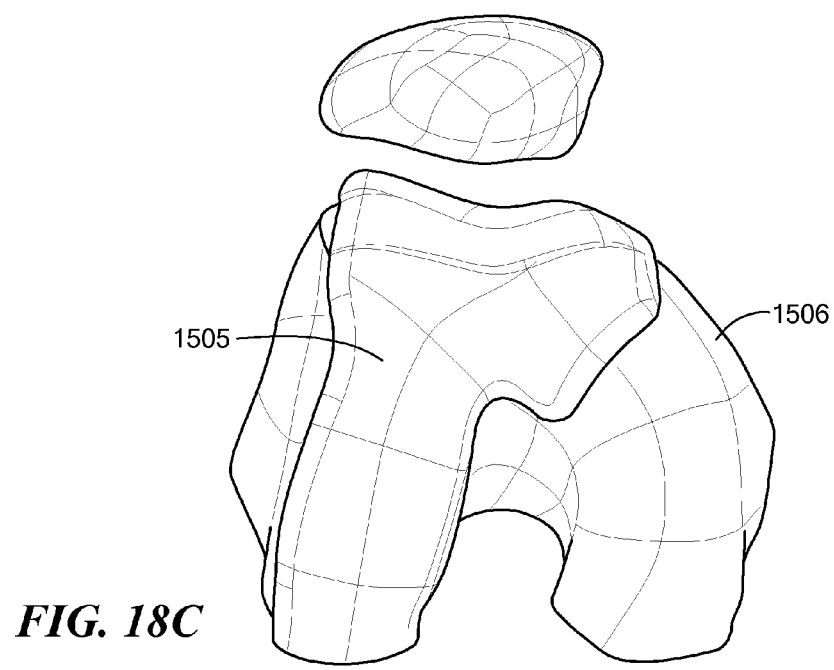
FIG. 18C

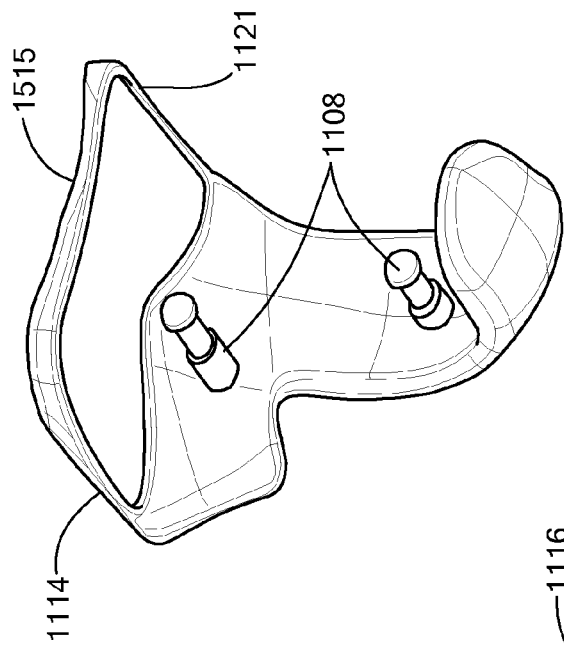
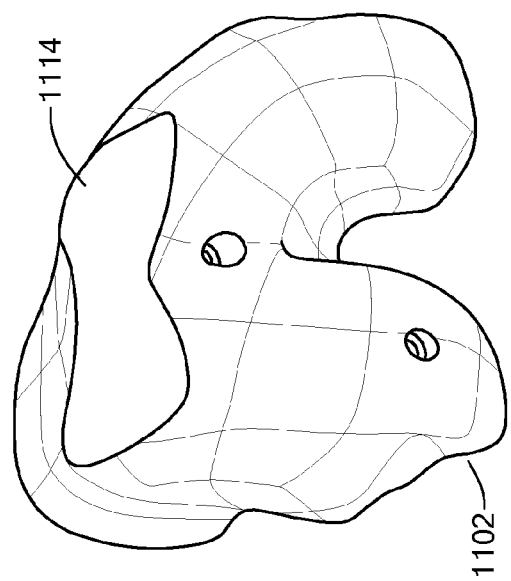
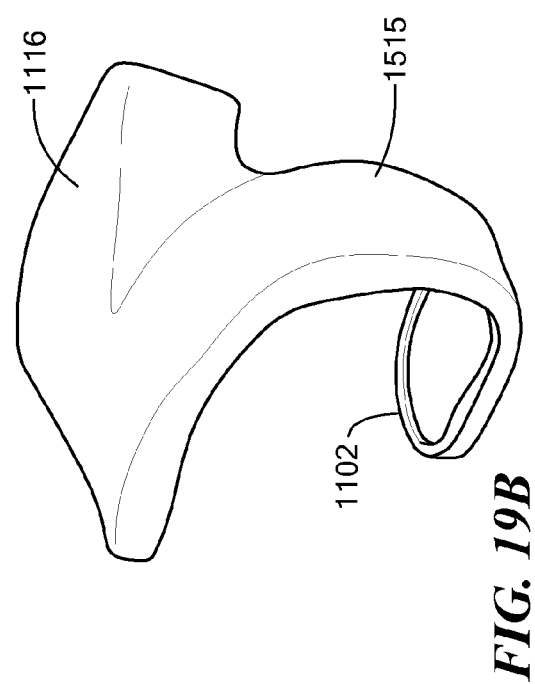
FIG. 19A
FIG. 19B
FIG. 19C

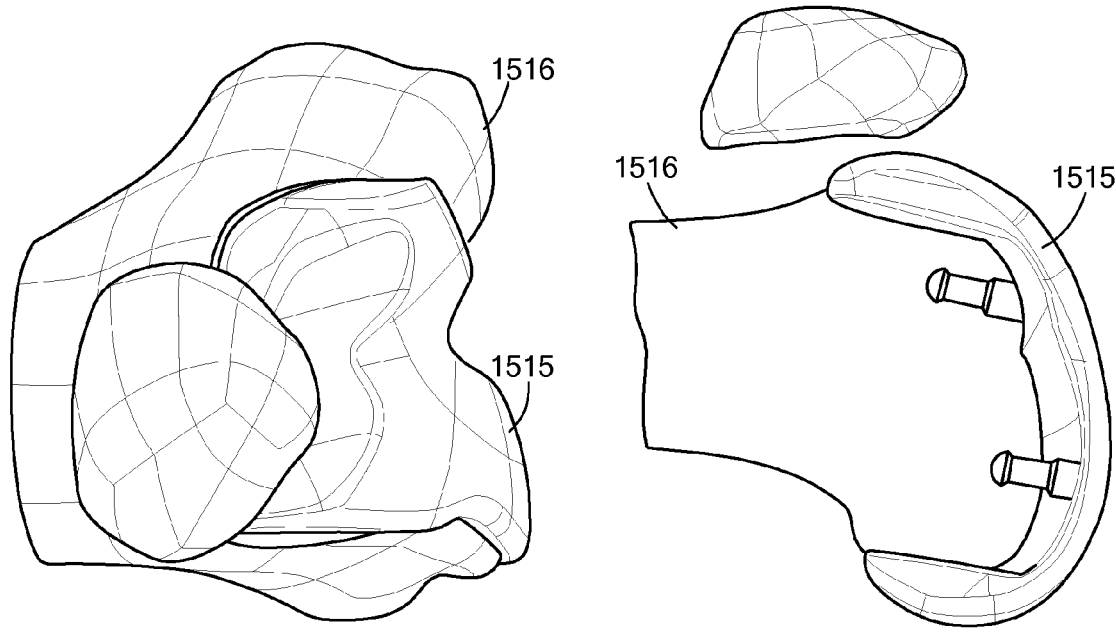
*FIG. 20A*
*FIG. 20B*
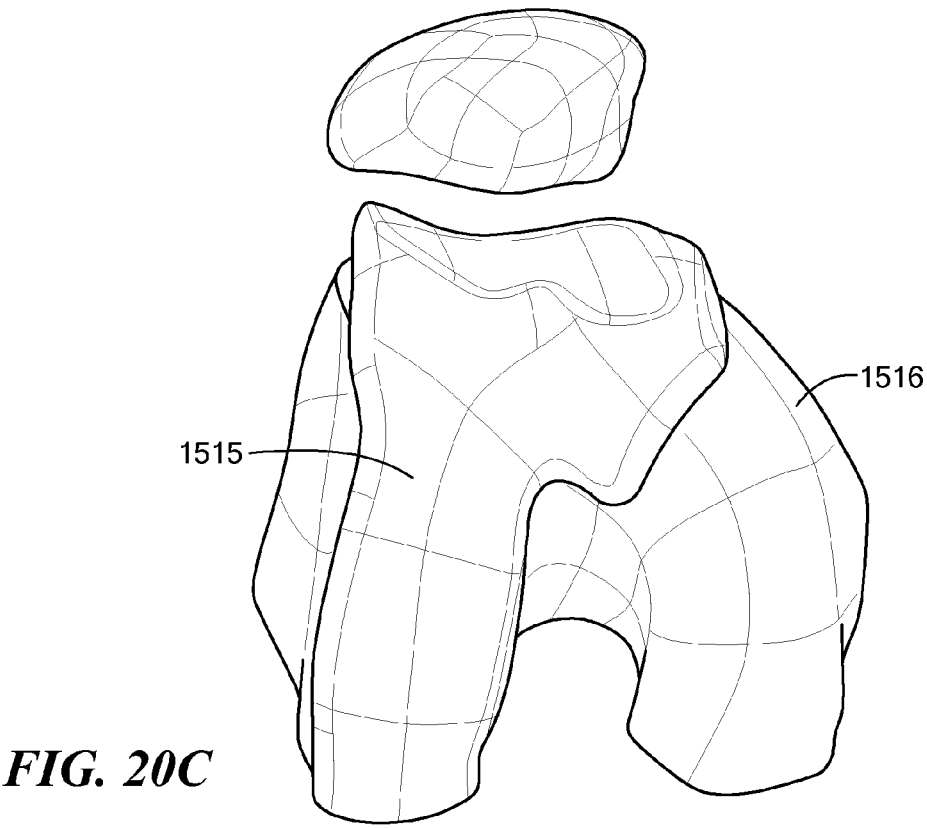
*FIG. 20C*

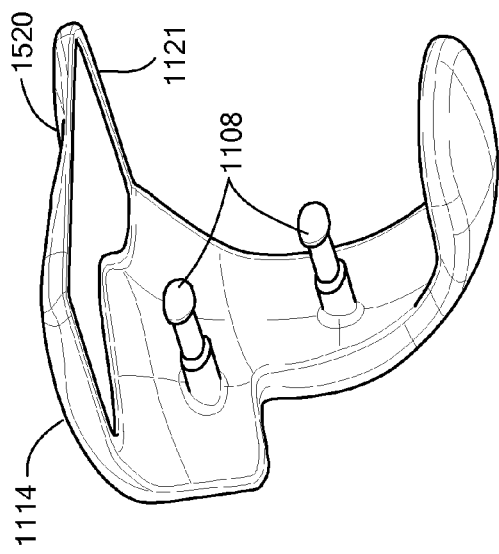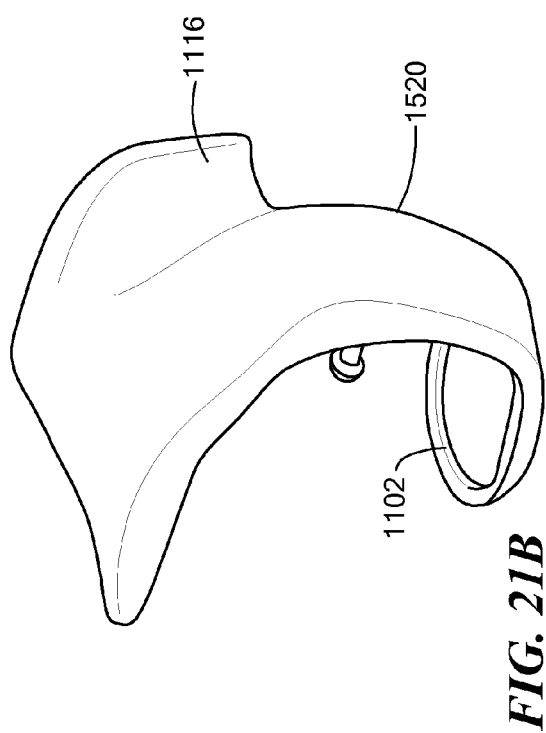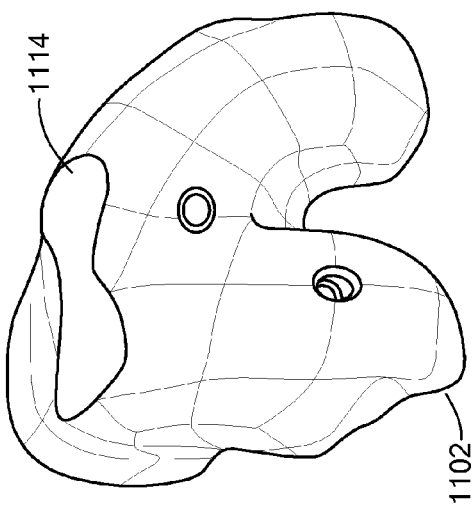
FIG. 21C
FIG. 21B
FIG. 21A

PATIENT-SPECIFIC AND PATIENT-ENGINEERED ORTHOPEDIC IMPLANTS

CROSS REFERENCE TO RELATED APPLICATIONS

This application claims priority to U.S. Ser. No. 61/284,022, filed Dec. 11, 2009, entitled "Patient-Specific and Patient-Engineered Orthopedic Implants."

This application also is a continuation-in-part of U.S. patent application Ser. No. 10/752,438, entitled "Patient Selectable Knee Joint Arthroplasty Devices," filed Jan. 5, 2004.

The above patent applications, and patent applications and other references mentioned herein below, are hereby incorporated by reference in their entities.

TECHNICAL FIELD

The present invention relates to orthopedic methods, systems and devices and more particularly, to joint implants and methods for designing and manufacturing the same.

BACKGROUND

Traditional joint implants are known in the art. For example, one of the most common types of joint prosthetic devices is a knee implant including a femoral component and a tibial component. Other joint implants are associated with, for example, the hip and shoulder.

Implantation of traditional prosthetic devices is usually associated with loss of underlying tissue and bone. With some devices, serious long-term complications associated with the loss of significant amount of tissue and bone can include infection, osteolysis and also loosening of the implant. Such joint arthroplasties can be highly invasive and require surgical resection of the entire, or a majority of the, articular surface of one or more bones involved in the repair. Typically with these procedures, the marrow space is fairly extensively reamed in order to fit the stem of the prosthesis within the bone. Reaming results in a loss of a patient's bone stock and over time subsequent osteolysis can frequently lead to loosening of the prosthesis. Further, the area where the implant and the bone mate degrades over time requiring the prosthesis to eventually be replaced. Since the patient's bone stock is limited, the number of possible replacement surgeries also is limited for joint arthroplasty. In short, over the course of fifteen to twenty years, and in some cases even shorter time periods, the patient can run out of therapeutic options ultimately resulting in a painful, non-functional joint.

Moreover, currently available traditional implants can be misaligned with a patient's anatomical structures and thereby jeopardize the resultant joint congruity. Poor alignment and poor joint congruity can, for example, lead to instability of the joint. Further, traditional implant solutions do not take into account the fact that roughly 80% of patients undergoing knee surgery have a healthy lateral compartment and only need to repair the medial condyle and the patella. An additional 10% only have damage to the lateral condyle. Thus, 90% of patients do not require the entire condylar surface repaired.

Thus, there is a need for joint implants and systems that integrate with a patient's anatomical structures. In particular, there is a need for implants and implant systems that take into account the patient-specific damage to be repaired and minimizes bone loss due to implantation requirements. Moreover, there is a need for implants and implant systems that provide an improved functional joint and improve the anatomic result of the joint correction procedure by providing surfaces that more closely resemble, or optimize, the joint anatomy of a patient.

SUMMARY

Some embodiments described herein provide novel devices and methods for replacing a portion (for example, a diseased area and/or area slightly larger than the diseased area) of a joint (for example, one or more of cartilage, meniscus and bone) with one or more implants, where the implant(s) achieve an anatomic, near anatomic, and/or optimized fit with the surrounding structures and tissues. In cases where the devices and/or methods include an element associated with the underlying articular bone, some embodiments also provide that the bone-associated element can achieve a near anatomic alignment with the subchondral bone. In addition, some embodiments provide for the preparation of an implantation site with one or more cuts. Asymmetrical components can also be provided to improve the anatomic functionality of the repaired joint by providing a solution that closely resembles the natural knee joint anatomy or an optimized knee joint anatomy. The improved anatomic results, in turn, leads to an improved functional result for the repaired joint. Some embodiments also provide a kit that includes one or more implants used to achieve optimal joint correction.

In certain aspects, implants and methods are provided for a joint of one or more of the knee, hip, ankle, shoulder, elbow, wrist, and hand. In certain embodiments, the implant devices and methods may be used for knee implants and procedures in a bicompartmental arthroplasty that covers portions or all of one femoral condyle, medial or lateral, and the trochlea. These devices may be fixed or non-mobile bearing or they can be mobile bearing.

BRIEF DESCRIPTION OF THE DRAWINGS

FIGS. 2A-2S depict an implant suitable for placement on the femoral condyle. FIG. 2A is a top view of the inferior surface of the implant showing a chamfer cut. FIG. 2B is a slightly perspective view of the superior surface of the implant. FIG. 2C is a perspective side view of the implant from a first direction. FIGS. 2P-S illustrate alternative embodiments of the implant having one or more cuts.

FIGS. 12A-J depict a whole patella (FIG. 12A) and a patella that has been cut in order to install an implant (FIG. 12B). A top view and a side view of a suitable patella implant are shown in FIGS. 12C-D superimposed on a patella to illustrate the location of the implant dome relative to the patellar ridge. FIGS. 12E-F illustrate the implant superimposed over a patella. FIGS. 12G-J illustrate an alternate design for the patella implant based on a blank (FIG. 12G).

FIG. 13A depicts the knee with a condyle implant and a patella implant. FIG. 13B depicts an alternate view of the knee with a condyle implant and a patella implant wherein the condyle implant covers a greater portion of the surface of the condyle in the posterior direction. FIG. 13C illustrates a knee joint wherein the implant is provided on the condyle, the patella and the tibial plateau.

FIG. 14A depicts the knee with a tibial implant. FIG. 14B depicts the knee with a condyle implant. FIG. 14C depicts a knee with a tibial implant and a condyle implant. FIG. 14C depicts a knee with a bicompartmental condyle implant and a tibial implant.

FIGS. 16A-16C illustrate the implant of FIGS. 15C-15E in place on a femur.

FIGS. 18A-18C illustrate the implant of FIGS. 17A-17C in place on a femur.

FIGS. 19A-19C illustrate an implant design and bone resectioning for a bicompartmental implant that includes posterior and anterior bone cuts and that was engineered to optimize trochlear groove fit with a patellar implant component.

FIGS. 20A-20C illustrate the implant of FIGS. 19A-19C in place on a femur.

FIGS. 21A-21C illustrate an implant design and bone resectioning for a bicompartmental implant that includes posterior and anterior bone cuts, was engineered to optimize trochlear groove fit with a patellar implant component, and that includes a different flex-cut than the design of FIGS. 19A-19C.

DETAILED DESCRIPTION

Figure 1A:
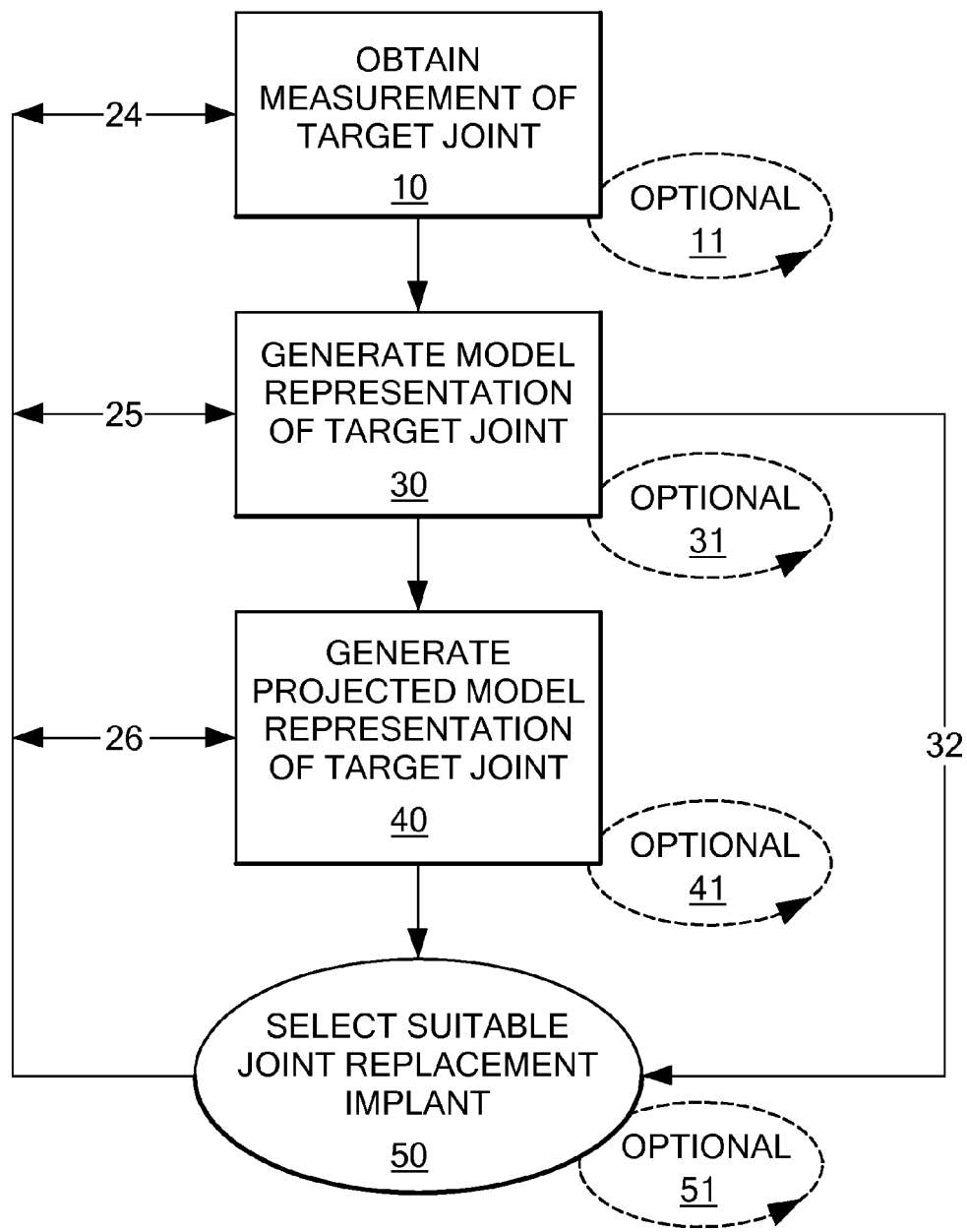
FIG. 1A is a block diagram of a method for assessing a joint in need of repair wherein the existing joint surface is unaltered, or substantially unaltered, prior to receiving the selected implant.

As will be appreciated by those of skill in the art, methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed. Also, it is contemplated that any optional feature described herein may be set forth and claimed independently, or in combination with any one or more of the features described herein.

Methods and compositions described herein can employ, unless otherwise indicated, images derived from conventional and digital methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. Such techniques are explained fully in the literature and need not be described herein. See, for example, X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher. See also, The Essential Physics of Medical Imaging (2nd Ed.), Jerrold T. Bushberg, et al.

Some embodiments described herein provide methods and compositions for repairing joints, particularly for repairing articular cartilage and for facilitating the integration of a wide variety of cartilage repair materials into a subject. Among other things, certain techniques described herein allow for the customization of cartilage repair material to suit a particular subject, for example in terms of size, cartilage thickness and/or curvature. When the shape (e.g., size, thickness and/or curvature) of the articular cartilage surface is an exact or near anatomic fit with the non-damaged cartilage or with the subject's original cartilage, the success of repair is enhanced. The repair material can be shaped prior to implantation and such shaping can be based, for example, on electronic images that provide information regarding curvature or thickness of any "normal" cartilage surrounding the defect and/or on curvature of the bone underlying the defect. Thus, some embodiments provide, among other things, for minimally invasive methods for partial joint replacement. The methods require only minimal or, in some instances, no loss in bone stock. Additionally, unlike traditional implants and related techniques, certain methods described herein help to restore the integrity of the articular surface by achieving an exact or near anatomic match between the implant and the surrounding or adjacent cartilage and/or subchondral bone.

Some embodiments described herein provide methods and compositions for repairing joints that includes cutting or resecting one or more portions of a patient's bone, for example, subchondral bone. Among other things, certain implants and techniques described herein provide implants and implant components that include one or more patient-specific and/or patient-engineered surfaces that are customized for a patient, for example in terms of size, thickness and/or curvature, to supply an anatomic, near anatomic, and/or optimized fit with one or more of the patient's anatomical structures and/or a structure of another implant component. The patient-specific and/or patient-engineered aspects or features of an implant can be shaped prior to implantation and can be based on patient-specific data, for example, as obtained via electronic images of the patient's anatomical features. In this way, unlike traditional implants and related techniques, certain methods described herein help to restore or optimize a patient's joint by achieving an anatomic, near anatomic, or optimized match between the implant or implant component and one or more other structures in the joint.

Advantages of embodiments described herein can include, but are not limited to, (i) customization of joint repair, thereby enhancing the efficacy and comfort level for the patient following the repair procedure; (ii) eliminating the need for a surgeon to measure the defect to be repaired intraoperatively in some embodiments; (iii) eliminating the need for a surgeon to shape the material during the implantation procedure; (iv) providing methods of evaluating curvature of the repair material based on bone or tissue images or based on intraoperative probing techniques; (v) providing methods of repairing joints with only minimal or, in some instances, no loss in bone stock; (vi) improving postoperative joint congruity; (vii) improving the postoperative patient recovery in some embodiments and (viii) improving postoperative function, such as range of motion.

Thus, the methods described herein allow for the design and use of joint repair material that more precisely fits the defect (for example, site of implantation) or the articular surface(s) and, accordingly, provides improved repair of the joint.

1. Assessment of Joints and Alignment

The methods and compositions described herein can be used to treat defects resulting from disease of the cartilage (for example, osteoarthritis), bone damage, cartilage damage, trauma, and/or degeneration due to overuse or age. Some embodiments allow, among other things, a health practitioner to evaluate and treat such defects. The size, volume and shape of the area of interest can include only the region of cartilage that has the defect, but preferably include contiguous parts of the cartilage surrounding the cartilage defect.

As will be appreciated by those of skill in the art, size, curvature and/or thickness measurements can be obtained using any suitable technique. For example, one-dimensional, two-dimensional, and/or three-dimensional measurements can be obtained using suitable mechanical means, laser devices, electromagnetic or optical tracking systems, molds, materials applied to the articular surface that harden and "memorize the surface contour," and/or one or more imaging techniques known in the art. Measurements can be obtained non-invasively and/or intraoperatively (for example, using a probe or other surgical device). As will be appreciated by those of skill in the art, the thickness of the repair device can vary at any given point depending upon patient's anatomy and/or the depth of the damage to the cartilage and/or bone to be corrected at any particular location on an articular surface.

FIG. 1A is a flow chart showing steps taken by a practitioner in assessing a joint. First, a practitioner obtains a measurement of a target joint 10. The step of obtaining a measurement can be accomplished by taking an image of the joint. This step can be repeated, as necessary 11 to obtain a plurality of images in order to further refine the joint assessment process. Once the practitioner has obtained the necessary measurements, the information is used to generate a model representation of the target joint being assessed 30. This model representation can be in the form of a topographical map or image. The model representation of the joint can be in one, two, or three dimensions. It can include a physical model. More than one model can be created 31, if desired. Either the original model or a subsequently created model, or both, can be used. After the model representation of the joint is generated 30, the practitioner can optionally generate a projected model representation of the target joint in a corrected condition 40, for example, from the existing cartilage on the joint surface, or by providing a substantially negatively matching surface for the opposing joint surface, or a combination thereof. This step can be repeated 41 as necessary or desired. Using the difference between the topographical condition of the joint and the projected image of the joint, the practitioner can then select a joint implant 50 that is suitable to achieve the corrected joint anatomy. As will be appreciated by those of skill in the art, the selection process 50 can be repeated 51 as often as desired to achieve the desired result. Additionally, it is contemplated that a practitioner can obtain a measurement of a target joint 10 by obtaining, for example, an x-ray, and then select a suitable joint replacement implant 50.

As will be appreciated by those of skill in the art, the practitioner can proceed directly from the step of generating a model representation of the target joint 30 to the step of selecting a suitable joint replacement implant 50 as shown by the arrow 32. Additionally, following selection of suitable joint replacement implant 50, one or more of the steps of obtaining measurement of target joint 10, generating model representation of target joint 30, and generating projected model 40, can be repeated in series or in parallel as shown by the flow 24, 25, 26.

Figure 1B:
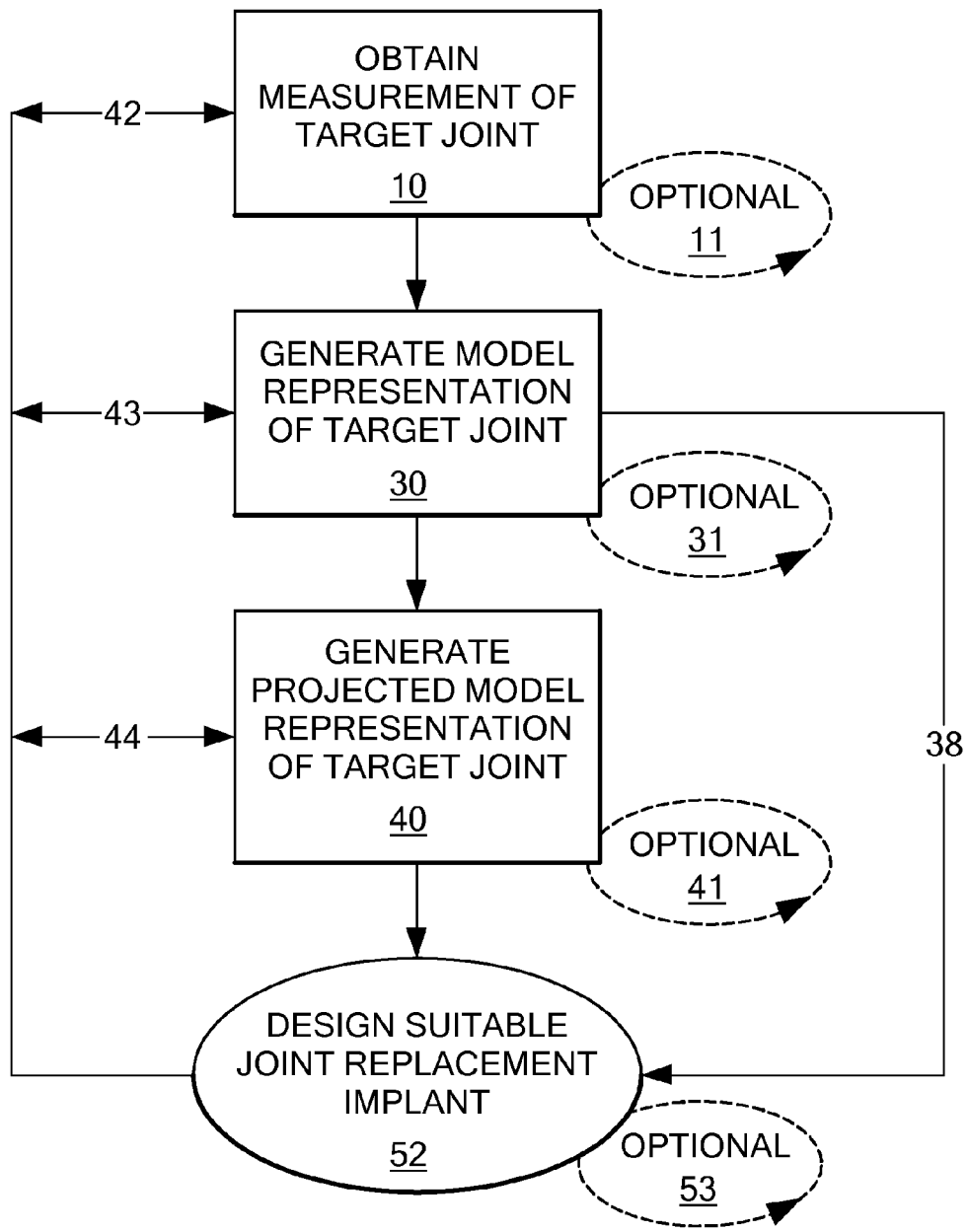
FIG. 1B is a block diagram of a method for assessing a joint in need of repair wherein the existing joint surface is unaltered, or substantially unaltered, prior to designing an implant suitable to achieve the repair.

FIG. 1B is an alternate flow chart showing steps taken by a practitioner in assessing a joint. First, a practitioner obtains a measurement of a target joint 10. The step of obtaining a measurement can be accomplished by taking an image of the joint. This step can be repeated, as necessary 11 to obtain a plurality of images in order to further refine the joint assessment process. Once the practitioner has obtained the necessary measurements, the information is used to generate a model representation of the target joint being assessed 30. This model representation can be in the form of a topographical map or image. The model representation of the joint can be in one, two, or three dimensions. The process can be repeated 31 as necessary or desired. It can include a physical model. After the model representation of the joint is assessed 30, the practitioner optionally can generate a projected model representation of the target joint in a corrected condition 40. This step can be repeated 41 as necessary or desired. Using the difference between the topographical condition of the joint and the projected image of the joint, the practitioner then can design a joint implant 52 that is suitable to achieve the corrected joint anatomy, repeating the design process 53 as often as necessary to achieve the desired implant design. The practitioner also can assess whether providing additional features, such as rails, keels, lips, pegs, cruciate stems, or anchors, cross-bars, and/or other features will enhance the implant's performance in the target joint.

As will be appreciated by those of skill in the art, the practitioner can proceed directly from the step of generating a model representation of the target joint 30 to the step of designing a suitable joint replacement implant 52 as shown by the arrow 38. Following the design of a suitable joint replacement implant 52, one or more of the steps of obtaining measurement of target joint 10, generating model representation of target joint 30, and generating projected model 40, can be repeated in series or parallel as shown by the flow 42, 43, 44.

Figure 1C:
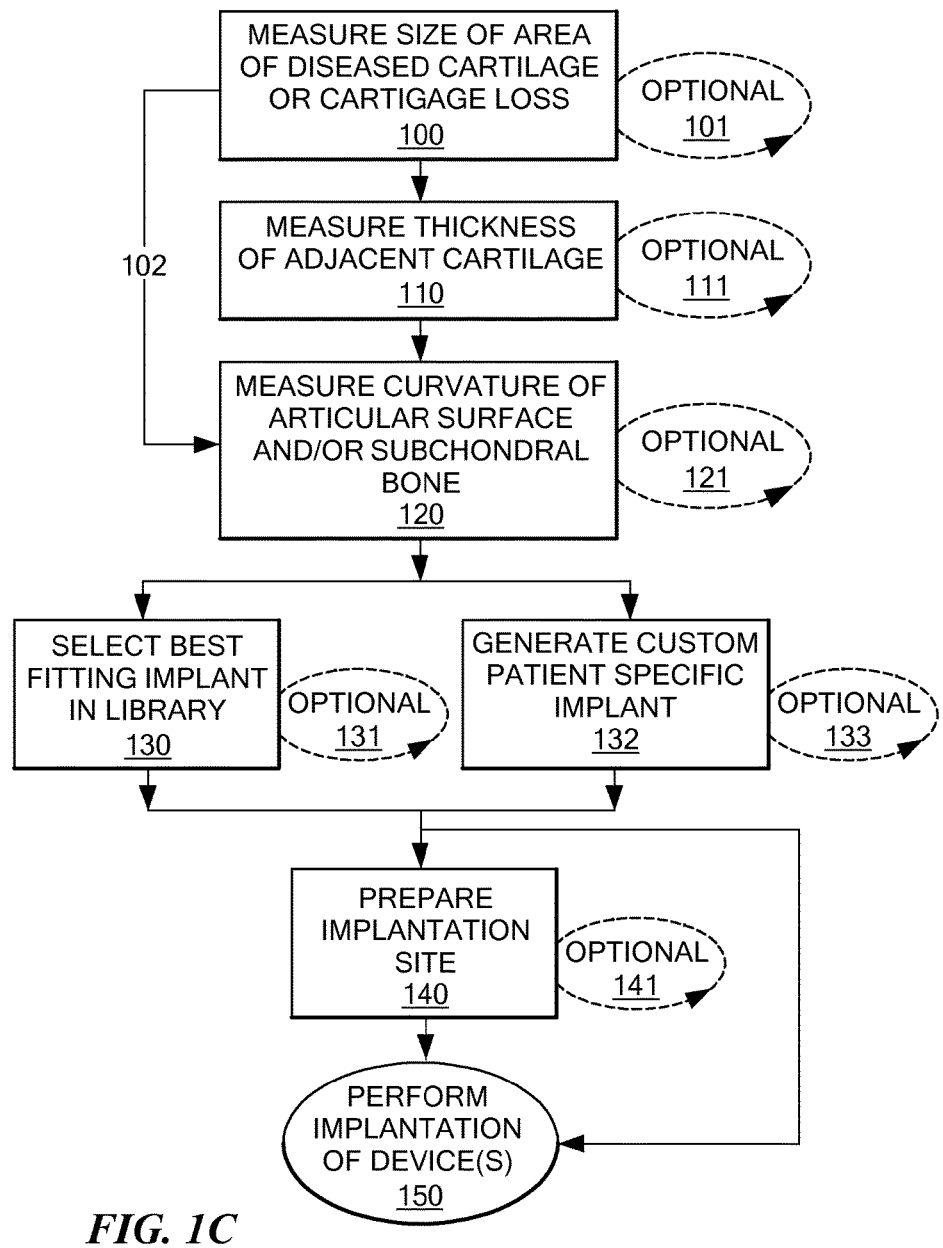
FIG. 1C is a block diagram of a method for developing an implant and using the implant in a patient.

FIG. 1C is a flow chart illustrating the process of selecting an implant for a patient. First, using the techniques described above or those suitable and known in the art, the size of area of diseased cartilage or cartilage loss is measured 100. This step can be repeated multiple times 101, as desired. Once the size of the cartilage defect is measured, the thickness of adjacent cartilage can optionally be measured 110. This process also can be repeated as desired 111. Either after measuring the cartilage loss or after measuring the thickness of adjacent cartilage, the curvature of the articular surface is then measured 120. Alternatively, the subchondral bone can be measured. As will be appreciated measurements can be taken of the surface of the joint being repaired, or of the mating surface in order to facilitate development of the best design for the implant surface. This process also can be repeated as desired 121.

Once the surfaces have been measured, the user either selects the best fitting implant contained in a library of implants 130 or generates a patient-specific implant 132. In addition, patient-specific cuts to the patient's bone optionally can be designed and an implant having the corresponding bone cut angles and surfaces can be selected or generated. These steps can be repeated as desired or necessary to achieve the best fitting implant for a patient, 131, 133. As will be appreciated by those of skill in the art, the process of selecting or designing an implant can be tested against the information contained in the MRI or x-ray of the patient to ensure that the surfaces of the device achieves a good fit relative to the subject's joint surface. Testing can be accomplished by, for example, superimposing the implant image over the image for the subject's joint. Once it has been determined that a suitable implant has been selected or designed, the implant site can be prepared 140, for example by removing cartilage or bone from the joint surface, or the implant can be placed into the joint 150.

The joint implant selected or designed achieves anatomic, near anatomic, and/or optimized fit with the modified and/or unmodified articular surface of the patient's joint while presenting a mating surface for the opposing joint surface that replicates the natural joint anatomy or an optimized joint anatomy. Both the existing surface of the joint can be assessed as well as the desired resulting surface of the joint. This technique is particularly useful for implants that are not anchored into the bone.

As will be appreciated by those of skill in the art, the physician, or practitioner can obtain a measurement of a target joint 10 and then either design 52 or select 50 a suitable joint replacement implant.

2. Repair Materials

A wide variety of materials can be used in the practice of the implants described herein, including, but not limited to, plastics, metals, crystal free metals, ceramics, biological materials (for example, collagen or other extracellular matrix materials), hydroxyapatite, cells (for example, stem cells, chondrocyte cells or the like), or combinations thereof. Based on the obtained information, such as measurements, regarding the defect and the articular surface and/or the subchondral bone, a repair material can be formed or selected. Further, using one or more of the techniques described herein, a cartilage replacement or regenerating material can a curvature that fits into a particular cartilage defect, follows the contour and shape of the articular surface, and/or matches the thickness of the surrounding cartilage. The repair material can include any combination of materials, and typically includes at least one non-pliable material, for example materials that are not easily bent or changed.

2.1 Metal and Polymeric Repair Materials

Currently, joint repair systems often employ metal and/or polymeric materials including, for example, prostheses which are anchored into the underlying bone (e.g., a femur in the case of a knee prosthesis). See, e.g., U.S. Pat. No. 6,203,576 to Afriat, et al. issued Mar. 20, 2001 and U.S. Pat. No. 6,322,588 to Ogle, et al. issued Nov. 27, 2001, and references cited therein. Various metals can be selected based on any criteria known in the art. For example, material selection can be based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-chromium-nickel alloy, and MP35N, a nickel-cobalt-chromium-molybdenum alloy, and Nitinol™, a nickel-titanium alloy, aluminum, manganese, iron, tantalum, crystal free metals, such as Liquidmetal® alloys (available from LiquidMetal Technologies, www.liquidmetal.com), other metals that can slowly form polyvalent metal ions, for example to inhibit calcification of implanted substrates in contact with a patient's bodily fluids or tissues, and combinations thereof.

Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers can also be used.

Other appropriate materials include, for example, the polyketone known as polyetheretherketone (PEEK™). This includes the material PEEK 450G, which is an unfilled PEEK approved for medical implantation available from Victrex of Lancashire, Great Britain. (Victrex is located at the web site, www.matweb.com, or see Boedeker at the web site, www.boedeker.com). Other sources of this material include Gharda located in Panoli, India (www.ghardapolymers.com).

It should be noted that the material selected also can be filled. For example, other grades of PEEK also are available and contemplated, such as 30% glass-filled or 30% carbon filled, provided such materials are cleared for use in implantable devices by the FDA or other regulatory body. Glass filled PEEK reduces the expansion rate and increases the flexural modulus of PEEK relative to that portion which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

As will be appreciated, other suitable similarly biocompatible thermoplastic or thermoplastic polycondensate materials that resist fatigue, have good memory, are flexible, and/or deflectable have very low moisture absorption, and good wear and/or abrasion resistance, can be used. The implant can also be comprised of polyetherketoneketone (PEKK).

Other materials that can be used include polyetherketone (PEK), polyetherketoneetherketoneketone (PEKEKK), and polyetheretherketoneketone (PEEKK), and generally a polyaryletheretherketone. Further, other polyketones can be used as well as other thermoplastics.

Reference to appropriate polymers that can be used for the implant can be made to the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

The polymers can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. The substrate can be textured or made porous by either physical abrasion or chemical alteration to facilitate incorporation of the metal coating. Other processes are also appropriate, such as extrusion, injection, compression molding and/or machining techniques. Typically, the polymer is chosen for its physical and mechanical properties and is suitable for carrying and spreading the physical load between the joint surfaces.

More than one metal and/or polymer can be used in combination. For example, one or more metal-containing substrates can be coated with polymers in one or more regions or, alternatively, one or more polymer-containing substrates can be coated in one or more regions with one or more metals.

The system or prosthesis can be porous or porous coated. The porous surface components can be made of various materials including metals, ceramics, and polymers. These surface components can, in turn, be secured by various means to a multitude of structural cores formed of various metals. Suitable porous coatings include, but are not limited to, metal, ceramic, and polymeric (e.g., biologically neutral elastomers such as silicone rubber, polyethylene terephthalate and/or combinations thereof) coatings or combinations thereof. See, e.g., U.S. Pat. No. 3,605,123 to Hahn, issued Sep. 20, 1971. U.S. Pat. No. 3,808,606 to Tronzo issued May 7, 1974 and U.S. Pat. No. 3,843,975 to Tronzo issued Oct. 29, 1974; U.S. Pat. No. 3,314,420 to Smith issued Apr. 18, 1967; U.S. Pat. No. 3,987,499 to Scharbach issued Oct. 26, 1976; and German Offenlegungsschrift 2,306,552. There can be more than one coating layer and the layers can have the same or different porosities. See, e.g., U.S. Pat. No. 3,938,198 to Kahn, et al., issued Feb. 17, 1976.

The coating can be applied by surrounding a core with powdered polymer and heating until cured to form a coating with an internal network of interconnected pores. The tortuosity of the pores (e.g., a measure of length to diameter of the paths through the pores) can be important in evaluating the probable success of such a coating in use on a prosthetic device. See, also, U.S. Pat. No. 4,213,816 to Morris issued Jul. 22, 1980. The porous coating can be applied in the form of a powder and the article as a whole subjected to an elevated temperature that bonds the powder to the substrate. Selection of suitable polymers and/or powder coatings can be determined in view of the teachings and references cited herein, for example based on the melt index of each.

2.2 Biological Repair Material

Repair materials can also include one or more biological material, either alone or in combination with non-biological materials. For example, any base material can be designed or shaped and suitable cartilage replacement or regenerating material(s) such as fetal cartilage cells can be applied to be the base. The cells then can be grown in conjunction with the base until the thickness (and/or curvature) of the cartilage surrounding the cartilage defect has been reached. Conditions for growing cells (e.g., chondrocytes) on various substrates in culture, ex vivo and in vivo are described, for example, in U.S. Pat. No. 5,478,739 to Slivka et al. issued Dec. 26, 1995; U.S. Pat. No. 5,842,477 to Naughton et al. issued Dec. 1, 1998; U.S. Pat. No. 6,283,980 to Vibe-Hansen et al., issued Sep. 4, 2001, and U.S. Pat. No. 6,365,405 to Salzmann et al. issued Apr. 2, 2002. Non-limiting examples of suitable substrates include plastic, tissue scaffold, a bone replacement material (e.g., a hydroxyapatite, a bioresorbable material), or any other material suitable for growing a cartilage replacement or regenerating material on it.

Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers can be bioresorbable.

Biological materials used in the methods described herein can be autografts (from the same subject), allografts (from another individual of the same species), and/or xenografts (from another species). See, also, International Patent Publications WO 02/22014 to Alexander et al. published Mar. 21, 2002 and WO 97/27885 to Lee published Aug. 7, 1997. In certain embodiments, autologous materials are preferred, as they can carry a reduced risk of immunological complications to the host, including re-absorption of the materials, inflammation and/or scarring of the tissues surrounding the implant site.

In certain embodiments, a probe is used to harvest tissue from a donor site and to prepare a recipient site. The donor site can be located in a xenograft, an allograft or an autograft. The probe is used to achieve a good anatomic match between the donor tissue sample and the recipient site. The probe is specifically designed to achieve a seamless or near seamless match between the donor tissue sample and the recipient site. The probe can, for example, be cylindrical. The distal end of the probe is typically sharp in order to facilitate tissue penetration. Additionally, the distal end of the probe is typically hollow in order to accept the tissue. The probe can have an edge at a defined distance from its distal end, e.g. at 1 cm distance from the distal end and the edge can be used to achieve a defined depth of tissue penetration for harvesting. The edge can be external or can be inside the hollow portion of the probe. For example, an orthopedic surgeon can take the probe and advance it with physical pressure into the cartilage, the subchondral bone and the underlying marrow in the case of a joint such as a knee joint. The surgeon can advance the probe until the external or internal edge reaches the cartilage surface. At that point, the edge can prevent further tissue penetration thereby achieving a constant and reproducible tissue penetration. The distal end of the probe can include one or more blades, saw-like structures, or tissue cutting mechanism. For example, the distal end of the probe can include an iris-like mechanism consisting of several small blades. The blade or blades can be moved using a manual, motorized or electrical mechanism thereby cutting through the tissue and separating the tissue sample from the underlying tissue. Typically, this can be repeated in the donor and the recipient. In the case of an iris-shaped blade mechanism, the individual blades can be moved so as to close the iris thereby separating the tissue sample from the donor site.

In certain other embodiments, a laser device or a radiofrequency device can be integrated inside the distal end of the probe. The laser device or the radiofrequency device can be used to cut through the tissue and to separate the tissue sample from the underlying tissue.

In certain embodiments, the same probe can be used in the donor and in the recipient. In certain other embodiments, similarly shaped probes of slightly different physical dimensions can be used. For example, the probe used in the recipient can be slightly smaller than that used in the donor thereby achieving a tight fit between the tissue sample or tissue transplant and the recipient site. The probe used in the recipient can also be slightly shorter than that used in the donor thereby correcting for any tissue lost during the separation or cutting of the tissue sample from the underlying tissue in the donor material.

Any biological repair material can be sterilized to inactivate biological contaminants such as bacteria, viruses, yeasts, molds, mycoplasmas and parasites. Sterilization can be performed using any suitable technique, for example radiation, such as gamma radiation.

Any of the biological materials described herein can be harvested with use of a robotic device. The robotic device can use information from an electronic image for tissue harvesting.

In certain embodiments, the cartilage replacement material has a particular biochemical composition. For instance, the biochemical composition of the cartilage surrounding a defect can be assessed by taking tissue samples and chemical analysis or by imaging techniques. For example, WO 02/22014 to Alexander describes the use of gadolinium for imaging of articular cartilage to monitor glycosaminoglycan content within the cartilage. The cartilage replacement or regenerating material can then be made or cultured in a manner, to achieve a biochemical composition similar to that of the cartilage surrounding the implantation site. The culture conditions used to achieve the desired biochemical compositions can include, for example, varying concentrations. Biochemical composition of the cartilage replacement or regenerating material can, for example, be influenced by controlling concentrations and exposure times of certain nutrients and growth factors.

3. Implant Components

Information on thickness and curvature of the cartilage and/or subchondral bone can be used to create a physical model of the surfaces of the articular cartilage and/or of the underlying bone. This physical model can be representative of a limited area within the joint or it can encompass the entire joint. This model can also take into consideration the presence or absence of a meniscus as well as the presence or absence of some or all of the cartilage. For example, in the knee joint, the physical model can encompass only the medial or lateral femoral condyle, both femoral condyles and the notch region, the medial tibial plateau, the lateral tibial plateau, the entire tibial plateau, the medial patella, the lateral patella, the entire patella or the entire joint. The location of a diseased area of cartilage can be determined, for example using a 3D coordinate system or a 3D Euclidian distance as described in WO 02/22014.

In this way, the size of the defect to be repaired can be determined. This process takes into account that, for example, roughly 80% of patients have a healthy lateral component. As will be apparent, some, but not all, defects can include less than the entire cartilage. Thus, in certain embodiments, the thickness of the normal or only mildly diseased cartilage surrounding one or more cartilage defects is measured. This thickness measurement can be obtained at a single point or, preferably, at multiple points, for example 2 point, 4-6 points, 7-10 points, more than 10 points or over the length of the entire remaining cartilage. Furthermore, once the size of the defect is determined, an appropriate therapy, for example, a repair system (also referred to as an articular repair system), including one or more implants or implant components, can be selected such that as much as possible of the healthy, surrounding tissue is preserved.

In certain embodiments, the curvature of the articular surface can be measured to select, design, and/or shape the repair material. Further, both the thickness of the remaining cartilage and the curvature of the articular surface can be measured to design and/or shape the repair material. Alternatively, the curvature of the subchondral bone can be measured and the resultant measurement(s) can be used to select, design, and/or shape a replacement material. For example, the contour of the subchondral bone can be used to re-create a virtual implant surface. The subchondral bone shape in the diseased areas can be measured. A virtual contour then can be created by projecting the subchondral bone surface into the cartilage surface, whereby the projected subchondral bone surface establishes the margins of the implant. In shaping the device, the contours can be configured to mate with existing anatomical structures or to account for the removal of anatomical structures.

3.1 Femoral Bicompartmental Implant Component

This section and the following subsections describe various features of embodiments of a bicompartmental implant or implant device 500. In the design and manufacture of these embodiments, the measurements for one or more aspects or features of any embodiment can be patient-specific, engineered, patient-engineered, or standard. It is understood that any of the patient-specific, engineered, patient-engineered, and/or standard aspects or features described below can be combined in an embodiment.

FIGS. 2A-2V illustrate a type of implant or implant component suitable for repairing a damaged condyle as disclosed herein. As shown in FIG. 2A, the implant 500 is configured such that it covers only one of the lateral or medial femoral condyles 510. The implant also covers at least a portion of the patellar surface of the femur 512. Accordingly, since this type of implant covers two compartments of the femoral aspect of the knee, it is referred to as a bicompartmental implant or implant component.

The implant optionally can oppose one or more implants or opposing joint surfaces. FIG. 2C is a perspective side view of the implant of FIG. 2A. As shown in FIG. 2C, the superior surface 502 of the implant 500 is curved to correspond to the curvature of the femoral condyle that it mates with and the portion of the patellar surface of the femur that it covers. One or more pegs 530 can be provided to assist in anchoring the implant to the bone. Additionally, as described more fully below, one or more angled surface(s) 503 can be provided on an superior surface 502 of the condyle component that conforms to an optionally provided cut made on the surface of the joint surface with which the implant mates.

Figure 2D:
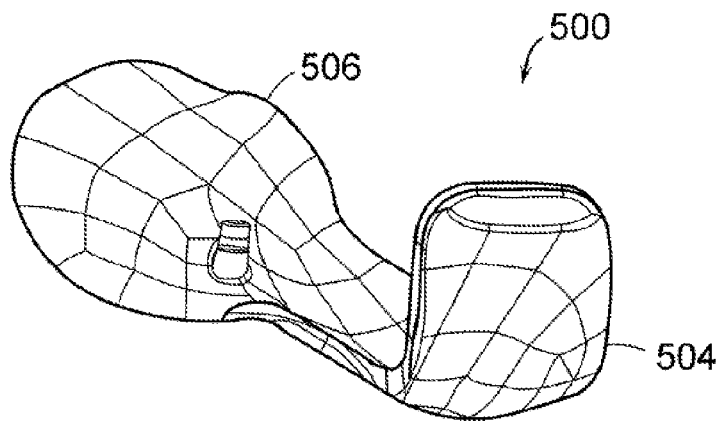
FIG. 2D is a slightly perspective side view of the implant from a second direction.

FIG. 2D illustrates a perspective top view of the implant 500 shown in FIG. 2A. As is appreciated from this view, the inferior surface 504 of the implant 500 is configured to conform to the projected shape of the femoral condyles, e.g., the shape healthy femoral condyles would present to the tibial surface in a non-damaged joint.

Figure 2E:
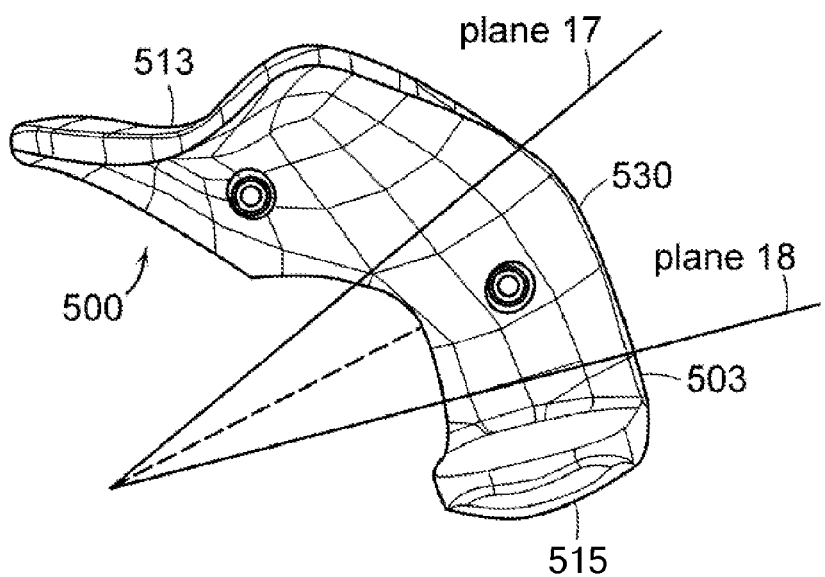
FIGS. 2E-F are side views of the implant showing the bearing loads.
Figure 2F:
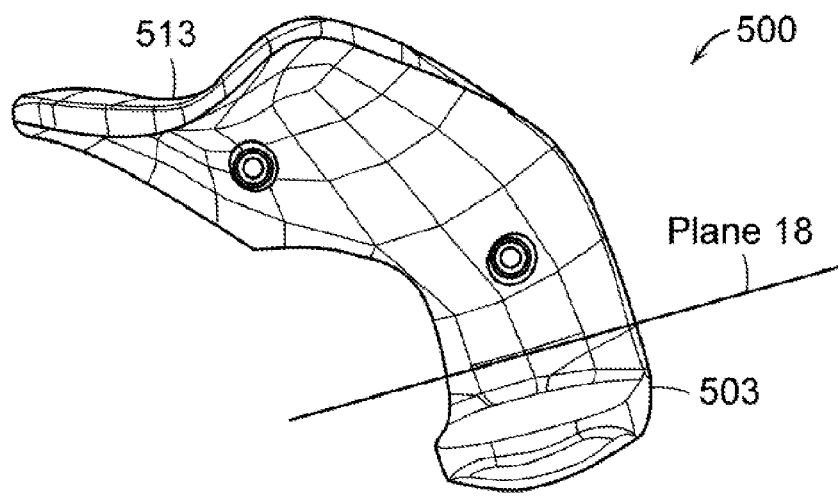

FIG. 2E is a view of the implant 500 showing a hatched three point loading support area which extends from a top portion 513 to a line (plane 17) and from a line (plane 18) to a bottom portion 515. Also illustrated are the pegs 530 extending from the superior surface. FIG. 2F illustrates the superior surface of the implant 500 with the pegs 530 extending from the superior surface. FIG. 2F also illustrates the hatched cantilever loading support area, which extends from the line (plane 18) to the top portion 513 of the implant. The loading forces and directions for each support condition are based on physiological load encounters. Table 1 shows the Physiological Loadings taken from a study by Seth Greenwald.

TABLE 1

Physiological Loadings[1]

| | Set-up | | |
|---|---|---|---|
| | "1" | "2" | "3" |
| Flexion Angle (degree) | 0° | 60° | 90° |
| Normal Force N (lbs.) | 2,900 (652) | 3,263 (733.5) | 3,625 (815) |
| Normal Force Case | Walking (4.0 × BW*) | Stair Descent (4.5 × BW*) | Stair Ascent (5.0 × BW*) |

*Body Weight (BW) taken as a 60 year old male, with 173 cm height for an average body weight of 74 kg (163 lbs).
[1]"Tibial Plateau Surface Stress in TKA: A Factor Influencing Polymer Failure Series III - Posterior Stabilized Designs;" Paul D. Postak, B.Sc., Christine S. Heim, B.Sc., A. Seth Greenwald, D. Phil.; Orthopaedic Research Laboratories, The Mt. Sinai Medical Center, Cleveland, Ohio. Presented at the 62nd Annual AAOS Meeting, 1995.

Using the implant 500, three point loading occurs from Set-up 1 (2900 N). To replicate a worst case loading scenario, a 75/25 load distribution (75% of 2900 N=2175 N) is used. The loading is concentrated on a 6 mm diameter circular area located directly below and normal to the peg on the bearing surface.

Turning to the cantilever loading shown in FIG. 2F, the loading occurs from Set-up 3, or 90 degrees, at a 75/25 load distribution (75% of 3625 N=2719 N). As with the above example, the loading is concentrated on a 6 mm diameter circular area located at the center of the posterior-most portion of the medial condyle normal to the flat cut surface of the posterior condyle.

Figure 2G:
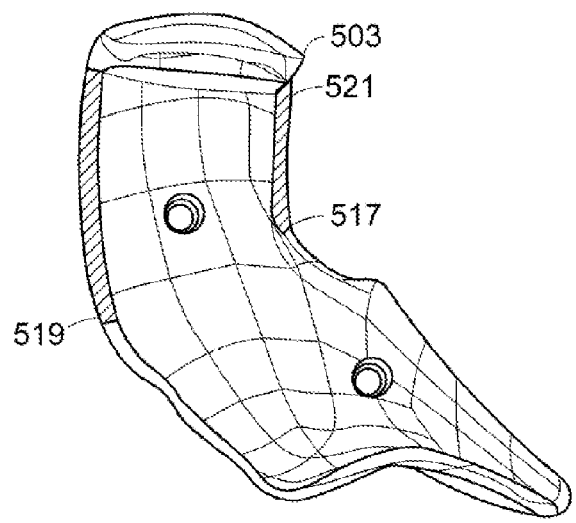
FIGS. 2G and H illustrate an alternative embodiment wherein the implant has lateral rails.
Figure 2H:
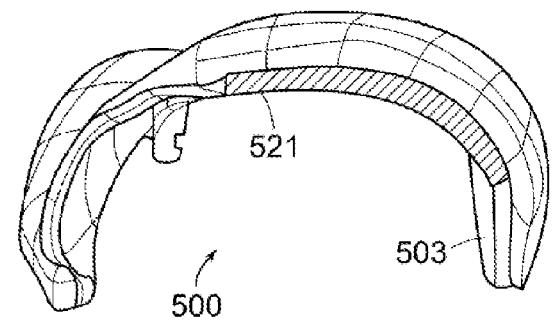

FIGS. 2G and H illustrate alternate embodiments of the implant 500 having a rail design that provides one or more rails 521 along medial and/or lateral sides of the implant 500. The rail 521 can be positioned so that it extends along a portion of the medial 517 and/or lateral 519 sides before communicating with the angled surface 503. One or more side rails 521 can be provided.

Figure 2I:
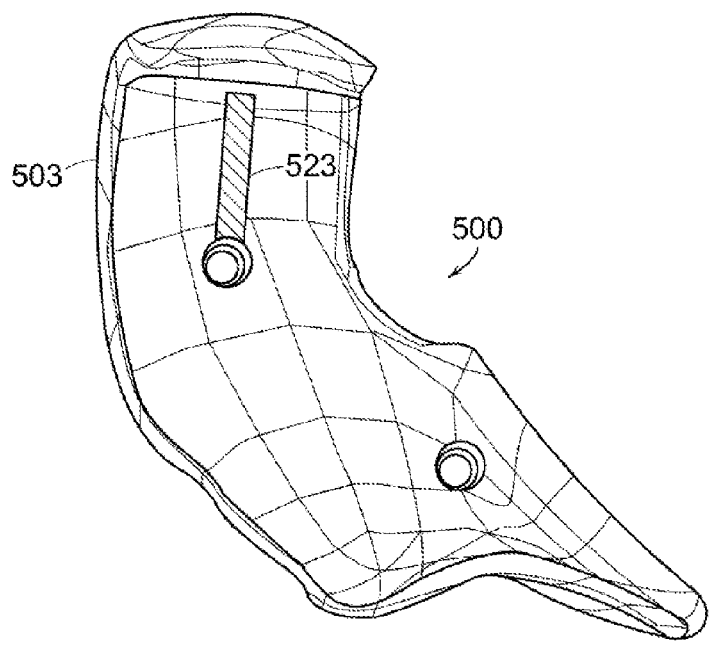
FIG. 2I illustrates another embodiment wherein the implant has an anchoring keel.

FIG. 2I illustrates another embodiment of an implant 500 having a keel design. A keel 523 (or centrally formed rail) is provided on the superior surface of the implant. In this embodiment, the keel 523 is located on the surface of the implant, but not at the sides. The keel can be centered, as shown, substantially centered, or located off-center.

Figure 2J:
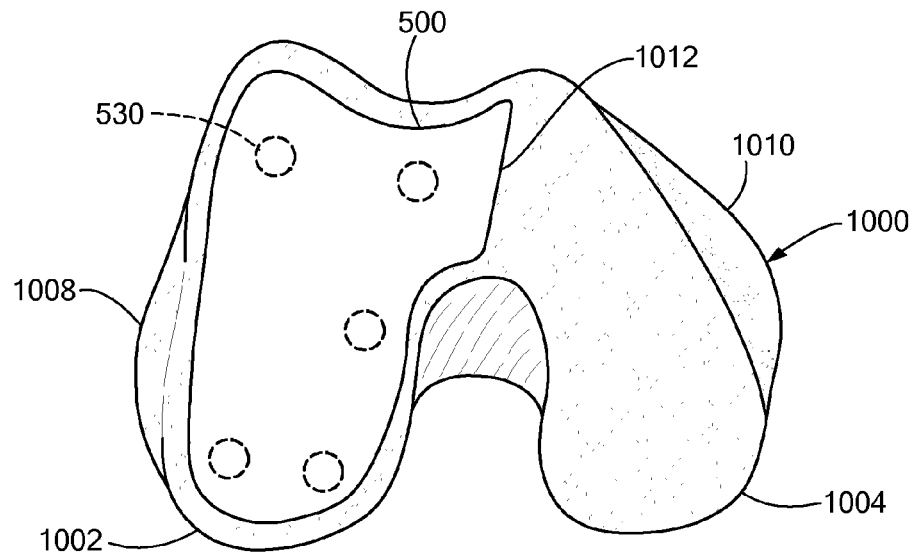
FIG. 2J is an axial view of a femur with the implant installed on the femoral condyles.

FIG. 2J illustrates the axial view of the femur 1000 having a lateral condyle 1002 and a medial condyle 1004. The intercondylar fossa is also shown 1006 along with the lateral epicondyle 1008 and the medial epicondyle 1010. The patellar surface of the femur 1012 is also illustrated. The implant 500, illustrated in FIG. 2A, is shown covering the lateral condyle and a portion of the patellar surface of the femur 1012. The pegs 530 also are shown that facilitate anchoring the implant 500 to the condyle and patellar surface.

Figure 2K:
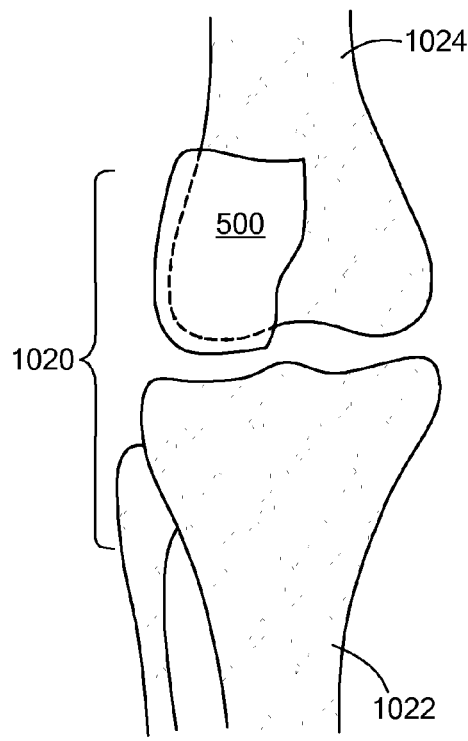
FIG. 2K is an anterior view of the knee joint without the patella wherein the implant is installed on the femoral condyle.
Figure 2L:
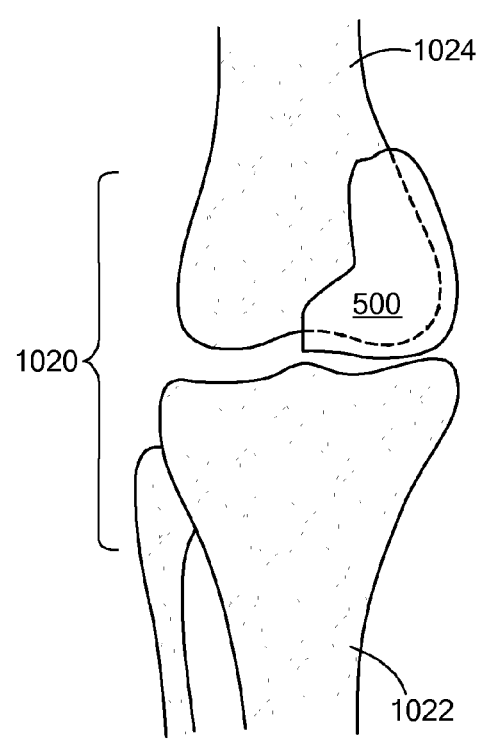
FIG. 2L is an anterior view of the knee joint with an implant of FIG. 2A implanted on the femoral condyles along with an implant suitable for the tibial plateau, such as that shown in FIG. 5.

FIG. 2K illustrates a knee joint 1020 from an anterior perspective. The implant 500 is implanted over the lateral condyle. FIG. 2L illustrates a knee joint 1020 with the implant 500 covering the medial condyle 1004. As illustrated in FIGS. 2K and L, the shape of the implant 500 corresponding to the patella surface can take on a variety of curvatures.

Figure 2M:
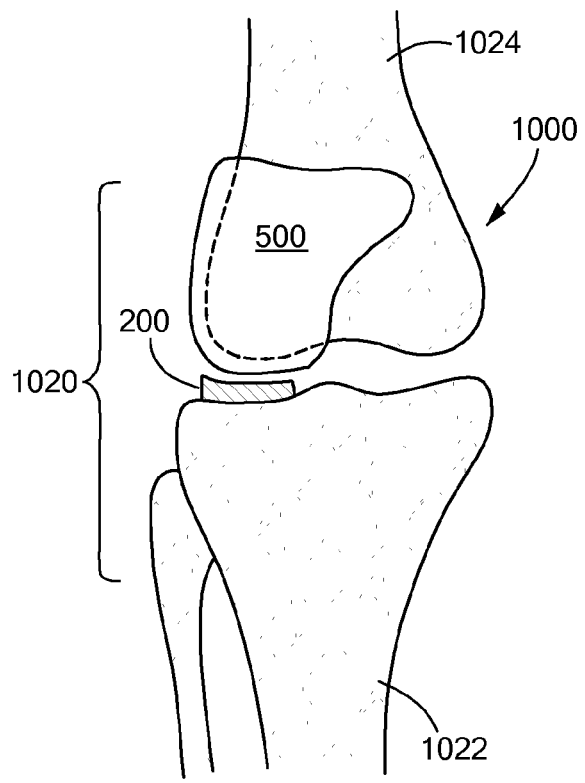
FIGS. 2M-N depict a device implanted within the knee joint.
Figure 2N:
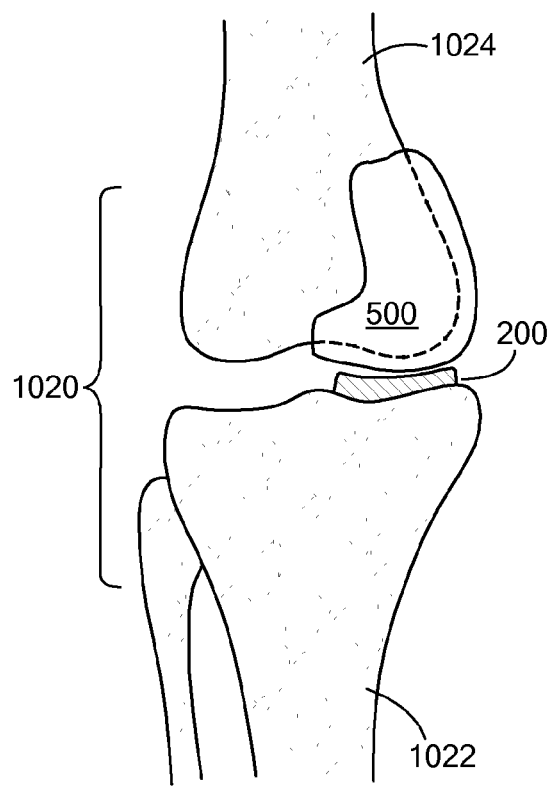

Turning to FIGS. 2M and 2N, the implant 500 is positioned such that it communicates with an implant 200 designed to correct a defect in the tibial plateau.

3.4.1 Cut Regions of Superior Surface

Figure 2O:
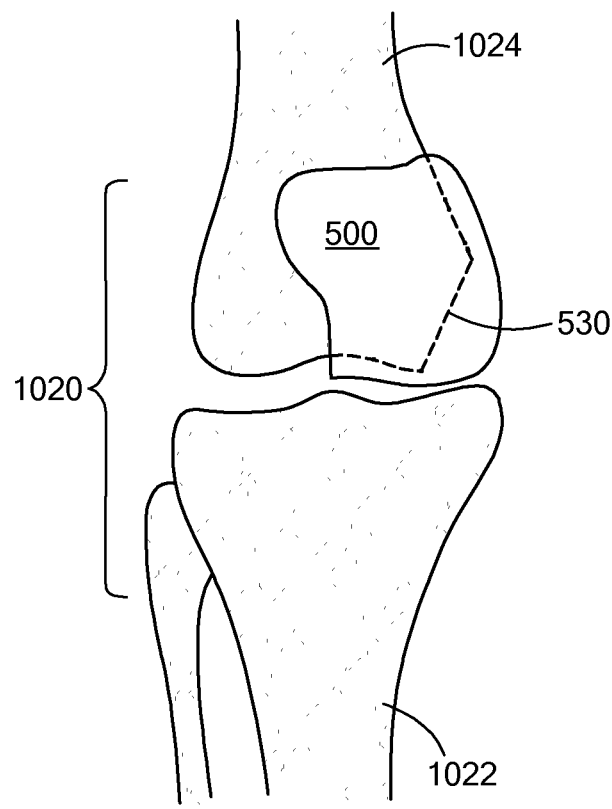
FIG. 2O depicts an alternate embodiment of the device which accommodates a partial removal of the condyle.
Figure 2P:
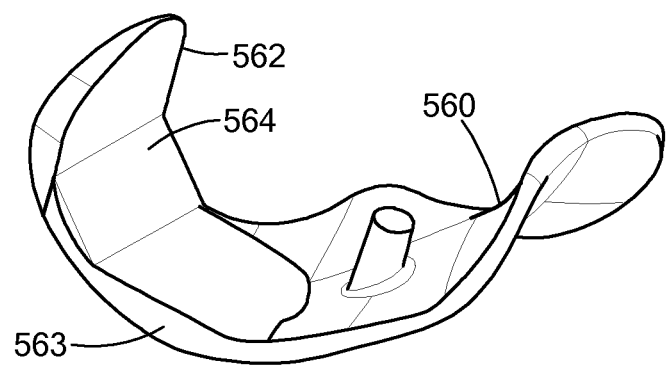

As shown in FIGS. 2A-2N, the implant 500 can include an angled surfaces (also referred to herein as a cut surface or cut region or bone cut or cut) 503 on the superior surface 502 (also referred to herein as the inner, bone-facing surface). The one or more angled surfaces 503 can be provided to communicate with a modified (e.g., resected) or worn surface of an anatomical structure, for example, cartilage and/or bone. The femoral bicompartmental implants or implant components 500 shown in FIGS. 2A-2N include a single, posterior bone cut. Embodiments that include a posterior bone cut also can include one or more contoured surface(s) for mating to one or more bone and/or cartilage surfaces, as well as one or more additional cuts, such as one or more posterior cuts, one or more anterior cuts, one or more distal cuts, one or more chamfer cuts, and/or one or more oblique cuts. An example of an oblique cut is shown in FIG. 2O. Specifically, as shown in FIG. 2O, the implant 500 can have a superior surface 502 which substantially conforms to the surface of the condyle but which has at least one flat portion corresponding to an oblique cut on the bone as shown in FIG. 2O. FIG. 2P illustrates an implant 500 having a contoured surface 560 for mating with the joint surface and a posterior cut 562, a distal cut 563, and a chamfer cut 564. In this embodiment, no anterior cut is provided.

In certain embodiments, the bicompartmental implant 500 includes an anterior cut. For example, the superior surface of an implant 500 can include one or more contoured surfaces for mating to one or more bone and/or cartilage surface(s) and a single, anterior cut for mating to a modified (e.g., resected) bone surface. Alternatively, the superior surface can include one or more contoured surfaces for mating to one or more bone and/or cartilage surfaces, an anterior cut for mating to a cut bone surface, and one or more additional cuts, such as one or more additional anterior cuts, one or more posterior cuts, one or more distal cuts, one or more chamfer cuts, and/or one or more oblique cuts for mating to one or more modified (e.g., resected) bone surfaces.

In certain embodiments, the superior surface of a bicompartmental implant 500 can consist primarily of cut surfaces (i.e., without any portion being an uncut, contoured surface). The cut surfaces can include one or more anterior cuts, one or more posterior cuts, one or more distal cuts, one or more chamfer cuts, and/or one or more oblique cuts.

Figure 2Q:
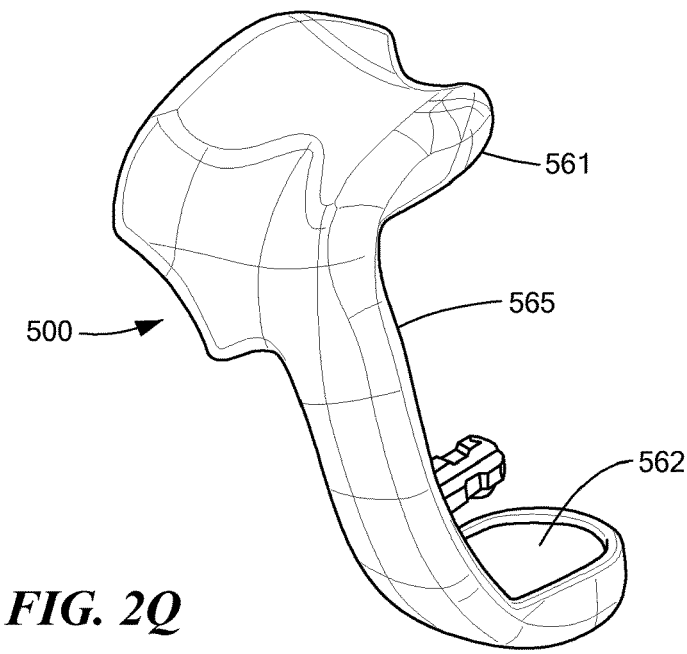
Figure 2R:
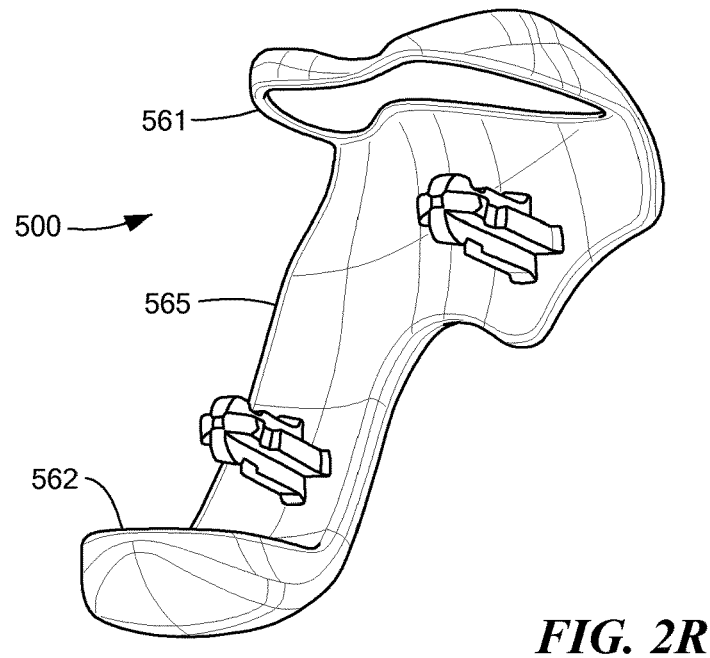

In preferred embodiments, the bicompartmental implant or implant component 500 includes an anterior cut and a posterior cut on the superior surface. Certain preferred embodiments also can include on the superior surface, between the anterior cut and posterior cut, one or more contoured surface(s) for mating to one or more bone and/or cartilage surfaces. FIGS. 2Q and 2R illustrate a preferred embodiment of a bicompartmental implant or implant component 500 having a contoured surface 565 for mating with an unmodified anatomical structure and an anterior cut 561 and a posterior cut 562 for mating with modified anatomical structures. FIG. 2R shows the same implant 500 as in FIG. 2Q, but from a different angle. One or more of the anterior cut, the posterior cut, and the contoured surface can be patient-specific, for example, designed using patient-specific data to be an anatomic or near-anatomic match to the patient's anatomic structure. Alternatively or additionally, one or more of the anterior cut, the posterior cut, and the contoured surface can be selected, for example, from a library.

In certain embodiments, the anterior cut and/or the posterior cut (and/or optionally any one or more other cuts) on the superior surface can be engineered. For example, one or more bone cuts can be designed to match one or more resected bone surfaces that themselves are designed or selected to meet a target or parameter, such as minimizing the amount of resected bone. To the extent that patient-specific data is used to engineer an optimized bone cut for the implant 500, the implant 500 and/or implant bone cut can be understood to be patient-engineered.

Figure 2S:
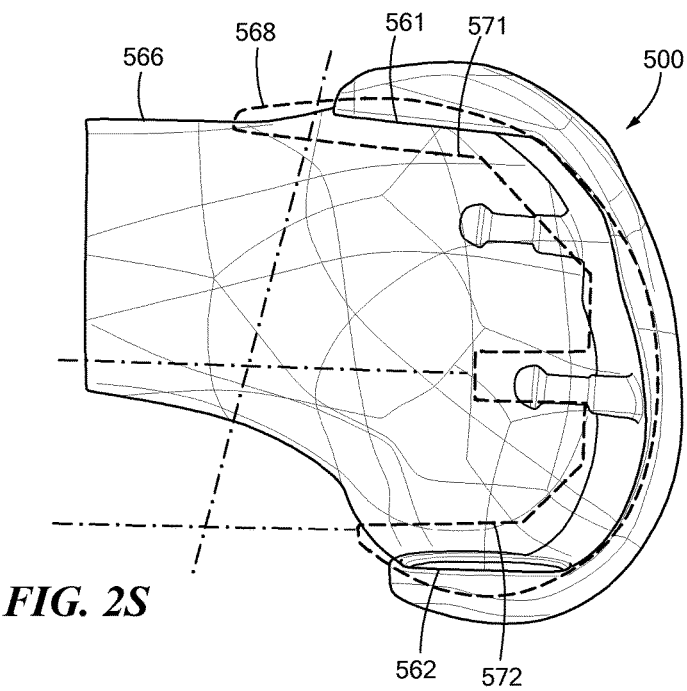

This engineering aspect can allow for one or more cuts to the patient's bone that resects less bone than is required for a traditional primary total knee arthroplasty ("TKA") implant. For example, one or more of the optimized bone cuts can allow less than 12 mm, less than 10 mm, less than 8 mm, less than 6 mm, and/or less than 4 mm of bone resected from the surface of the femur. For example, FIG. 2S illustrates the implant 500 of FIGS. 2Q and 2R engaging a model of a femur 566. The implant 500 is overlaid with an outline of a traditional primary TKA implant 568. As shown in the figure, the anterior cut 561 for implant 500 retains more bone than the anterior cut 571 for the traditional primary TKA implant 568. Similarly, the posterior cut 562 for implant 500 retains more bone than the posterior cut 572 for the traditional primary TKA implant 568. Accordingly, the design of implant or implant component 500 can allow for a subsequent surgery to the knee, if required at a later date, to be performed with a traditional primary implant rather than as a revision surgery.

Figure 3:
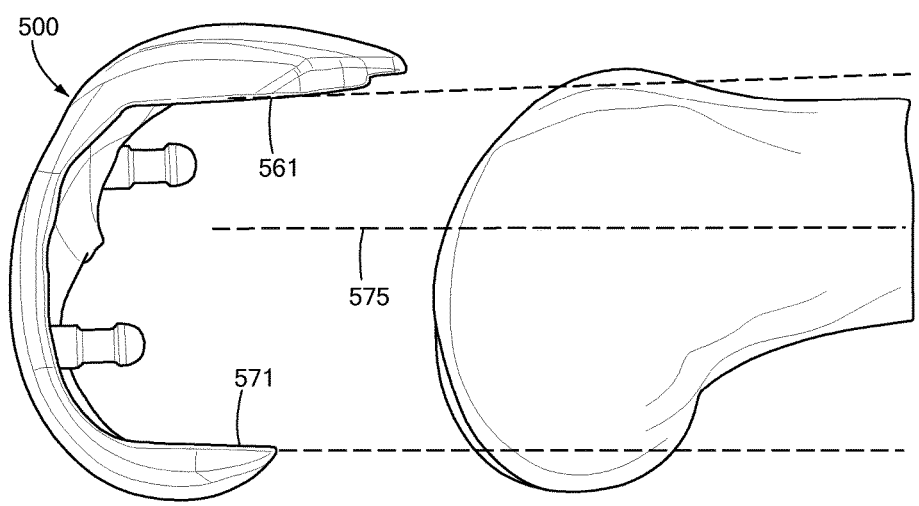
FIG. 3 illustrates a bicompartmental implant having an anterior cut and a posterior cut that are substantially parallel to the patient's femoral axis.

In certain embodiments, one or both of the anterior and posterior cuts on the superior surface of the bicompartmental implant or implant component 500 can be substantially parallel to the patient's femoral axis, including having one or both cuts slightly oblique to the femoral axis. FIG. 3 illustrates a bicompartmental implant or implant component 500 having an anterior cut 561 and a posterior cut 571 that are substantially parallel to the patient's femoral axis 575. In the figure, the anterior cut 561 is slightly oblique to the femoral axis.

In certain embodiments, one or both of the anterior and posterior cuts can be substantially non-parallel to the patient's femoral axis. For example, one or both of the anterior and posterior cuts can be substantially angled posteriorly or "flexed" one or more degrees in the direction of a knee in flexion. This can help reduce the amount of bone resected on the anterior flange and can line up resection planes close to a typical primary TKA, which can aid in applying a primary TKA implant as a replacement, should a replacement be necessary.

Figures 4A, 4B:
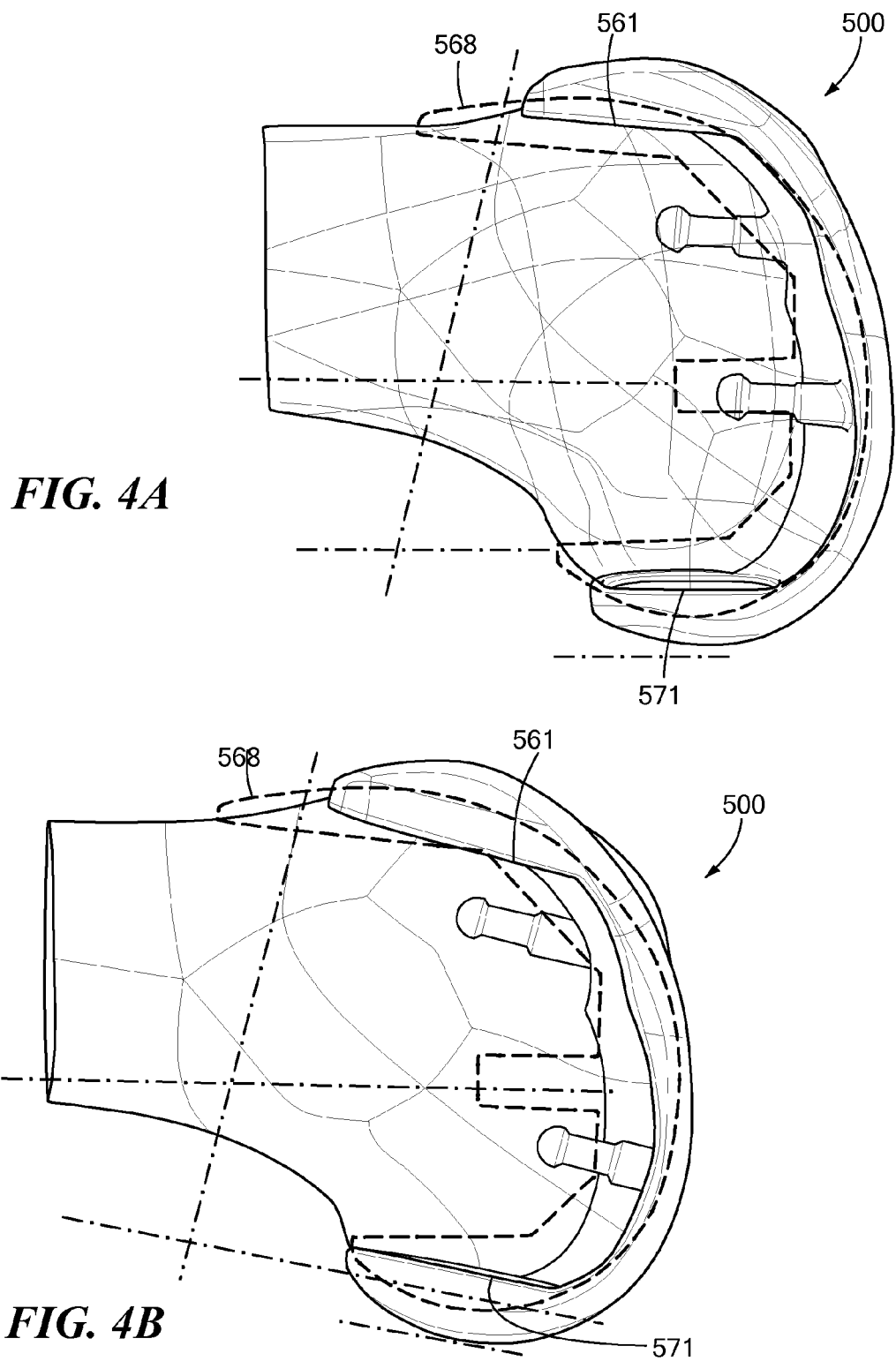
FIGS. 4A and 4B illustrate bicompartmental implants overlaid with a traditional primary TKA implant.

For example, one or both of the anterior and posterior cuts can be rotated or flexed posteriorly (e.g., in flexion) by 5 degrees, 5 or more degrees, 7 degrees, 7 or more degrees, 7-8 degrees, 7.5 degrees, 7.5 or more degrees, 8 degrees, 8 or more degrees, 10 degrees, 10 or more degrees, 12.5 degrees, 12.5 or more degrees, 15 degrees, and/or 15 or more degrees. FIGS. 4A and 4B illustrate bicompartmental implants or implant components 500 overlaid with a traditional primary TKA implant 568. In FIG. 4A, the implant or implant component 500 includes a cut profile and pegs flexed 7.5 degrees from the femoral mechanical axis, with an anterior cut 561 cut that is 1 degree divergent from the profile and a posterior cut 571 that is 6 degrees divergent from the profile. In FIG. 4B, the implant or implant component 500 includes a cut profile and pegs flexed 15 degrees from the mechanical axis, with an anterior cut 561 cut that is 2 degrees divergent from the profile and a posterior cut 571 that is 5 degrees divergent from the profile.

As shown in FIG. 4B, an implant or implant component 500 including anterior and posterior cuts 561, 571 in planes flexed 7.5 degrees minimizes the bone resected for the anterior cut and lines up resection planes close to a traditional TKA implant. Accordingly, in certain embodiments, the bicompartmental implant or implant component 500 allows for a subsequent revision using a traditional TKA implant.

As with cuts that are substantially parallel to the patient's femoral axis, cuts that are substantially non-parallel to the patient's femoral axis, for example, cuts that lie in a particular flexed plane, can include cuts that are slightly oblique to the particular flexed plane.

Figure 5:
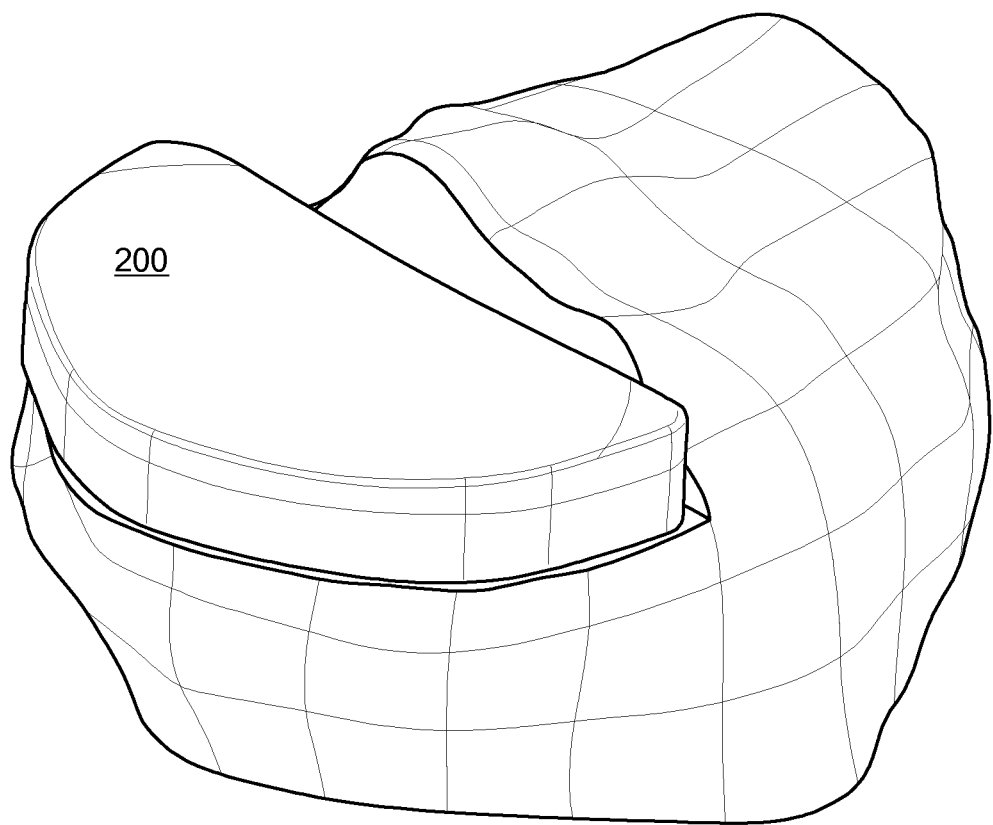
FIG. 5 shows a tibial implant for mating with the condylar portion of the bicompartmental implant, implanted on the tibia.

One or more features of a tibial implant component can be preoperatively engineered based on patient-specific data to provide to the patient an optimized fit with respect to one or more parameters. For example, an engineered bone preserving tibial implant component can be designed and/or selected based on one or more of the patient's joint dimensions as seen, for example, on a series of two-dimensional images or a three-dimensional representation generated, for example, from a CT scan or MRI scan. FIG. 5 shows a tibial implant 200 for mating with the condylar portion of the bicompartmental implant, implanted on a model of a tibia.

3.4.2 Contoured Portion of Superior Surface

As discussed above, a femoral bicompartmental implant or implant component 500 can include on its superior surface one or more contoured surface areas for mating to one or more of the patient's bone or cartilage surfaces. In certain embodiment, the topography of one or more of these contoured surfaces can substantially negatively match (e.g., be a negative complement to) the patient's bone and/or cartilage surface. For example, in certain embodiments, the topography of one or more of the contoured surfaces is designed using patient-specific data to substantially match one or more of the patient's bone or cartilage surfaces.

3.1.3 Anterior Flange

Figure 6A:
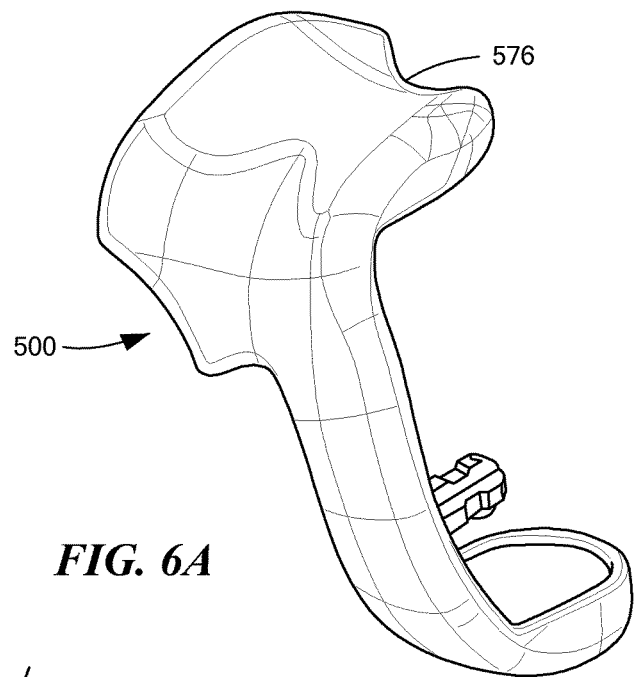
FIG. 6A illustrates an exemplary anterior flange of a bicompartmental implant or implant component.

FIG. 6A illustrates an exemplary anterior flange 576 of a bicompartmental implant or implant component 500. In certain embodiments, the bicompartmental implant or implant component 500 includes an anterior flange that allows for substantial coverage of the patella-femoral ("PF") region, which includes the region of the distal femur that contacts the patella during flexion and extension. A short anterior flange, for example, one that does not cover a substantial portion of the PF contact area, can cause the patella to catch or clunk against the proximal edge of the implant as the patella moves across the PF region during the extension-flexion motion.

In certain embodiments, the bicompartmental implant or implant component 500 includes a flange edge that is patient-specific. For example, in certain embodiments, one or more anterior flange edges, such as the proximal edge, the lateral edge, and/or the medial edge, can be designed using patient-specific data to be an anatomic or near-anatomic match to the patient's anatomic structure. In certain embodiments, the one or more anterior flange edges can be designed from patient-specific data to supply an anterior flange having more than a specified minimum coverage of the patient's PF region. For example, certain embodiments include an anterior flange that supplies 30%, greater than 30%, 40%, greater than 40%, 50%, greater than 50%, 60%, greater than 60%, 70%, greater than 70%, 80%, greater than 80%, 90%, greater than 90%, 95%, greater than 95%, and/or 100% coverage to the PF region contact area at full extension. In certain embodiments, the patient-specific flange coverage substantially matches and covers the resected bone surface, thereby reducing blood loss from resected bone. In addition, one or more patient-specific flange edges can help to minimize gaps or overhang between the flange edge and the patient's anatomic structure. Such gaps, sometimes referred to as air-balls, typically are filled with cement during the surgical implantation of a traditional implant. However, loose cement can be a primary cause of premature implant wear.

In certain embodiments, the bicompartmental implant or implant component 500 includes an anterior flange edge that is engineered. For example, one or more aspects or features of the anterior flange, such as length, width, thickness, or edge design, can be designed to match a resected bone surface that itself is designed or selected to meet a target or parameter. To the extent that patient-specific data is used to engineer an optimized feature or aspect of the anterior flange, the implant 500, anterior flange, and/or engineered aspect or feature of the flange can be understood to be patient-engineered.

Figure 6B:
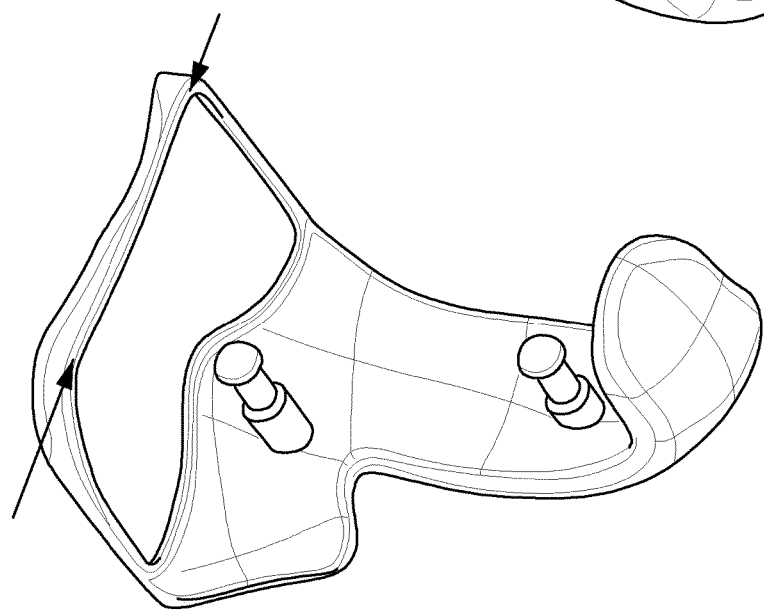
FIG. 6B illustrates a bicompartmental implant that includes a substantially straight proximal flange edge.

In certain embodiments, the bicompartmental implant or implant component 500 includes an anterior flange edge that is standard. For example, as illustrated in FIG. 6B, the bicompartmental implant or implant component 500 can include a substantially straight proximal flange edge.

3.4.4 Thickness and Width

The bicompartmental implant or implant component 500 can include varying thicknesses and/or widths across the entire implant or portions of the implant. In certain embodiments, the bicompartmental implant or implant component 500 includes one or more thicknesses and/or widths that are patient-specific. For example, the implant thickness, entirely or in part, can be designed using patient-specific data to match the corresponding thickness of the patient's anatomical structure that the implant replaces. Similarly, the implant width, entirely or in part, can be designed using patient-specific data to match the corresponding width of the patient's anatomical structure.

In certain embodiments, the bicompartmental implant or implant component 500 includes one or more thicknesses and/or widths that are engineered. For example, the implant thickness, entirely or in part, and/or the implant width, entirely or in part, can be engineered to include an optimized thickness or width. To the extent that patient-specific data is used to engineer an optimized width and/or thickness, the implant 500, engineered width, and/or engineered thickness can be understood to be patient-engineered.

In certain embodiments, the bicompartmental implant or implant component 500 includes a PF region having a reduced thickness relative to a traditional implant thickness. For example, relative to a traditional implant thickness of 3-4 mm, the bicompartmental implant or implant component 500 can include a PF region thickness that is reduced by 1 mm, greater than 1 mm, 2 mm, greater than 2 mm, 3 mm, and/or greater than 3 mm. In certain embodiments, an engineered minimum thickness can be used to prevent overstuffing of the PF joint and reduce the risks of limited flexion/extension patella catching and subluxation that are typically observed with traditional bicompartmental implants. For example, in certain embodiments, the thickness between the anterior cut on the superior surface and the PF region on the inferior surface of the bicompartmental implant or implant component 500 can be engineered to include a minimum thickness of 3 mm, 3 mm or less, 2.5 mm, 2.5 mm or less, 2.0 mm, 2.0 mm or less, 1.5 mm, 1.5 mm or less, 1.0 mm, and/or 1 mm or less.

In certain embodiments, the thickness and/or width of an implant 500 can fall within standardized parameters. For example, the implant 500 can include thicknesses between 2.0 mm and 4.0 mm. In certain embodiments, the width of the implant can be designed to be 1-2 mm shorter than the width of the coronal surfaces of the patient's distal femur.

3.4.5 PF Region of Inferior Surface

Figure 7A:
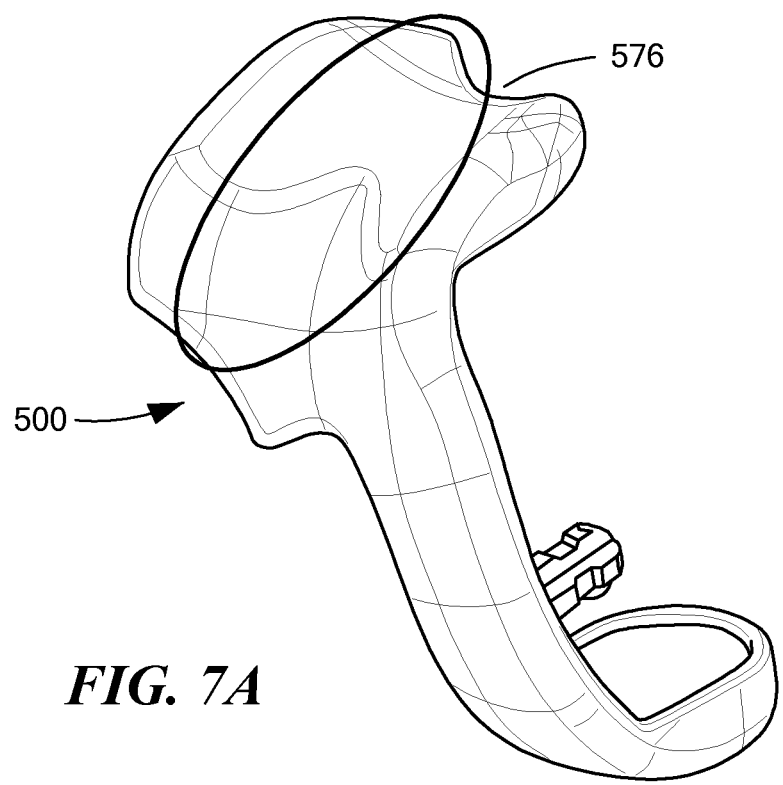
FIG. 7A illustrates an exemplary PF region of a bicompartmental implant.
Figure 7B:
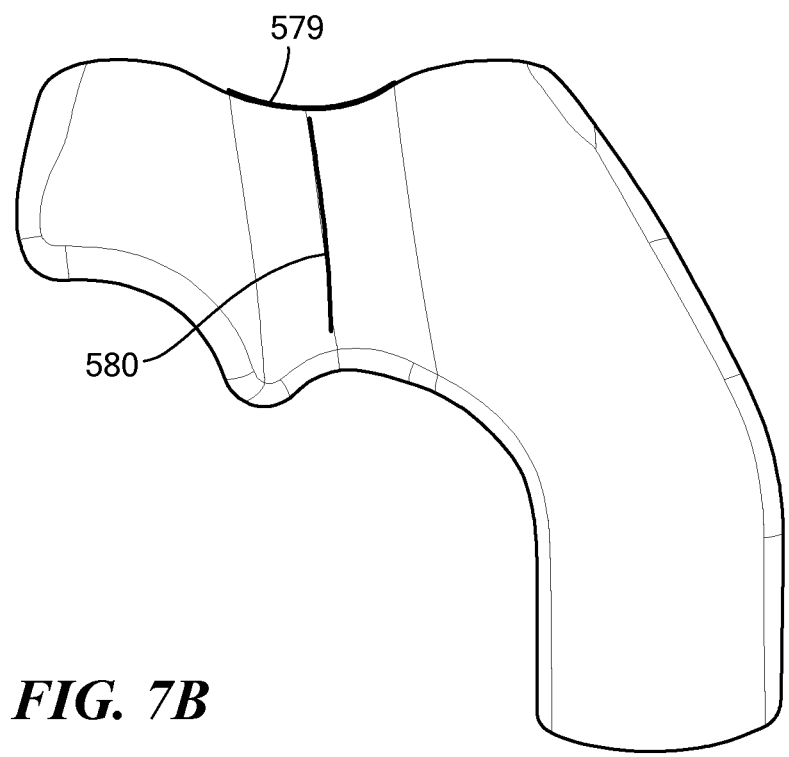
FIG. 7B illustrates an exemplary implant PF region having a trochlear groove with a coronal curvature and a sagittal curvature.
Figure 7C:
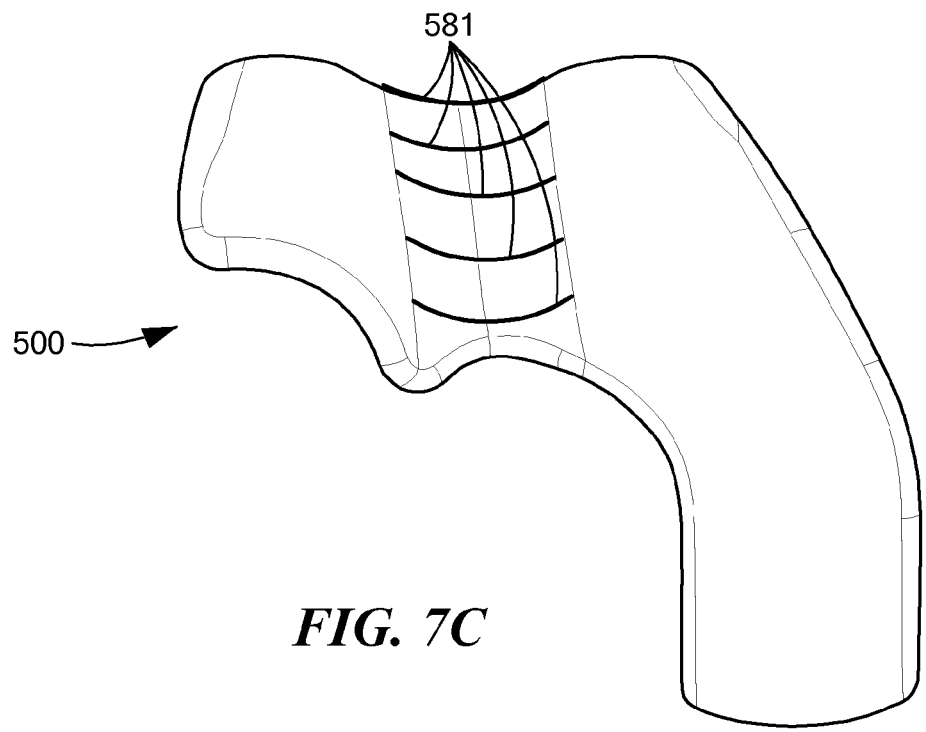
FIGS. 7C-7D illustrate coronal curvature radii (i.e., radii of curvature and/or tangent radii of curvature) and sagittal curvature radii in the PF region of an implant.
Figure 7D:
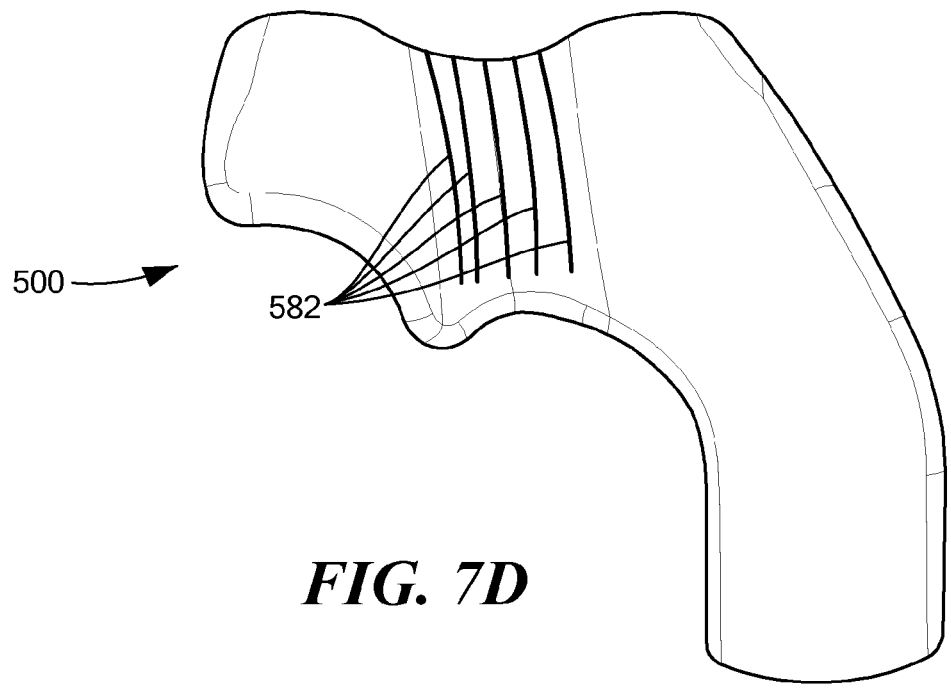

FIG. 7A illustrates an exemplary PF region 578 of a bicompartmental implant or implant component 500. As exemplified in FIG. 7B, the PF region includes a trochlear groove having a coronal curvature 579 and a sagittal curvature 580. In certain embodiments, the bicompartmental implant or implant component 500 includes a PF region having one or more curvatures that are patient-specific, entirely or in part. For example, with reference to FIGS. 7C and 7D, one or more coronal curvature radii 581 and/or one or more sagittal curvature radii 582 can be designed using patient-specific data to match the corresponding radii of the patient's PF region.

Figure 7F:
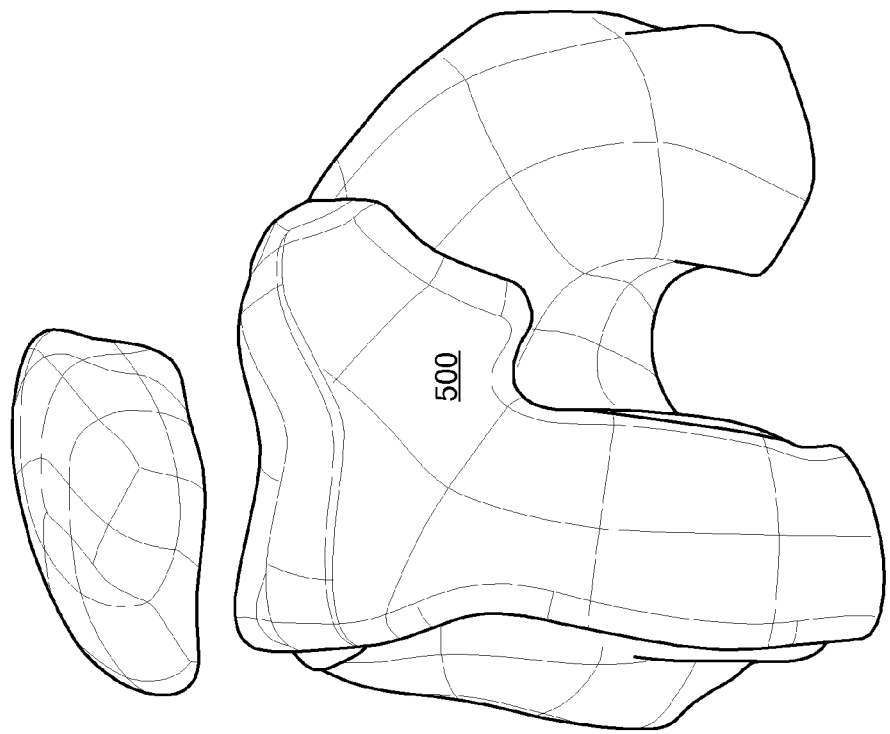
FIG. 7F illustrates a bicompartmental implant that includes a PF region having a coronal curvature that is engineered and a sagittal curvature that is patient-specific.
Figure 7E:
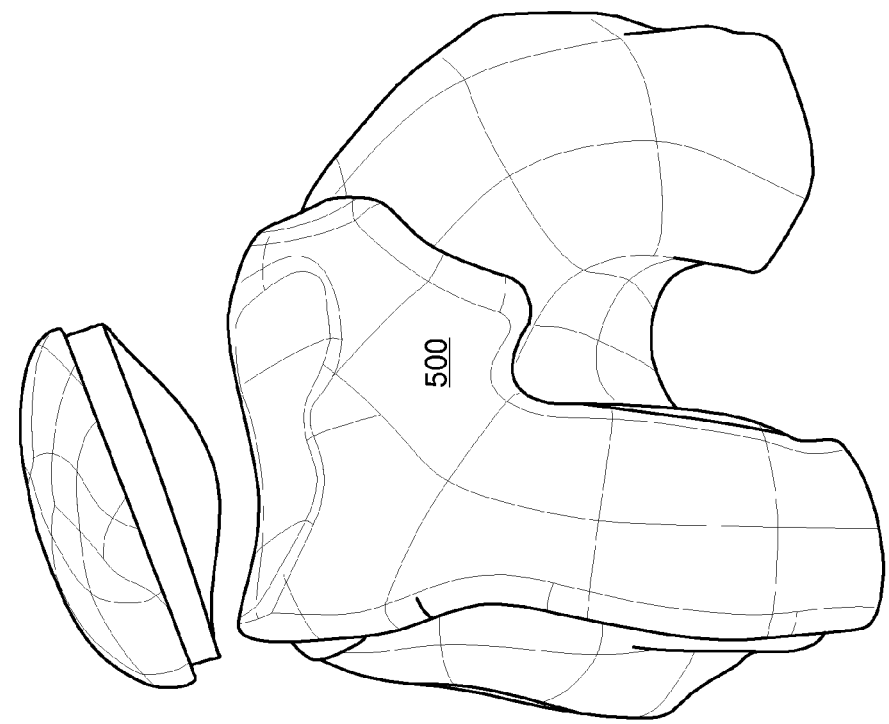
FIG. 7E illustrates a bicompartmental implant component that includes a PF region having a coronal curvature and a sagittal curvature that are engineered to optimize movement of a patella implant component.

In certain embodiments, the bicompartmental implant or implant component 500 includes a PF region having one or more curvatures that are standard or engineered, entirely or in part. For example, again with reference to FIGS. 7C and 7D, one or more coronal curvature radii 581 and/or one or more sagittal curvature radii 582 can be standard or engineered. For example, one or more radii can be engineered to optimize movement of the patella in the trochlear groove. A coronal curvature can include constant and/or varying radii. Similarly, a sagittal curvature can include constant and/or varying radii. In certain embodiments, one or both of the coronal curvature 579 and sagittal curvature 580 are engineered to optimize movement in the trochlear groove of a corresponding patellar implant component. FIG. 7E illustrates a bicompartmental implant component 500 that includes a PF region having a coronal curvature and a sagittal curvature that are engineered to optimize movement of a patella implant component.

The engineered and optimized curvatures can be derived from computer modeling and software automation, which can include steps to smooth or normalize patient-specific data. To the extent that patient-specific data is used to engineer an optimized coronal curvature and/or sagittal curvature of the trochlear groove in the implant 500, the implant and/or corresponding engineered curvature can be understood to be patient-engineered.

In certain preferred embodiments, the bicompartmental implant or implant component 500 includes a PF region having a coronal curvature that is engineered, at least in part, and a sagittal curvature that is patient-specific, at least in part. FIG. 7F illustrates a bicompartmental implant or implant component 500 that includes a PF region having a coronal curvature that is engineered and a sagittal curvature that is patient-specific. For example, the coronal curvature can be selected by choosing from a family of standard curvatures the one standard curvature that is most similar to the radii of the patient's corresponding coronal curvature. Alternatively, the coronal curvature can be selected by choosing from a family of standard curvatures a standard curvature with larger radii in order to achieve a less constraining biomechanical situation, or with smaller radii in order to achieve a more constraining biomechanical situation with the patella during knee motion.

In certain embodiments, the implant or implant component includes a trochlear groove coronal curvature having radii with lengths that are 20-25 mm, and/or 21-23 mm, and/or 22 mm. In certain embodiments, the implant or implant component includes a trochlear groove coronal curvature having radii with lengths that are 30-35 mm, and/or 31-33 mm, and/or 32 mm.

In certain embodiments, the bicompartmental implant or implant component 500 includes a PF region that is rotated externally, for example, the anterior resection and corresponding anterior portion of the implant 500 can be rotated externally by about 2 degrees, 2-3 degrees, 3 degrees, 3-4 degrees, 4 degrees, and/or by more than 4 degrees. This allows for a PF region with a relatively lower lateral condylar crest and trochlear groove and can provide additional relief from over-stuffing on the lateral side and reduction in the risk of subluxation and clunking. In certain embodiments, the bicompartmental implant or implant component 500 includes a PF region having a trochlear groove that is positioned laterally relative to the patient's trochlear groove, for example, by more than 1 mm, by 1-3 mm, and/or by 2 mm. In certain embodiments, the bicompartmental implant or implant component 500 includes a PF profile that is engineered to conform to the shape of a corresponding patella implant component.

The optimized PF profiles described above can: (1) allow for anatomy correction of defects while still maintaining useful patient-specific qualities such as trajectory and positioning; (2) lower stress on implant due to better conformity and the ability to balance out anatomy (such as high lateral ridge); (3) allow for smoother transition from relieved PF area to 3-4 mm main load bearing implant thickness; and/or (4) help maintain proper minimum (e.g., 3.0 mm) implant thickness of a relieved implant required to ensure proper implant strength.

3.4.6 Condylar Region of Inferior Surface

Figure 8A:
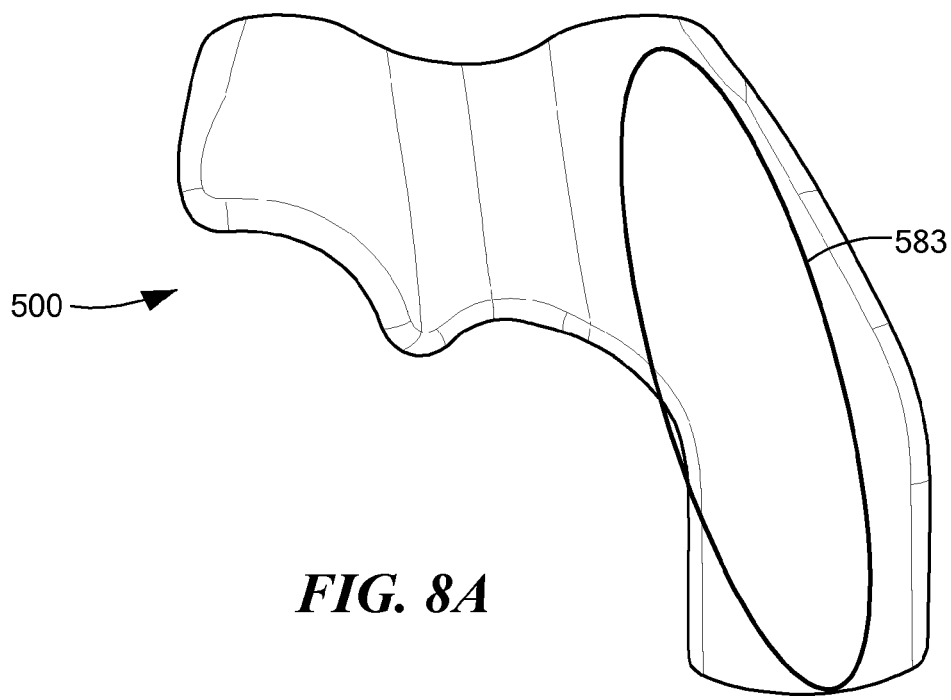
FIG. 8A illustrates the condylar portion or surface of a bicompartmental implant.
Figure 8B:
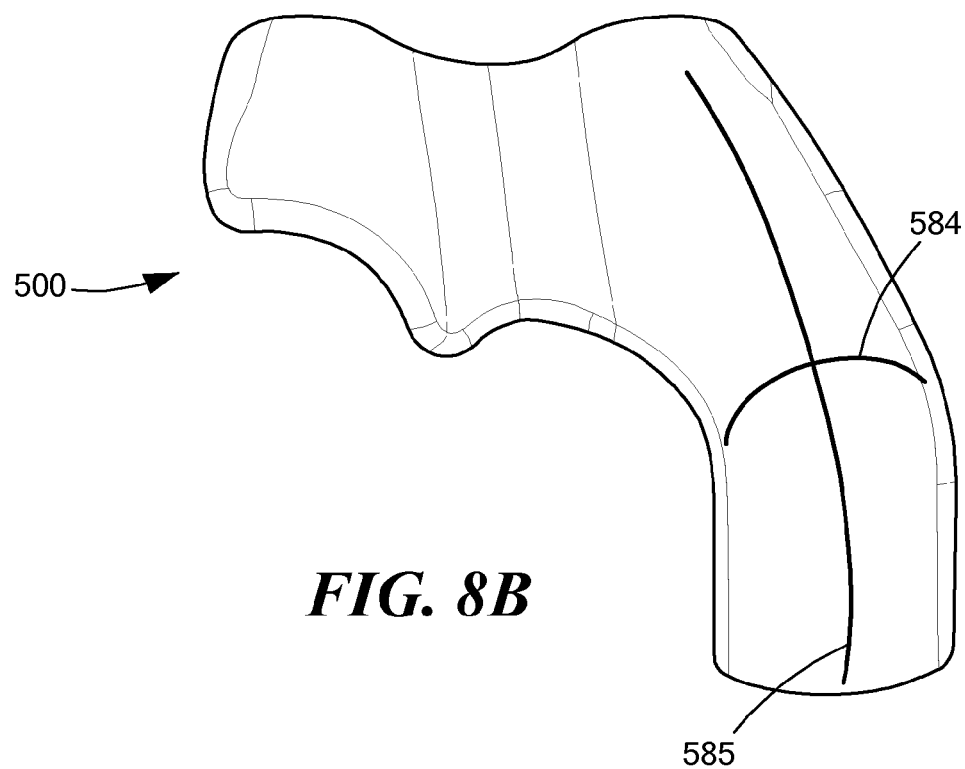
FIG. 8B illustrates a coronal curvature and a sagittal curvature of a condylar surface of an implant.

As shown in FIG. 8A, the bicompartmental implant or implant component 500 includes a condylar portion or surface 583. The condyle surface is the primary load bearing surface of an implant or implant component. Accordingly, the design of this surface, and the design for how it engages the opposing tibial surface, can affect implant wear and kinematics, particularly the proper motion of the implant at the joint. As with the PF region trochlear groove described above, and as shown in FIG. 8B, the condylar surface of an implant or implant component 500 includes a coronal curvature 584 and a sagittal curvature 585.

Figure 8C:
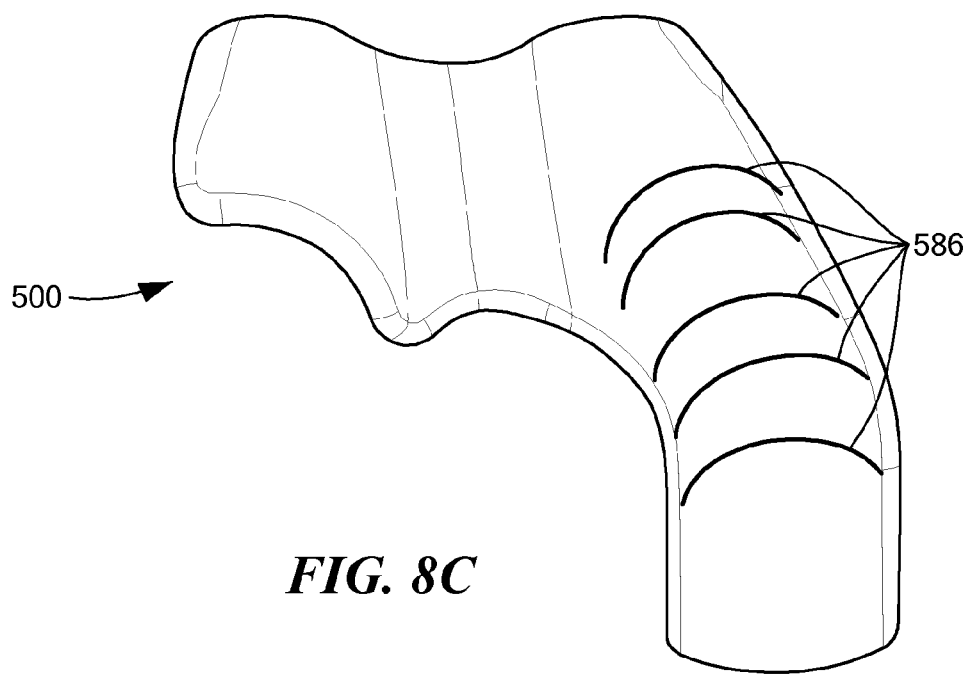
FIGS. 8C and 8D illustrate coronal curvature radii and sagittal curvature radii in the condylar region of an implant.
Figure 8D:
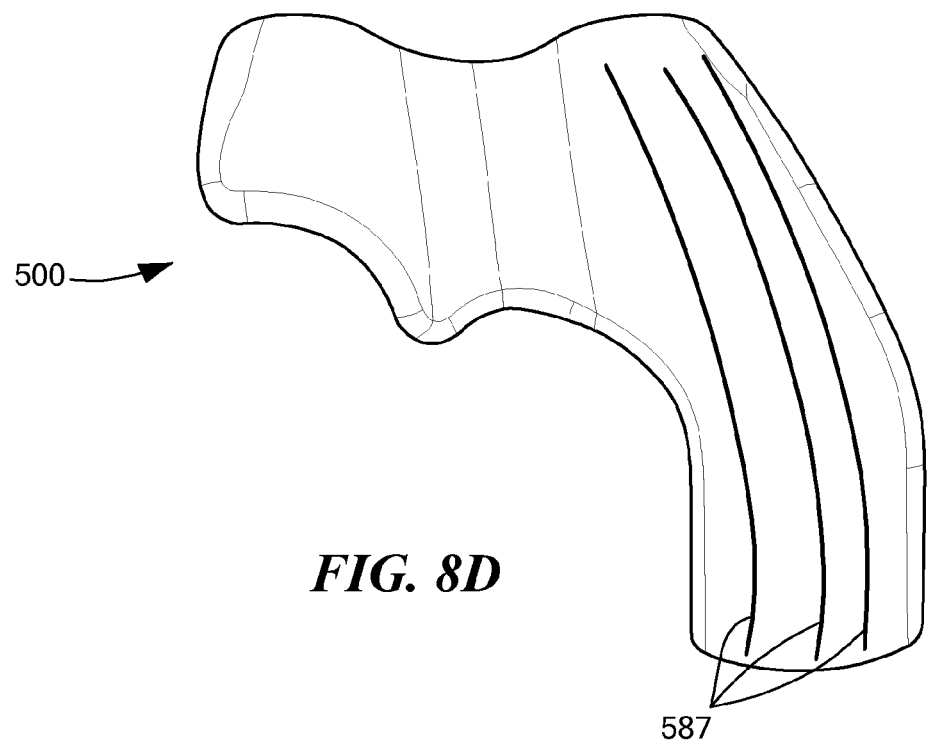

In certain embodiments, the bicompartmental implant or implant component 500 includes a condylar surface having one or more curvatures that are patient-specific, entirely or in part. For example, with reference to FIGS. 8C and 8D, one or more coronal curvature radii 586 and/or one or more sagittal curvature radii 587 can be designed using patient-specific data to match the corresponding radii of the patient's condylar curvatures.

In certain embodiments, the bicompartmental implant or implant component 500 includes a condylar surface having one or more curvatures that are standard or engineered, entirely or in part. For example, again with reference to FIGS. 8C and 8D, one or more coronal curvature radii 586 and/or one or more sagittal curvature radii 587 can be standard or engineered. For example, condylar coronal curvature radii and/or sagittal radii at the anterior portion of the implant or implant component can be optimized, for example, by lowering the radii lengths to allow for less restrained movement of the patella in the trochlear groove. Similarly, condylar coronal curvature radii and/or sagittal radii at the distal and/or posterior portions of the implant or implant component can be similarly optimized to allow a greater surface area of the condyle to move against the tibial surface. A coronal curvature can include constant and/or varying radii. Similarly, a sagittal curvature can include constant and/or varying radii. In certain embodiments, one or both of the coronal curvature 584 and sagittal curvature 585 are engineered to optimize movement with a corresponding patellar implant component or with a corresponding tibial implant component.

The engineered and optimized curvatures can be derived from computer modeling and software automation, which can include steps to smooth or normalize patient-specific data. To the extent that patient-specific data is used to engineer an optimized condylar coronal curvature and/or condylar sagittal curvature for the implant 500, the implant and/or corresponding engineered curvature can be understood to be patient-engineered.

In preferred embodiments, the bicompartmental implant or implant component 500 is designed to include a condylar, bearing surface having a sagittal curvature with, at least in part, patient-specific radii and a coronal curvature with a standard curvature. For example, the coronal curvature can be selected by choosing from a family of standard curvatures the one standard curvature that is most similar to the external radii of the patient's corresponding femoral condyle. Alternatively, the coronal curvature can be selected by choosing from a family of standard curvatures a standard curvature with larger radii in order to achieve a less constraining biomechanical situation, or with smaller radii in order to achieve a more constraining biomechanical situation during knee motion.

The coronal radius of a typical human femoral condyle can range from 20 to 30 mm. In certain embodiments, the coronal radius of the condyle on a bicompartmental implant or implant component 500 can be greater than 20 mm, greater than 30 mm, between 20 and 40 mm, or between 30 and 40 mm.

In certain embodiments, the bicompartmental implant or implant component 500 design also can include a small cut (also referred to as a dive in) on the anterior portion of the condyle that is not covered by the implant. This can aid in sinking the edge of the implant or implant component into this bone cut and can allow for a smooth surface transition from cartilage to implant, for example, for patellar movement across the surface.

3.4.7 Pegs

Figure 9A:
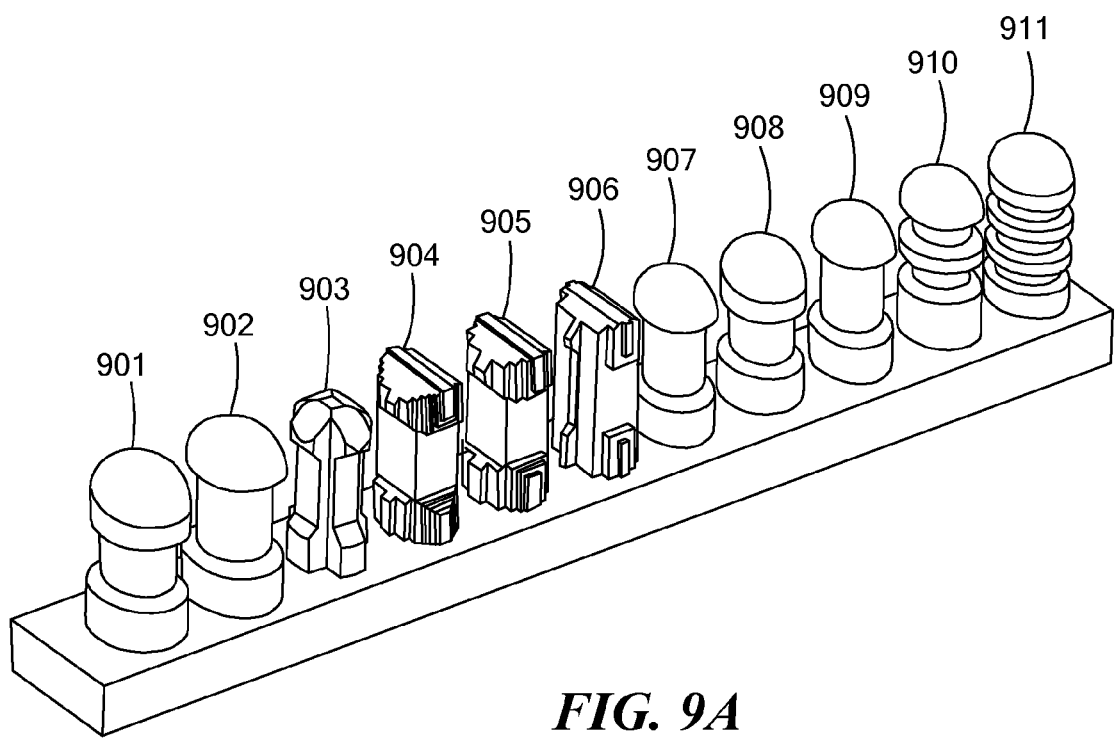
FIG. 9A illustrates a variety of peg configurations that can be used as part of an implant.
Figure 9B:
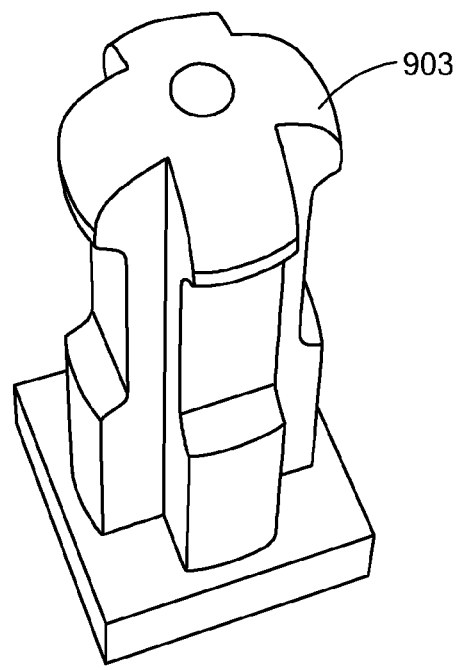
FIG. 9B illustrates an implant peg having a "+" or cross-like configuration.

A variety of peg configurations can be used for a bicompartmental implant or implant component 500. Exemplary configurations are illustrated as 901-911 of FIG. 9A. In certain embodiments, the peg cross-section can be round, as in 901, 902, 907, 908, 909, 910 and 911. In certain embodiments the peg cross-section can include a "+" or cross-like configuration, as shown in FIG. 9B, which is a close-up of 903 of FIG. 9A, which may aid in manufacturing. For example, in layering processes (used to create a casting blank), such as stereolithography (SLA), selective laser sintering (SLS), or fused deposition modeling (FDM), generating the curved edges of a blank typically is more difficult than that of casting the straight-edges of a blank. Accordingly, the straight-edges of the "+" configured peg may allow for a simpler and better defined blank used in the casting process as compared to a round peg.

A variety of peg sizes can be used for a bicompartmental implant or implant component 500. For example, a 7 mm peg, such as a "+" configured peg, can be used. The peg can be oriented on the device at any angle. For example, one or more pegs can be oriented in line with the femoral mechanical axis. Alternatively, one or more pegs can be oriented at an anterior-leaning angle as the peg extends from the implant, as shown in FIG. 4A. For example, one or more pegs can be oriented anteriorly 5 degrees, 5-10 degrees, 10 degrees, 10-15 degrees, and/or 15 degrees in an anterior-leaning angle relative to the femoral mechanism axis. The pegs can be oriented at the same angle or at different angles as one or both of the anterior and posterior cuts of the implant or implant device 500.

3.4.8 Deriving a Patient-Specific Shape

Figure 10A:
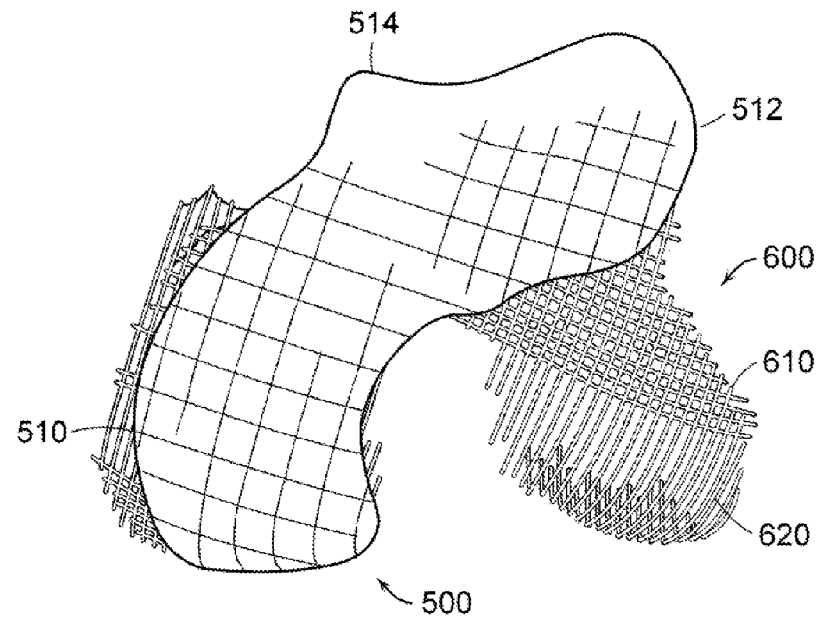
FIGS. 10A-G illustrate a device as shown in FIG. 2 along with a graphical representation of the cross-sectional data points comprising the surface map.

FIGS. 10A-10G illustrate the implant 500 of FIG. 2 with a graphical representation of the cross-sections 610, 620 from which a surface shape of the implant is derived. FIG. 10A illustrates a top view of the implant 500 sitting on top of the extracted surface shape 600. This view of the implant 500 illustrates a notch 514 associated with the bridge section of the implant 512 which covers the patellar surface of the femur (or the trochlea region) to provide a mating surface that approximates the cartilage surface. As will be appreciated by those of skill in the art, the shape of an implant designed for the medial condyle may not necessarily be the same or a mirror-image of the implant designed for the lateral condyle because of differences in anatomy. Thus, for example, the notch 514 may not be present in an implant designed for the medial condyle and the patellar surface of the femur. Therefore, the implant can be designed to include all or part of the trochlea region or to exclude it entirely.

Figure 10B:
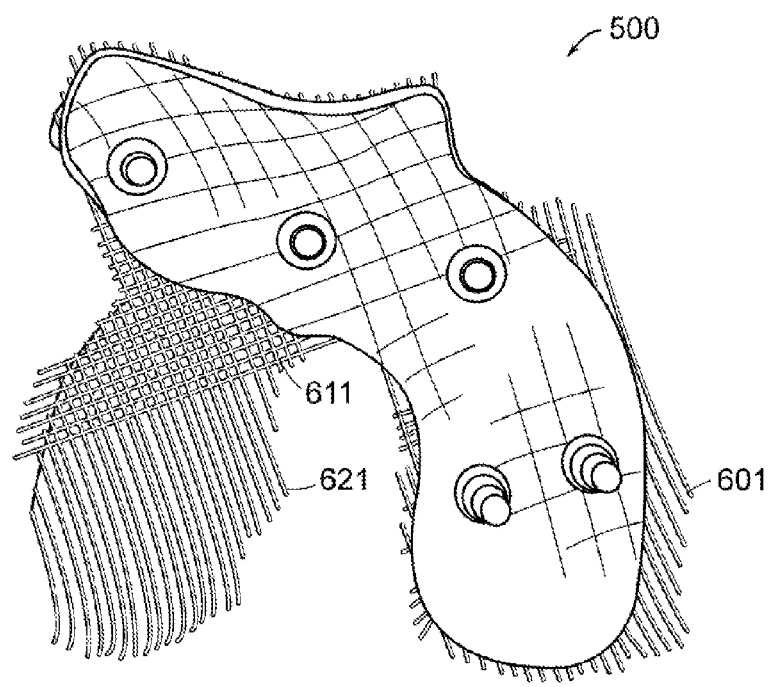
Figure 10C:
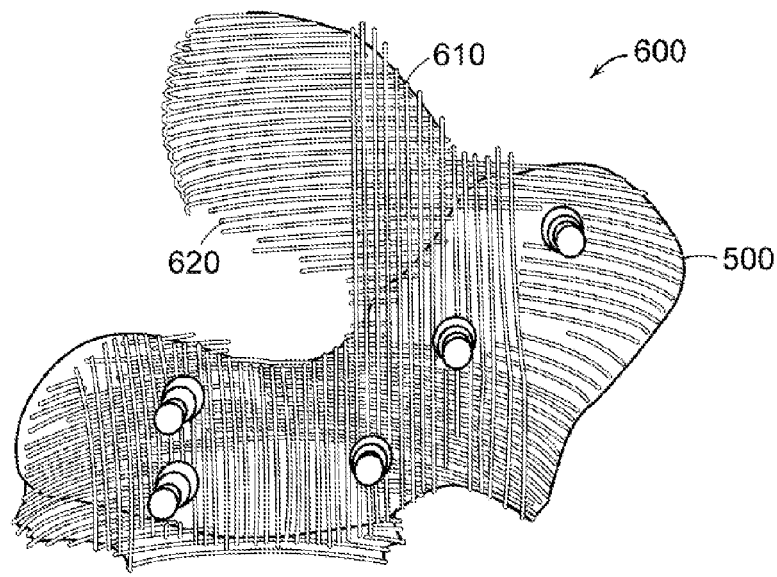
Figure 10D:
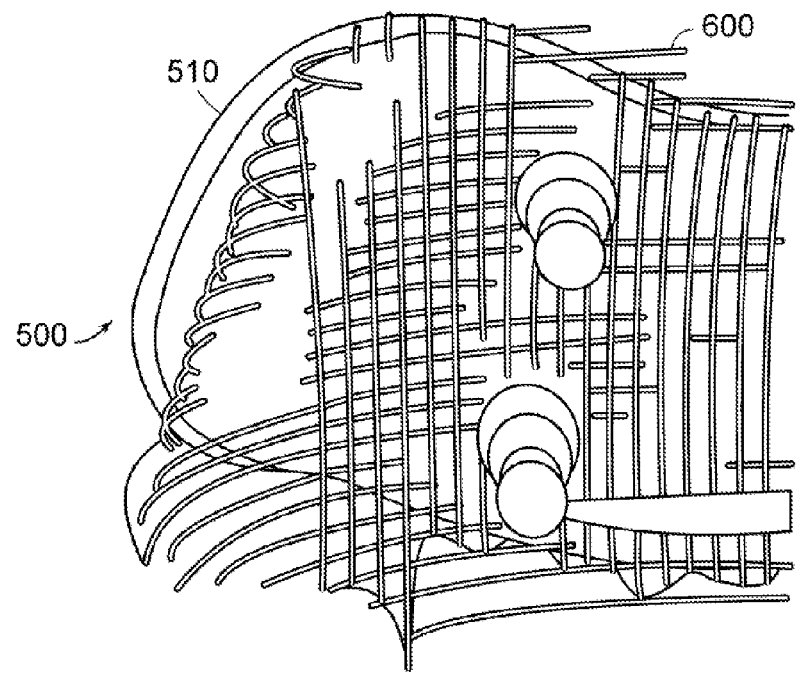
Figure 10E:
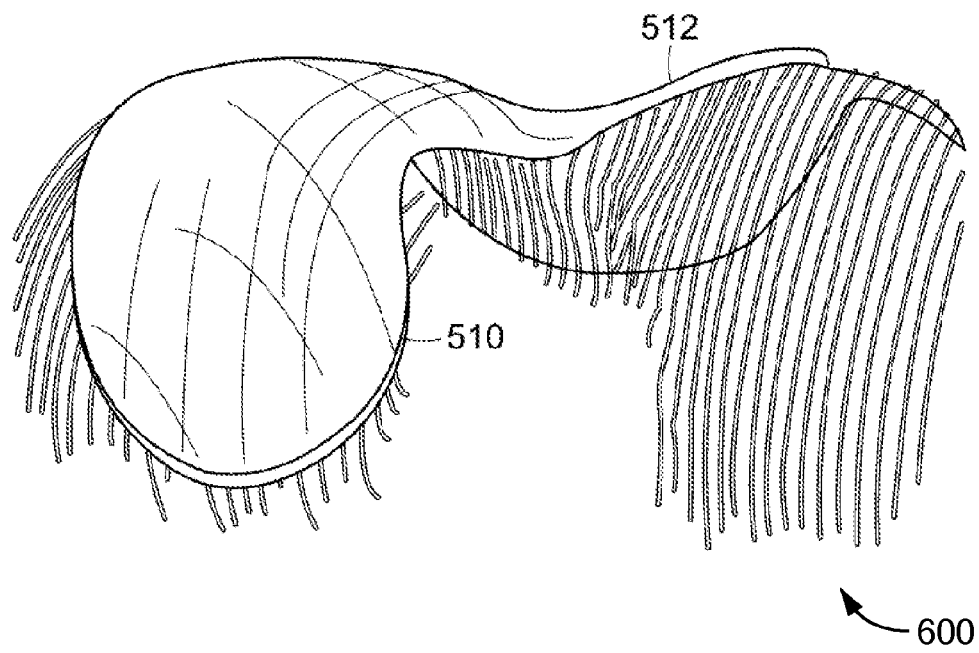
Figure 10F:
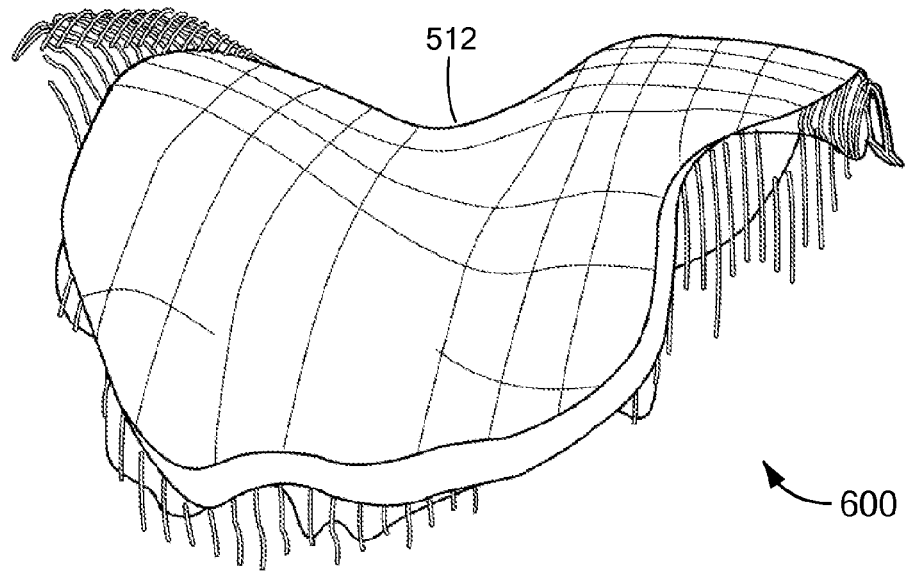
Figure 10G:
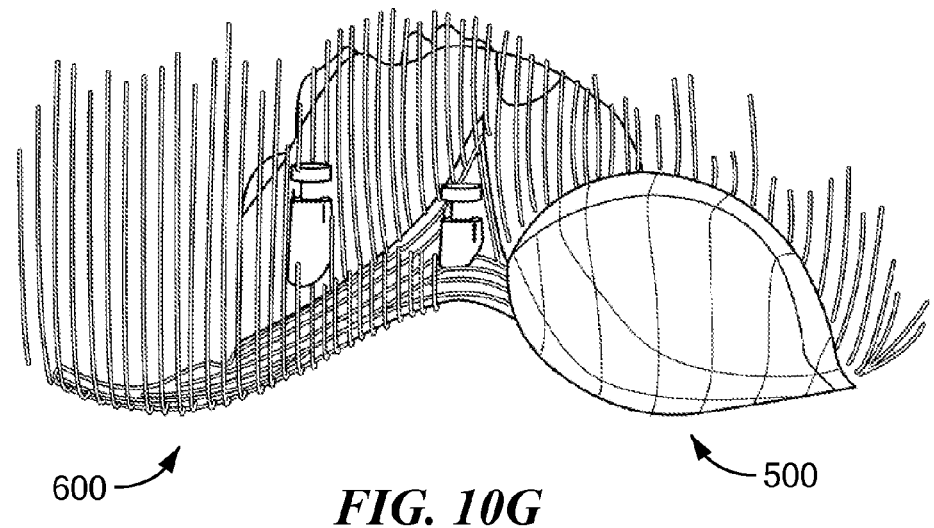

FIG. 10B illustrates a bottom view of the implant 500 layered over another derived surface shape 601. FIG. 10C is a bottom view showing the implant 500 extending through the extracted surface shape 600 shown in FIG. 10A. FIG. 10D is a close-up view of the FIG. 10C showing the condylar wing of the implant covering the extracted surface 600. FIG. 10E illustrates a top posterior view of the implant 500 positioned over the graphical representation of the surface shape 600. FIG. 10F is an anterior view of the implant 500 on the graphical representation of the surface shape 600 and FIG. 10G is a bottom-posterior view of the implant 500 on the graphical representation of the surface shape 600.

3.4.9 Two-Component Bicompartmental Device

Figure 11A:
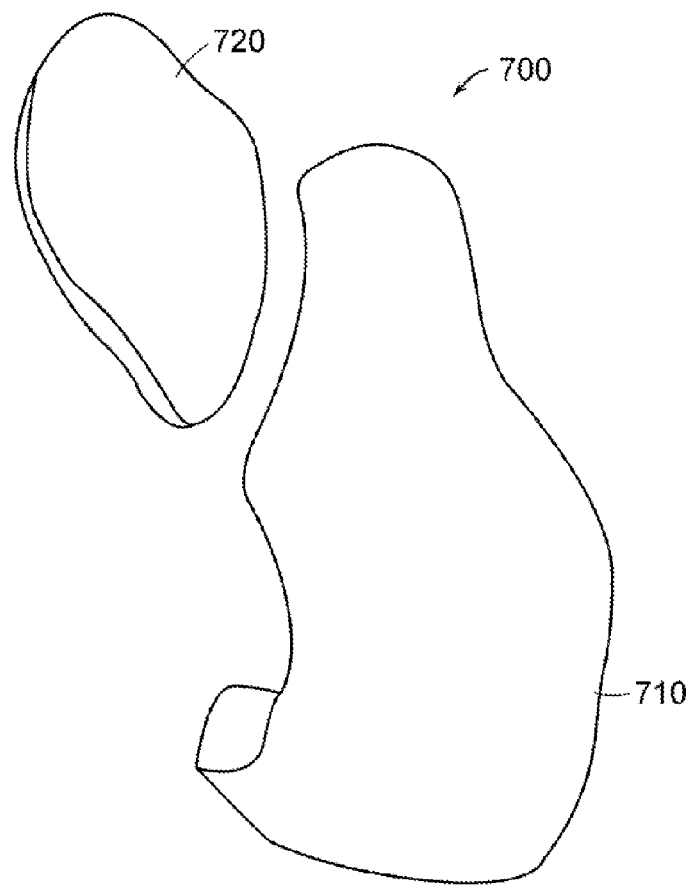
FIGS. 11A-C illustrate an alternate design of a device, suitable for a portion of the femoral condyle, having a two piece configuration.
Figure 11B:
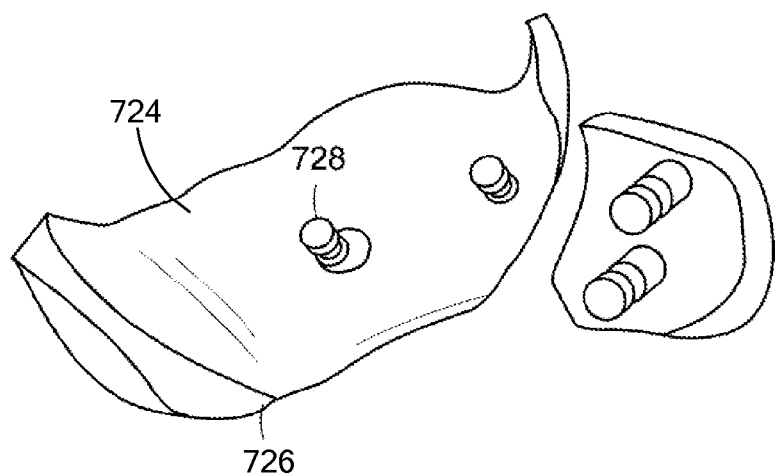
Figure 11C:
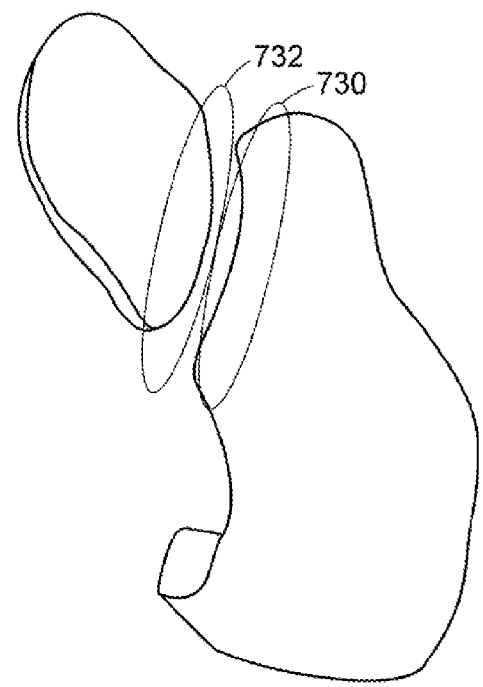

FIG. 11A-11C illustrate an implant 700 for correcting a joint similar to the implant 500 above. However, implant 700 includes two components. The first component 710 engages a condyle of the femur, either medial or lateral depending on the design. The second component 720 engages the patellar surface of the femur. As discussed with the previous embodiments, the surfaces of the implant 700 can be configured such that the distal surface 722 (e.g., the surface that faces the tibial plateau) is shaped based on a projection of the natural shape of the femur compensating the design for valgus or varus deformities and/or flattening of the surface of the femur. Alternatively, the distal surface can be shaped based on the shape of the tibial plateau to provide a surface designed to optimally mate with the tibial plateau. The proximal surface 724 (e.g., the surface that engages the femoral condyle) can be configured such that it substantially negatively matches the surface of the femur in either its damaged condition or its modified condition. Likewise, the proximal surface can have one or more flattened sections 726 that form, e.g., bone cuts. Additionally, the surface can include mechanisms facilitating attachment 728 to the femur, such as keels, teeth, cruciate stems, and the like. The medial facing portion of the condyle implant can have a tapered surface 730 while the lateral facing portion of the patellar component also can have a tapered surface such that each component presents tapered surfaces 730 to the other component.

By dividing the surfaces of the medial and lateral compartments into independent articulating surfaces, as shown in FIGS. 11A-11C, the implant provides improved fit of the conformal surfaces to the subchondral bone. Additionally, the lateral-anterior portion of the femur is shielded from stress which could cause bone loss. Also, the smaller size of each component of the implant enables the implant to be placed within the joint using a smaller incision. Finally, the wear of the patellar component may be improved.

3.2 Patellar Implant Component

FIGS. 12A-12F illustrate a patella 800 with an implant 810. The implant 810 can have one or more pegs, cruciate stems, or other anchoring mechanisms, if desired. As will be appreciated by those of skill in the art, other designs can be arrived at using the teachings of this disclosure. FIG. 12A illustrates a perspective view of an intact patella 800. FIG. 12B illustrates the patella 800 wherein one surface of the patella 800 has been cut to form a smooth surface 802 to mate with an implant. FIG. 12C illustrates the patella 800 with an implant 810 positioned on the smooth surface 802. The implant 810 has a plate structure 812 that abuts the smooth surface of the patella 802 and a dome 814 positioned on the plate 812 so that the dome is positioned in situ such that it matches the location of the patellar ridge. The implant 810 can be configured such that the edge of the plate is offset 1 mm from the actual edge of the patella, as illustrated. As will be appreciated by those of skill in the art, the plate 812 and dome 814 can be formed as a single unit or formed from multiple components. FIG. 12D is a side view of the implant 810 positioned on the patella 800. As shown, the dome is positioned on the implant such that it is off-center. Optimal positioning of the dome can be determined by the position of the patellar ridge.

Turning to FIGS. 12E-12F, the implant 810 is shown superimposed on the unaltered patella 800 in order to illustrate that the position of the dome 814 of the implant corresponds to the location of the patellar ridge.

Figure 12G:
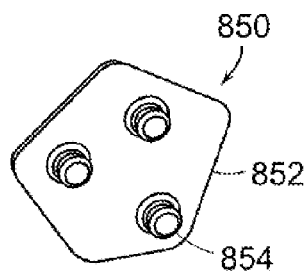
Figure 12H:
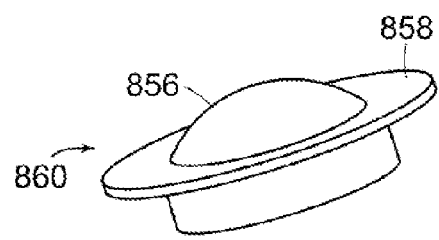
Figure 12I:
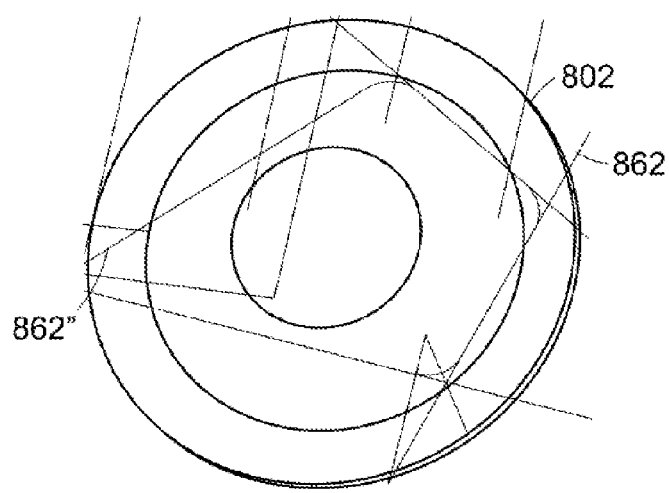
Figure 12J:
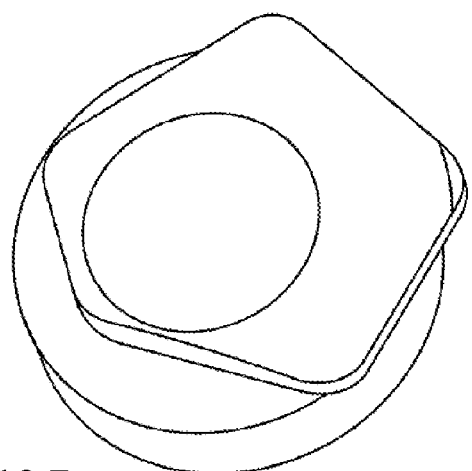

FIGS. 12G-J illustrate an alternative design for the patellar implant. FIG. 12G illustrates the implant 850 in its beginning stages as a blank with a flat inferior surface 852 having pegs 854 extending there from for anchoring to the patella. The articular or superior surface 860 has a rounded dome 856, and a round plate section 858 that can be machined to match the bone cut. The articular surface 860 takes on the appearance of a "hat" or sombrero, having a dome with a rim. The center of the dome 856 also is the center of the bearing surface. The rim 858 is cut to conform to the needs of the particular patient. FIG. 12J illustrates an implant which has been formed from the blank shown in FIGS. 12G-I. FIG. 12J shows a plurality of possible cut lines 862, 862' for purposes of illustration.

3.3 Combinations of Implant Components

Figure 13A:
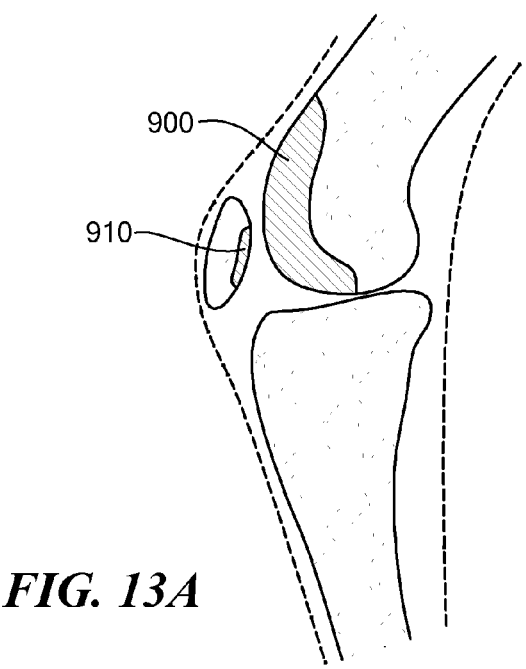
FIGS. 13A-C depict representative side views of a knee joint with any of the devices taught installed therein.
Figure 13B:
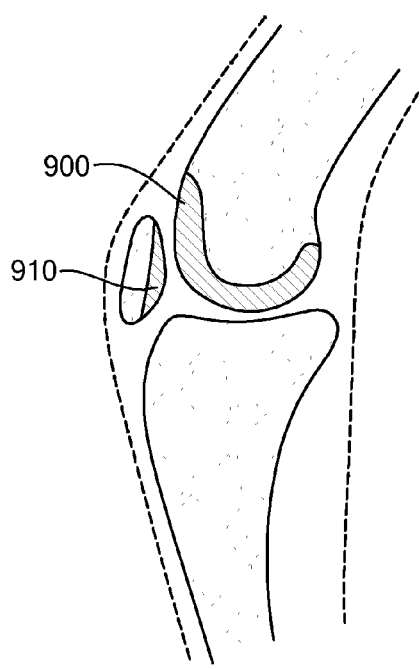
Figure 13C:
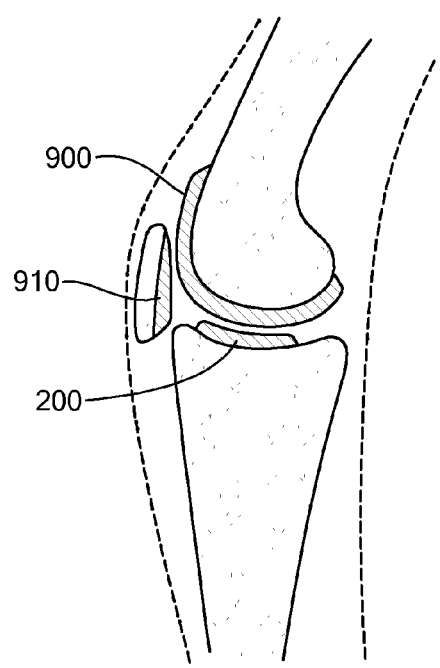
Figure 13D:
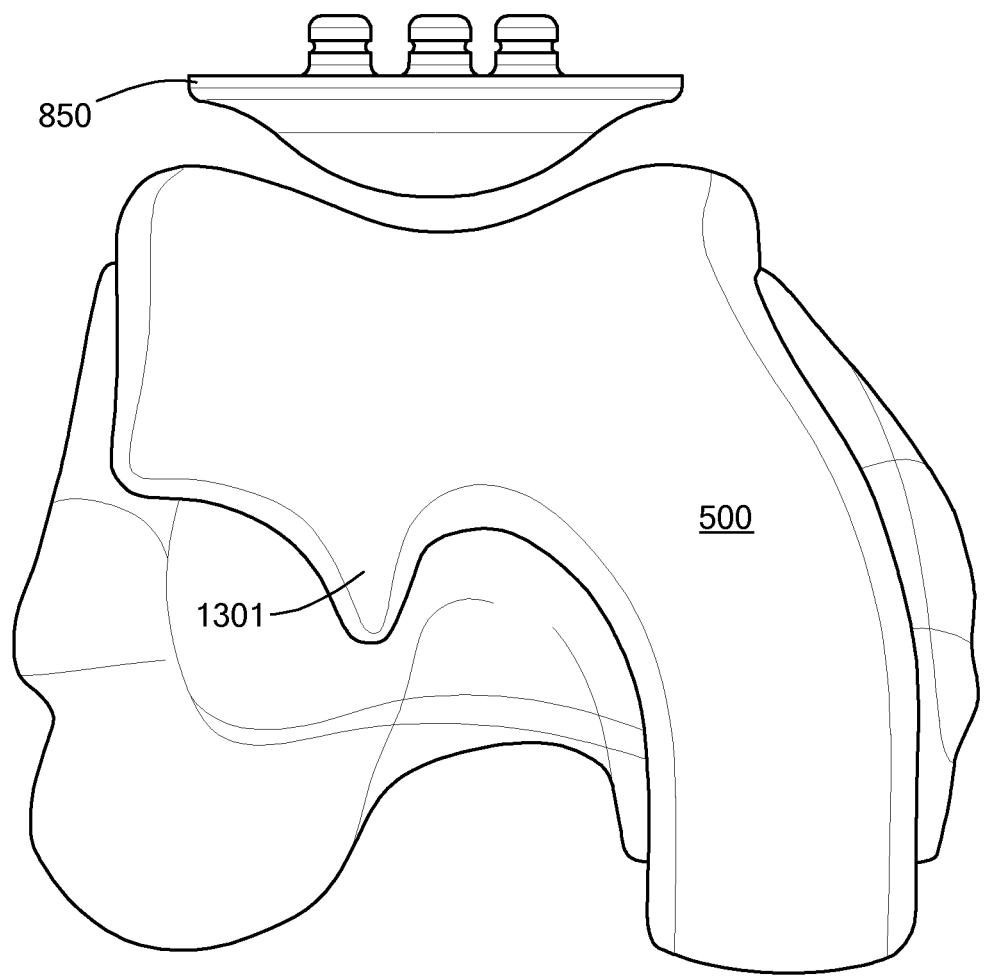
FIG. 13D shows another embodiment of the implant of FIG. 2 in place on a femur, with a patellar implant of FIG. 12.

FIGS. 13A-13C illustrate a lateral view of a knee having a combination of the implants described herein. In FIG. 13A, an implant covering the condyle 900, is illustrated. Suitable implants can be, for example, those shown in FIGS. 2-11. The portion of the condyle covered anterior to posterior can include the entire weight bearing surface, a portion thereof, or a surface greater than the weight bearing surface. Thus, for example, the implant can be configured to terminate prior to the sulcus terminalis or after the sulcus terminalis (e.g., the groove on the femur that coincides with the area where load bearing on the joint surface stops). As shown in FIGS. 13A-13B, a patellar implant 910 can also be provided. FIG. 13C illustrates a knee having a condyle implant 900, a patellar implant 910, and an implant for the tibial plateau 200. FIG. 13D shows a sombrero patellar implant 850 of FIG. 12 matched with another embodiment of a bicondylar implant placed on a model of a femur. This embodiment shows a portion 1301 of the implant 500 extending down the healthy condyle to provide additional patella coverage and tracking.

Figure 14A:
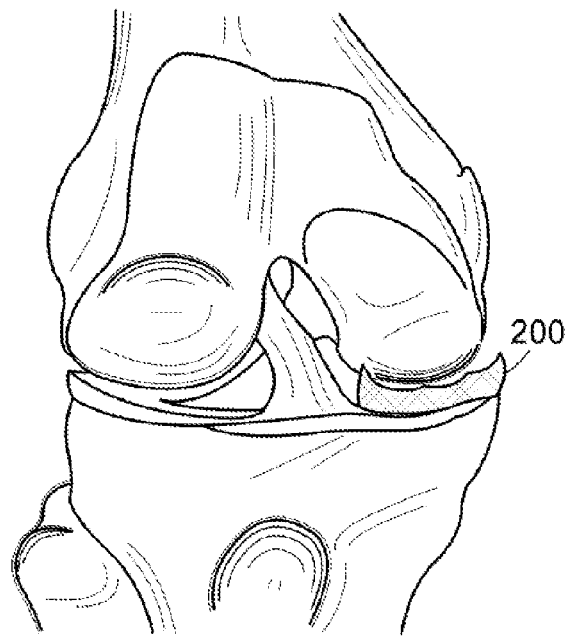
FIGS. 14A-D depict a frontal view of the knee joint with any of the devices taught installed therein.
Figure 14B:
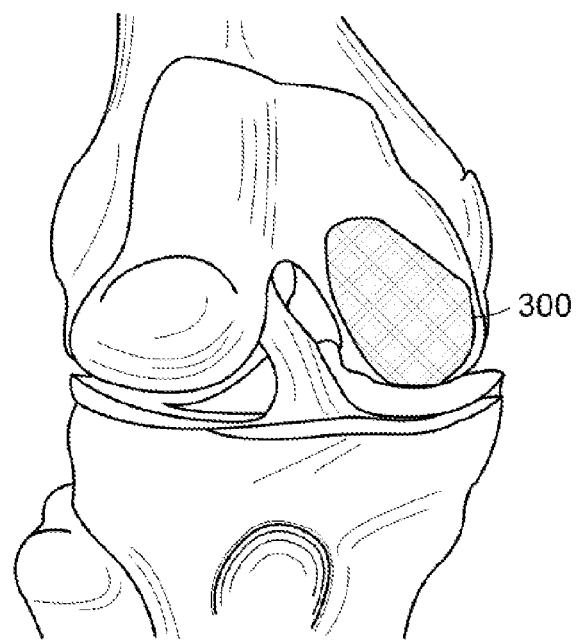
Figure 14C:
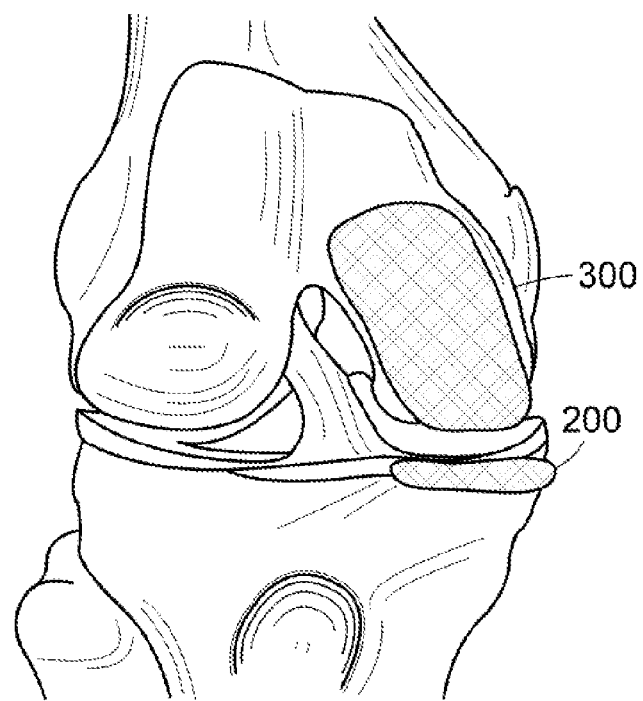
Figure 14D:
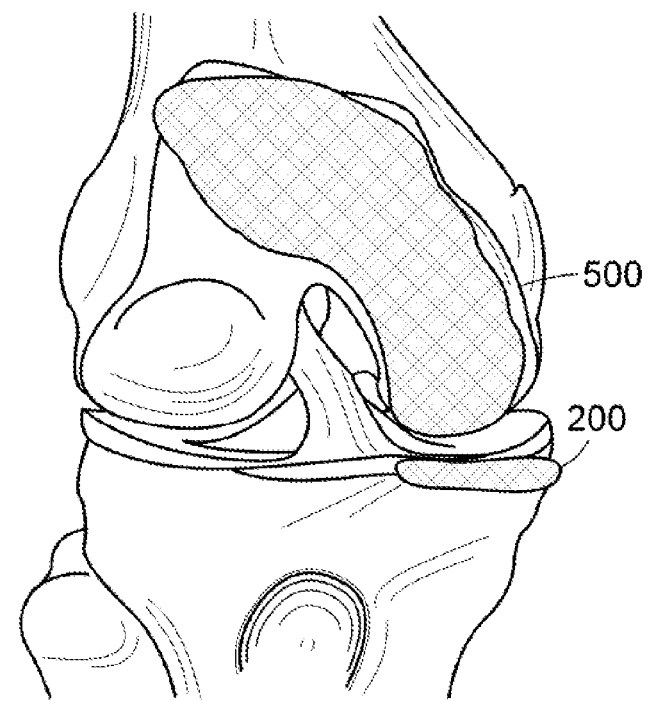

FIGS. 14A-14D provide an alternate view of the coronal plane of a knee joint with one or more implants described above implanted therein. FIG. 14A illustrates a knee having a tibial implant 200 placed therein. FIG. 14B illustrates a knee with a condyle implant 300 placed therein. As described above, a plurality of the implants taught herein can be provided within a joint in order to restore joint movement. FIG. 14C illustrates a knee joint having two implants therein. First, a tibial implant 200 is provided on the tibial plateau and a second implant 300 is provided on the facing condyle. The implants can be installed such that the implants present each other mating surfaces, as illustrated. Other combinations will be appreciated by those of skill in the art. Turning to FIG. 14D, a tibial implant 200 is provided along with a bicompartmental condyle implant 500. As discussed above, these implants can be associated with the same compartment of the knee joint, but need not be.

In another embodiment, the superior face of the implants 300, 400 or 500 can be shaped according to the femur. The shape can preferably be derived from the movement patterns of the femur relative to the tibial plateau thereby accounting for variations in femoral shape and tibiofemoral contact area as the femoral condyle flexes, extends, rotates, translates and glides on the tibia. The movement patterns can be measured using any current or future test know in the art such as fluoroscopy, MRI, gait analysis and combinations thereof.

In various embodiments, a joint implant may include two or more components that are slideably engageable forming a mobile bearing, as described in U.S. Patent Publication No. 2007-0100462. The mobile bearing can help provide more unconstrained or more physiologic motion in the joint, for example, knee motion of the femur relative to the tibia. In various embodiments, the joint implant may have one or more mobile bearings. The various components used for the mobile bearing joint implant may be composed of metal, plastic, ceramic or any other material know in the art. Different components may be composed of different materials, e.g. one metal and one plastic. Alternatively, only the same material may be used for the bearing surfaces, e.g. ceramic. The bearing surfaces of each component may vary in material composition e.g. ceramic on the side facing the femoral condyle and metal on the undersurface.

4. Implant Libraries

As described herein, repair systems of various sizes, curvatures and thicknesses can be obtained. These repair systems can be catalogued and stored to create a library of systems from which an appropriate system for an individual patient can then be selected. In other words, a defect, or an articular surface, is assessed in a particular subject and a pre-existing repair system having a suitable shape and size is selected from the library and, optionally, can be processed for further manipulation (e.g., shaping) and implantation.

5. Manufacturing

5.1 Shaping

In certain instances shaping of the repair material (e.g., of the repair system implant(s) and/or implant component(s)) may be required before or after formation (e.g., to achieve a desired thickness), for example, where the thickness of the required repair material is not uniform (e.g., where the patient-specific, patient-engineered, and/or standard dimensions require different thicknesses).

The replacement material can be shaped by any suitable technique including, but not limited to, casting techniques, mechanical abrasion, laser abrasion or ablation, radiofrequency treatment, cryoablation, variations in exposure time and concentration of nutrients, enzymes or growth factors and any other means suitable for influencing or changing the desired shape feature, such as thickness. See, e.g., WO 00/15153 to Mansmann published Mar. 23, 2000; If enzymatic digestion is used, certain sections of the replacement or regenerating material can be exposed to higher doses of the enzyme or can be exposed longer as a means of achieving different thicknesses and curvatures of the replacement or regenerating material in different sections of said material.

The material can be shaped manually and/or automatically, for example, using a device into which a pre-selected thickness and/or curvature has been input and then programming the device using the input information to achieve the desired shape. In addition to, or instead of, shaping the repair material, the site of implantation (e.g., bone surface, any cartilage material remaining, etc.) can also be shaped by any suitable technique in order to enhance integration of the repair material.

5.2 Sizing

The repair system can be formed or selected so that it achieves an anatomic or near anatomic fit or match with the surrounding or adjacent cartilage, subchondral bone, menisci and/or other tissue. Alternatively or in addition, the repair system can be engineered or selected so that it achieves an optimized fit or match with the surrounding or adjacent cartilage, subchondral bone, menisci, other tissue, and/or other implant structure in the joint. The shape of the repair system can be based on the analysis of an electronic image (e.g. MRI, CT, digital tomosynthesis, optical coherence tomography or the like). If the repair system is intended to replace an area of a diseased or modified anatomic structure, the anatomic, near anatomic, or optimized fit can be achieved based, at least in part, on a virtual reconstruction of the shape of the patient's healthy joint or an ideal joint in an electronic image.

In certain embodiments, a near normal cartilage surface at the position of the defect can be reconstructed by interpolating the healthy cartilage surface across the defect or area of disease. This can, for example, be achieved by describing the healthy cartilage by means of a parametric surface (e.g. a B-spline surface), for which the control points are placed such that the parametric surface follows the contour of the healthy cartilage and bridges the defect or area of disease. The continuity properties of the parametric surface can provide a smooth integration of the part that bridges the defect or area of disease with the contour of the surrounding healthy cartilage. The part of the parametric surface over the area of the defect or area of disease can be used to determine the shape or part of the shape of the repair system to match with the shape of the cartilage surface.

In other embodiments, a near normal cartilage surface at the position of the defect or area of disease can be reconstructed using morphological image processing. In a first step, the cartilage can be extracted from the electronic image using manual, semi-automated and/or automated segmentation techniques (e.g., manual tracing, region growing, live wire, model-based segmentation), resulting in a binary image. Defects in cartilage can appear as indentations that can be filled with a morphological closing operation performed in 2-D or 3-D with an appropriately selected structuring element. The closing operation is typically defined as a dilation followed by an erosion. A dilation operator sets the current pixel in the output image to 1 if at least one pixel of the structuring element lies inside a region in the source image. An erosion operator sets the current pixel in the output image to 1 if the whole structuring element lies inside a region in the source image. The filling of the defect or area of disease creates a new surface over the area of the defect or area of disease that can be used to determine the shape or part of the shape of the repair system to match with the surrounding cartilage or subchondral bone.

As described above, the repair system can be formed or selected from a library or database of systems of various sizes, curvatures and thicknesses so that it achieves a near anatomic fit or match, or an optimized fit, with the surrounding or adjacent cartilage and/or subchondral bone. These systems can be pre-made or made to order for an individual patient. In order to control the fit or match of the repair system with the surrounding or adjacent cartilage or subchondral bone or menisci and other tissues preoperatively, a software program can be used that projects the repair system over the anatomic position where it is implanted. Suitable software is commercially available and/or readily modified or designed by a skilled programmer.

In yet another embodiment, the repair system can be projected over the implantation site using one or more 3-D images. The cartilage and/or subchondral bone and other anatomic structures are extracted from a 3-D electronic image such as an MRI or a CT using manual, semi-automated and/or automated segmentation techniques. A 3-D representation of the cartilage and/or subchondral bone and other anatomic structures as well as the repair system is generated, for example using a polygon or NURBS surface or other parametric surface representation. For a description of various parametric surface representations see, for example Foley, J. D. et al., Computer Graphics: Principles and Practice in C; Addison-Wesley, 2nd edition, 1995).

The 3-D representations of the cartilage and/or subchondral bone and other anatomic structures and the repair system can be merged into a common coordinate system. The repair system can then be placed at the desired implantation site. The representations of the cartilage, subchondral bone, menisci and other anatomic structures and the repair system are rendered into a 3-D image, for example application programming interfaces (APIs) OpenGL® (standard library of advanced 3-D graphics functions developed by SGI, Inc.; available as part of the drivers for PC-based video cards, for example from www.nvidia.com for NVIDIA video cards or www.3dlabs.com for 3Dlabs products, or as part of the system software for Unix workstations) or DirectX® (multimedia API for Microsoft Windows® based PC systems; available from www.microsoft.com). The 3-D image can be rendered showing the cartilage, subchondral bone, menisci or other anatomic objects, and the repair system from varying angles, e.g. by rotating or moving them interactively or non-interactively, in real-time or non-real-time.

The software can be designed so that the repair system, including surgical tools and instruments with the best fit relative to the cartilage and/or subchondral bone is automatically selected, for example using some of the techniques described above. Alternatively, the operator can select a repair system, including surgical tools and instruments and project it or drag it onto the implantation site using suitable tools and techniques. The operator can move and rotate the repair systems in three dimensions relative to the implantation site and can perform a visual inspection of the fit between the repair system and the implantation site. The visual inspection can be computer assisted. The procedure can be repeated until a satisfactory fit has been achieved. The procedure can be performed manually by the operator; or it can be computer-assisted in whole or part. For example, the software can select a first trial implant that the operator can test. The operator can evaluate the fit. The software can be designed and used to highlight areas of poor alignment between the implant and the surrounding cartilage or subchondral bone or menisci or other tissues. Based on this information, the software or the operator can then select another implant and test its alignment. One of skill in the art will readily be able to select, modify and/or create suitable computer programs for the purposes described herein.

In another embodiment, the implantation site can be visualized using one or more cross-sectional 2-D images. Typically, a series of 2-D cross-sectional images are used. The 2-D images can be generated with imaging tests such as CT, MRI, digital tomosynthesis, ultrasound, or optical coherence tomography using methods and tools known to those of skill in the art. The repair system can then be superimposed onto one or more of these 2-D images. The 2-D cross-sectional images can be reconstructed in other planes, e.g. from sagittal to coronal, etc. Isotropic data sets (e.g., data sets where the slice thickness is the same or nearly the same as the in-plane resolution) or near isotropic data sets can also be used. Multiple planes can be displayed simultaneously, for example using a split screen display. The operator can also scroll through the 2-D images in any desired orientation in real time or near real time; the operator can rotate the imaged tissue volume while doing this. The repair system can be displayed in cross-section utilizing different display planes, e.g. sagittal, coronal or axial, typically matching those of the 2-D images demonstrating the cartilage, subchondral bone, menisci or other tissue. Alternatively, a three-dimensional display can be used for the repair system. The 2-D electronic image and the 2-D or 3-D representation of the repair system can be merged into a common coordinate system. The repair system can then be placed at the desired implantation site. The series of 2-D cross-sections of the anatomic structures, the implantation site and the repair system can be displayed interactively (e.g. the operator can scroll through a series of slices) or non-interactively (e.g. as an animation that moves through the series of slices), in real-time or non-real-time.

5.3 Rapid Prototyping

Rapid prototyping is a technique for fabricating a three-dimensional object from a computer model of the object. A special printer is used to fabricate the prototype from a plurality of two-dimensional layers. Computer software sections the representations of the object into a plurality of distinct two-dimensional layers and then a three-dimensional printer fabricates a layer of material for each layer sectioned by the software. Together the various fabricated layers form the desired prototype. More information about rapid prototyping techniques is available in U.S. Patent Publication No. 2002/0079601A1 to Russell et al., published Jun. 27, 2002. An advantage to using rapid prototyping is that it enables the use of free form fabrication techniques that use toxic or potent compounds safely. These compounds can be safely incorporated in an excipient envelope, which reduces worker exposure.

A powder piston and build bed is provided. Powder includes any material (metal, plastic, etc.) that can be made into a powder or bonded with a liquid. The power is rolled from a feeder source with a spreader onto a surface of a bed. The thickness of the layer is controlled by the computer. The print head then deposits a binder fluid onto the powder layer at a location where it is desired that the powder bind. Powder is again rolled into the build bed and the process is repeated, with the binding fluid deposition being controlled at each layer to correspond to the three-dimensional location of the device formation. For a further discussion of this process see, for example, U.S. Patent Publication No 2003/017365A1 to Monkhouse et al. published Sep. 18, 2003.

The rapid prototyping can use the two dimensional images obtained, as described above in Section 1, to determine each of the two-dimensional shapes for each of the layers of the prototyping machine. In this scenario, each two dimensional image slice would correspond to a two dimensional prototype slide. Alternatively, the three-dimensional shape of the defect can be determined, as described above, and then broken down into two dimensional slices for the rapid prototyping process. The advantage of using the three-dimensional model is that the two-dimensional slices used for the rapid prototyping machine can be along the same plane as the two-dimensional images taken or along a different plane altogether.

Rapid prototyping can be combined or used in conjunction with casting techniques. For example, a shell or container with inner dimensions corresponding to an repair system can be made using rapid prototyping. Plastic or wax-like materials are typically used for this purpose. The inside of the container can subsequently be coated, for example with a ceramic, for subsequent casting. Using this process, personalized casts can be generated.

Rapid prototyping can be used for producing repair systems. Rapid prototyping can be performed at a manufacturing facility. Alternatively, it may be performed in the operating room after an intraoperative measurement has been performed.

6. Surgical Techniques

Prior to performing surgery on a patient, the surgeon can preoperatively make a determination of the alignment of the knee using, for example, an erect AP x-ray. In performing preoperative assessment any lateral and patella spurs that are present can be identified.

Using standard surgical techniques, the patient is anesthetized and an incision is made in order to provide access to the portion or portions of the knee joint to be repaired. A medial portal can be used initially to enable arthroscopy of the joint. Thereafter, the medial portal can be incorporated into the operative incision and/or standard lateral portals can be used.

Once an appropriate incision has been made, the exposed compartment is inspected for integrity, including the integrity of the ligament structures. If necessary, portions of the meniscus can be removed as well as any spurs or osteophytes that were identified in the AP x-ray or that may be present within the joint. In order to facilitate removal of osteophytes, the surgeon may flex the knee to gain exposure to additional medial and medial-posterior osteophytes. Additionally, osteophytes can be removed from the patella during this process. If necessary, the medial and/or lateral meniscus can also be removed at this point, if desired, along with the rim of the meniscus.

As would be appreciated by those of skill in the art, evaluation of the medial cruciate ligament may be required to facilitate tibial osteophyte removal. Once the joint surfaces have been prepared, the desired repair system (e.g., implant(s) and/or implant component(s) can be inserted into the joint.

EXAMPLE

This Example illustrates a process for designing and assessing three different bicompartmental knee implants or implant components. This Example also illustrates three different bicompartmental knee implants or implant components having patient-specific and/or engineered aspects or features.

Figure 15A:
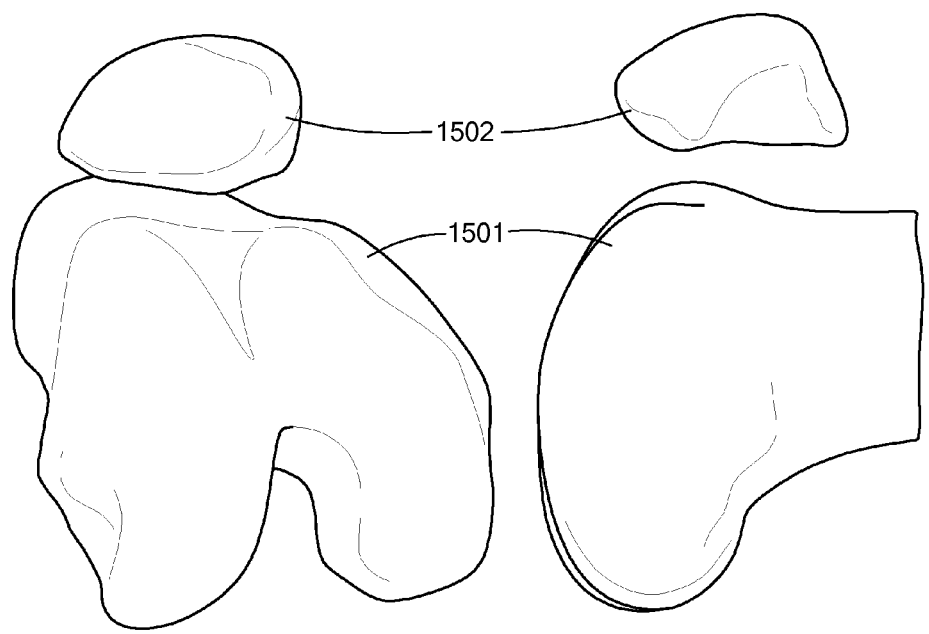
FIG. 15A shows images of a particular patient's femur and patella.
Figure 15B:
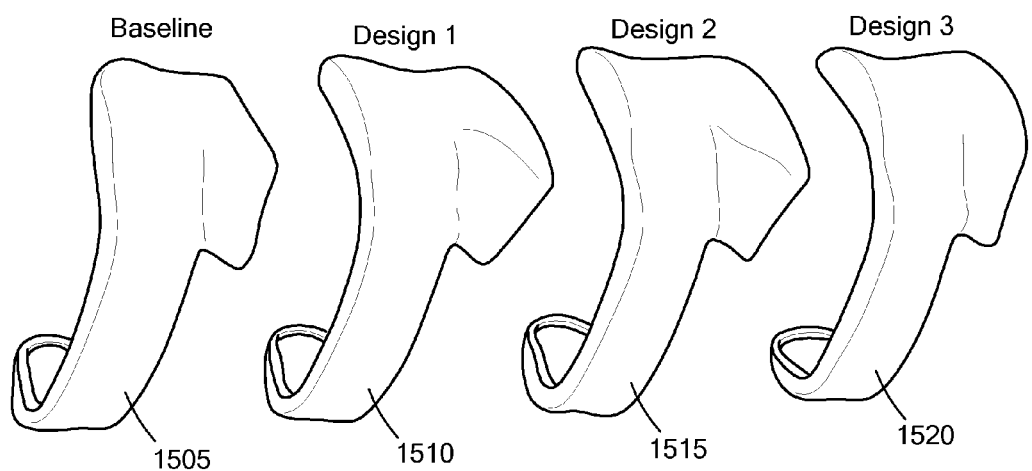
FIG. 15B illustrates three different bicompartmental implants or implant components (Designs 1-3) and a bicompartmental implant or implant component having no bone cuts ("Baseline").

Three different bicompartmental implants or implant components having anterior and posterior cuts were designed for a particular patient's right knee having a femur segment volume of 156.7 cm$^3$. The three implants or implant components then were compared to a bicompartmental implant or implant component having only a posterior bone cut. FIG. 15A shows images of the particular patient's femur 1501 and patella 1502 and FIG. 15B illustrates the three different bicompartmental implants or implant components 1510-1520 ("Designs 1-3") and the bicompartmental implant or implant component having no bone cuts 1505 ("Baseline"). Table 1 includes a description of the resection volume, implant volume, and implant mass for each of the three implant designs and for the baseline implant.

TABLE 1

| | | Implant Designs | | | |
|---|---|---|---|---|---|
| | Description | Resection volume (cm 3) | % Change from Baseline | Implant Volume (cm 3) | Implant Mass (g) | % Change from Baseline |
| Baseline | Single, posterior bone cut | 1.6 | — | 12.9 | 107.1 | — |
| Design 1 | Posterior and anterior bone cuts; 2 mm sub-basal anterior cut; 2 mm PF joint relief and same angles | 5.3 | 231% | 17.0 | 141.1 | 32% |
| Design 2 | Same as Design-1 but with patella implant optimized PF region | 5.4 | 238% | 17.8 | 147.7 | 38% |
| Design 3 | Same as Design-2 but with flex angles adjusted for bone preservation | 3.1 | 94% | 14.8 | 122.8 | 15% |

Figure 15E:
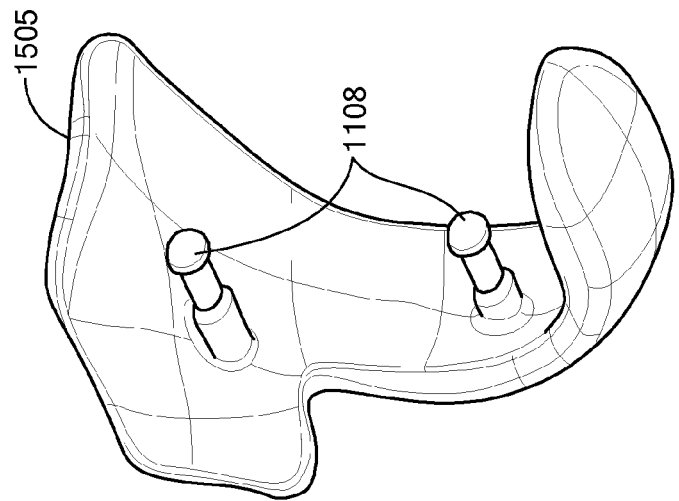
FIGS. 15C-15E illustrate an implant design and bone resection for a bicompartmental implant that includes only a single, posterior bone cut.
Figure 15D:
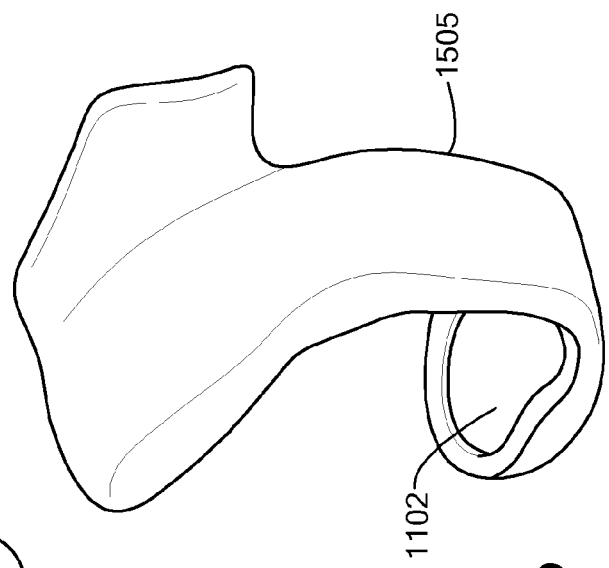
Figure 15C:
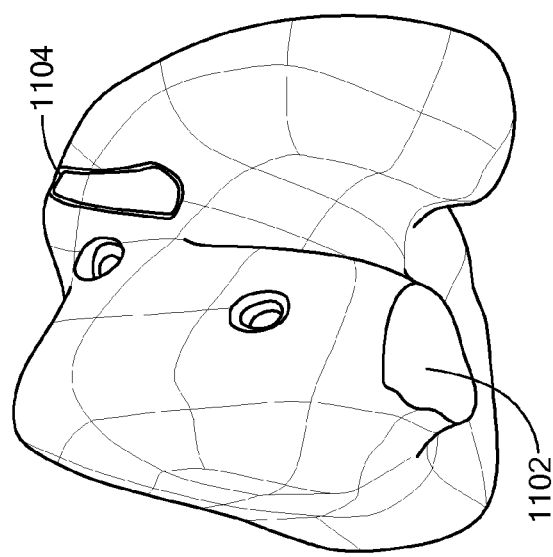

As shown in FIGS. 15C-15E, the baseline bicompartmental implant or implant component 1505 was designed to include only a single, posterior bone cut 1102, which differs by 12 degrees from the mechanical axis. The design also includes a small cut (also referred to as a dive in) 1104 on the anterior portion of the condyle (that is not covered by the implant) to allow for sinking the edge of the implant or implant component into this bone cut. The anterior flange is short to prevent closing of the "C" shape of the implant, which otherwise would prohibit fitting the implant onto the femur. In addition, the inner proximal edge of the anterior flange is flared for clearance. The pegs 1108 are set 15 degrees off the mechanical axis.

Figure 16C:
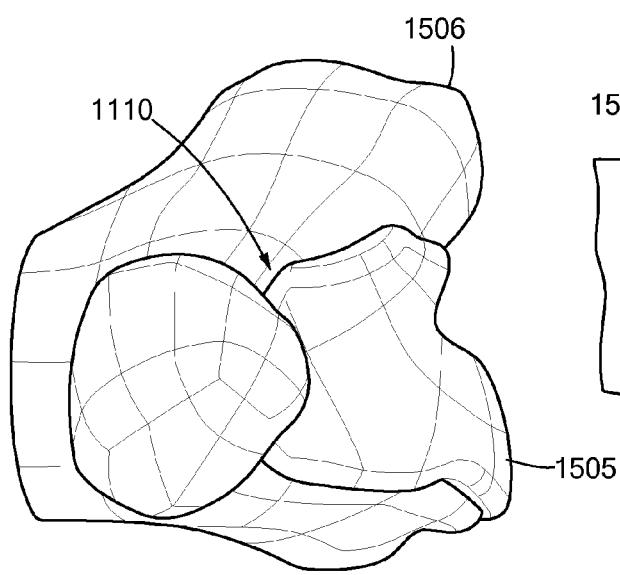
Figure 16C:
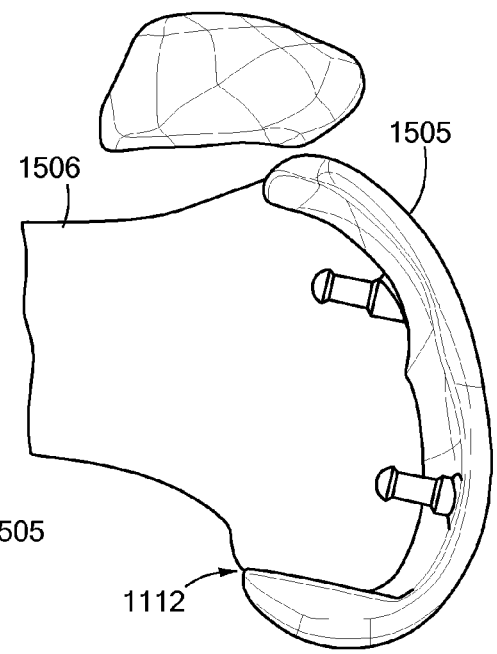
Figure 16C:
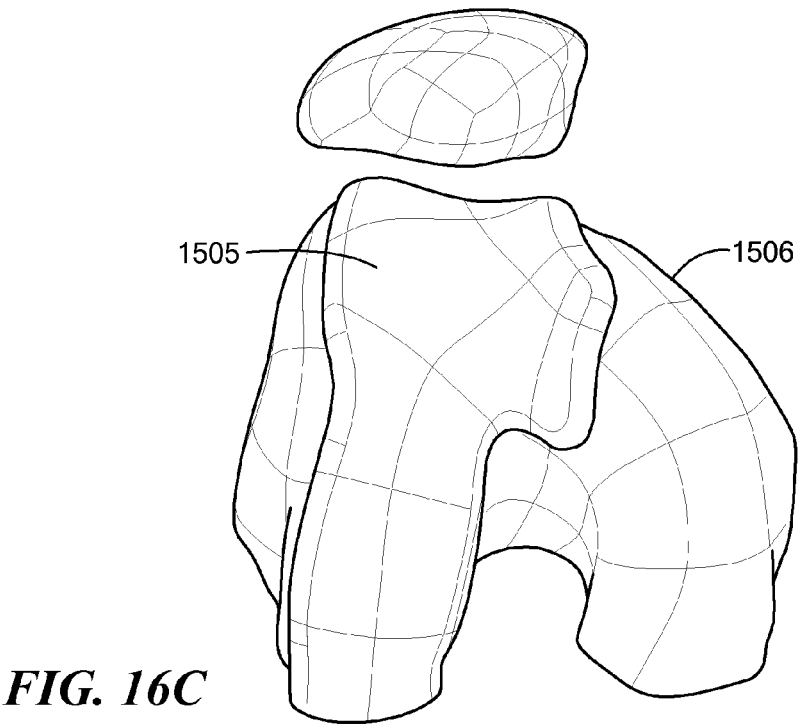

FIGS. 16A-16C illustrate the baseline bicompartmental implant or implant component 1505 in place on a model of a femur 1506. As shown in FIG. 16A, the implant or implant component offers limited anterior coverage 1110 of the PF region when the knee is in flexion. However, as shown in FIG. 16B, the baseline bicompartmental implant or implant component offers substantial posterior coverage 1112. The thickness of this implant in the posterior region was 8.5 mm. With this implant or implant component, the bone lost to resection was 1.6 cm$^3$ (initial segment volume of 156.7 cm$^3$—final segment volume of 155.1 cm$^3$).

Figure 17C:
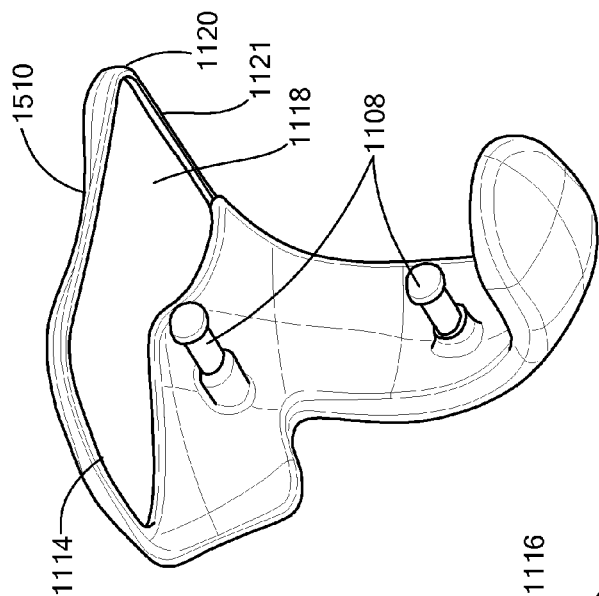
FIGS. 17A-17C illustrate an implant design and bone resectioning for a bicompartmental implant that includes both a posterior bone cut and an anterior bone cut.
Figure 17B:
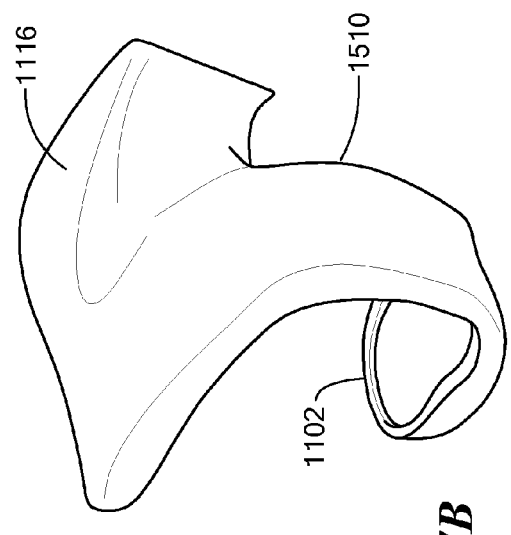
Figure 17A:
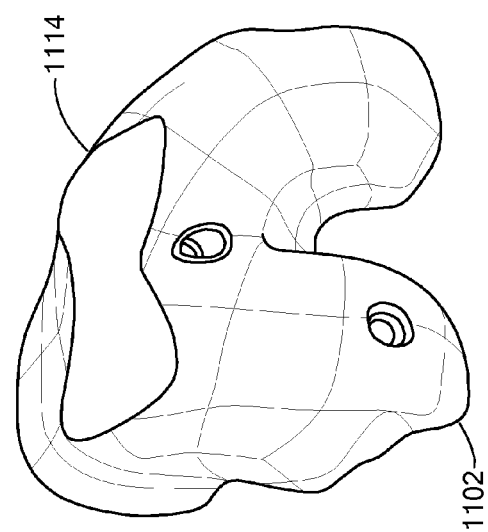

As shown in FIGS. 17A-17C, the first bicompartmental implant or implant component design 1510 ("Design 1") included both a posterior bone cut 1102 and an anterior bone cut 1114. The anterior bone cut was designed to be 2 mm below the basal point of the trochlear groove so that the PF region was relieved 2 mm evenly. The PF region 1116 of the implant or implant component also was designed to be patient specific, for example, so that one or more of the coronal and sagittal curvatures of the trochlear groove substantially matched the patient's coronal and sagittal curvatures. The posterior cut 1102 and pegs 1108 are set at the same angle, and the anterior flange is 5 degrees divergent from the posterior cut and peg angle. In this design, a cement pocket 1118 was included and the proximal edge 1120 of the anterior flange 1121 was substantially straight.

FIGS. 18A-18C illustrate the first bicompartmental implant or implant component design 1510 ("Design 1") in place on a model of a femur 1511. As shown in FIG. 18A, the implant or implant component offers substantially more anterior coverage 1110 of the PF region when the knee is in flexion, as compared to the baseline design (see FIG. 16A). In addition, as shown in FIG. 18B, 1510 also offers substantial posterior coverage 1112. The thickness of this implant in the anterior region is 8.5 mm on the lateral side and 8.0 mm on the medial side. However, with this implant or implant component, the bone lost to resection was 5.3 cm$^3$ (initial segment volume of 156.7 cm$^3$—final segment volume of 151.4 cm$^3$).

As shown in FIGS. 19A-19C, the second bicompartmental implant or implant component design 1515 ("Design 2") included the posterior and anterior bone cuts as described with 1510, Design 1. Specifically, the anterior bone cut 1114 was designed to be 2 mm below the basal point. All other unaffected surfaces of the implant had about 4 mm thickness. In addition, the anterior flange cut 1121 and coverage and the posterior coverage for 1515, Design 2 were the same as described above for 1510, Design 1. However, dissimilarly to 1510, Design 1, the PF region 1116 of the implant or implant component of 1515, Design 2 was engineered to optimize the trochlear groove fit with a patellar implant component. The posterior cut 1102 and peg angles 1108 for 1515, Design 2 were as described above for 1510, Design 1.

FIGS. 20A-20C illustrate the second bicompartmental implant or implant component 1515 ("Design 2") in place on a model of a femur 1516. The thickness of this implant in the anterior region is 9.8 mm on the lateral side and 9.0 mm on the medial side. With this implant or implant component, the bone lost to resection was 5.4 cm$^3$ (initial segment volume of 156.7 cm$^3$—final segment volume of 151.3 cm$^3$).

As shown in FIGS. 21A-21C, the third bicompartmental implant or implant component design 1520 ("Design 3") included the posterior cut 1114 and anterior bone cuts 1102 as described with 1515, Design 2. In addition, the anterior flange cut 1121 and coverage for 1520, Design 3 was the similar as described above for 1515, Design 2. However, the flex of the cuts was altered to preserve bone. Specifically, the anterior cut was shifted to be 6 degrees off the mechanical axis and the posterior cut was shifted to be 1.5 degrees off the mechanical axis. Similar to 1515, Design 2, the PF region 1116 of the implant or implant component of 1520, Design 3 was engineered to optimize the trochlear groove fit with a patellar implant component. The peg angles 1108 for 1520, Design 3 were 7.6 degrees off the mechanical axis.

Figure 22A:
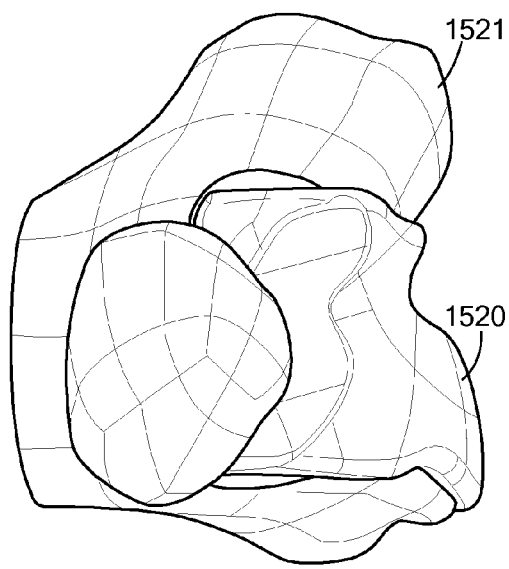
FIGS. 22A-22C illustrate the implant of FIGS. 21A-21C in place on a femur.
Figure 22B:
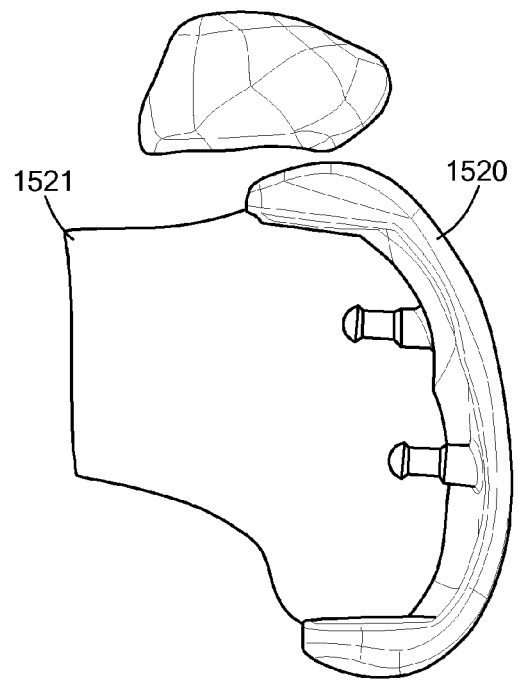
Figure 22C:
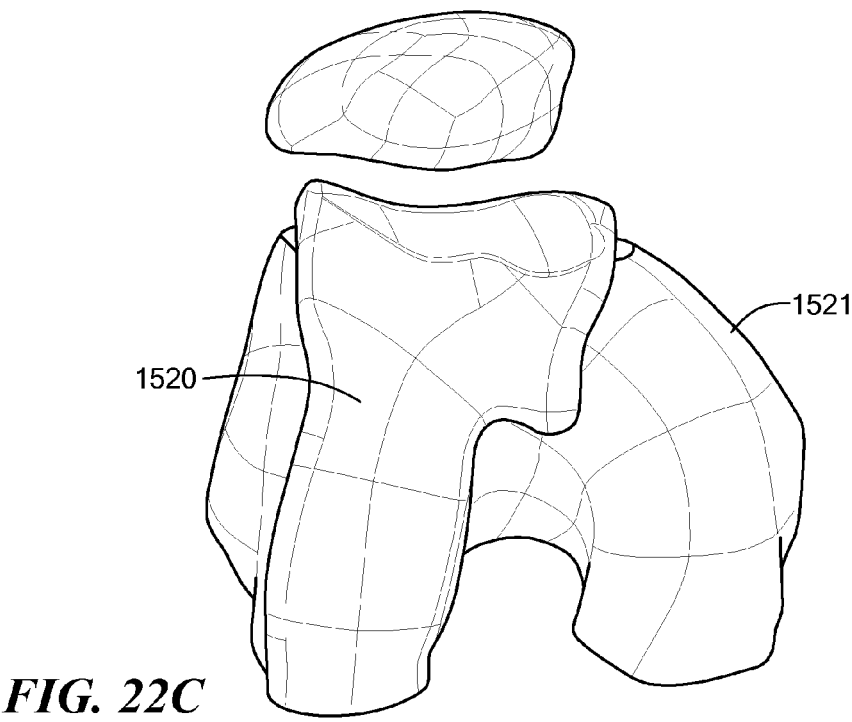

FIGS. 22A-22C illustrate the third bicompartmental implant or implant component 1520 ("Design 3") in place on a model of a femur 1521. The thickness of this implant in the anterior region is 8 mm on the lateral side and 7.5 mm on the medial side. The posterior flange coverage was less than that for Design 2, due to the change in the flex angle. However, with this implant or implant component, the bone lost to resection was only 3.1 cm$^3$ (initial segment volume of 156.7 cm$^3$—final segment volume of 153.6 cm$^3$).

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A patient-specific bicompartmental knee implant for implantation into a patient's knee joint, the implant comprising:
    a body having a condylar portion and a trochlear portion, wherein the condylar portion has a shape generally resembling a surface of a condyle of the patient's knee joint and the trochlear portion having a shape generally resembling the surface of a trochlea of the patient's knee joint, wherein the trochlear portion includes a patellofemoral (PF) region having a standard coronal curvature selected from a family of standard curvatures and a patient-specific sagittal curvature;
    the condylar portion further having an articular surface, wherein at least a portion of the articular surface is configured to have a three-dimensional shape that includes articular shape information of a corresponding portion of the condyle of the patient's knee joint; and
    the condylar portion further having a bone-facing surface opposite the articular surface, wherein at least a first portion of the bone-facing surface is planar and at least a second portion of the bone-facing surface substantially matches a corresponding portion of an articular surface of the patient's knee joint.

2. The implant of claim 1 wherein the planar portion of the bone-facing surface is located on a posterior of the condylar portion.

3. The implant of claim 1, wherein the condylar portion further comprises a third portion of the bone-facing surface, wherein the third portion is substantially planar.

4. The implant of claim 3, wherein the first and third portions are disposed at anterior and posterior ends of the implant and the second portion is disposed between the first and third portions.

5. The implant of claim 1, wherein the trochlear portion further comprises an articular surface wherein at least a portion of the articular surface is configured such that a curve of the at least a portion of the articular surface substantially matches a curve of a corresponding portion of an articular surface of the trochlea of the patient's knee joint.

6. The implant of claim 1, wherein the trochlear portion further comprises a bone-facing surface opposite the articular surface, wherein at least a portion of the bone-facing surface is planar.

7. A patient-specific bicompartmental knee implant for implantation into a patient's knee joint, the implant comprising:
    a body having a condylar portion and a trochlear portion, wherein the condylar portion has a shape generally resembling a surface of a condyle of the patient's knee joint and the trochlear portion having a shape generally resembling the surface of a trochlea of the patient's knee joint, wherein the trochlear portion includes a patellofemoral (PF) region having a standard coronal curvature selected from a family of standard curvatures and a patient-specific sagittal curvature;
    the condylar portion further having an articular surface wherein at least a portion of the articular surface is configured to have a three-dimensional shape that includes articular shape information of a corresponding portion of the condyle of the patient's knee joint; and the trochlear portion having a bone-facing surface and an articular surface, wherein the bone-facing surface is generally opposite the articular surface and wherein at least a portion of the bone-facing surface is planar.

8. The implant of claim 7, wherein the condylar portion further comprises a bone-facing surface opposite the articular surface, wherein at least a portion of the bone-facing surface is planar.

9. The implant of claim 7, wherein the condylar portion further comprises a bone-facing surface opposite the articular surface, wherein at least a portion of the bone-facing surface substantially matches a corresponding portion of an articular surface of the patient's knee joint.

10. The implant of claim 7, wherein the condylar portion further comprises a bone-facing surface opposite the articular surface, wherein at least a portion of the bone-facing surface is planar and at least a second portion of the bone-facing surface substantially matches a corresponding portion of an articular surface of the patient's knee joint.

11. The implant of claim 10, wherein the planar portion of the bone-facing surface is located on a posterior of the condylar portion.

12. The implant of claim 7, wherein the condylar portion further comprises a bone-facing surface opposite the articular surface, wherein at least a first portion of the bone-facing surface is substantially planar, at least a second portion of the bone-facing surface substantially matches a corresponding portion of an articular surface of the patient's knee joint, and at least a third portion of the bone-facing surface is substantially planar.

13. The implant of claim 12, wherein the first and third portions are disposed at anterior and posterior ends of the implant and the second portion is disposed between the first and third portions.

14. The implant of claim 7, wherein at least a portion of the articular surface of the trochlear portion is configured such that a curve of the at least a portion of the articular surface substantially matches a curve of a corresponding portion of an articular surface of a trochlea of the patient's knee joint.

* * * * *